(12) United States Patent
Garcia et al.

(10) Patent No.: US 11,633,218 B2
(45) Date of Patent: Apr. 25, 2023

(54) PECTUS BAR AND STABILIZER DEVICES AND METHODS

(71) Applicant: Zimmer Biomet CMF and Thoracic, LLC, Jacksonville, FL (US)

(72) Inventors: Saddy Garcia, St. Augustine, FL (US); Jayden Garfield, Jacksonville, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 121 days.

(21) Appl. No.: 17/034,697

(22) Filed: Sep. 28, 2020

(65) Prior Publication Data

US 2021/0007785 A1    Jan. 14, 2021

Related U.S. Application Data

(63) Continuation of application No. 15/893,271, filed on Feb. 9, 2018, now Pat. No. 10,820,931.
(Continued)

(51) Int. Cl.
*A61B 17/80* (2006.01)
*A61F 2/28* (2006.01)
(Continued)

(52) U.S. Cl.
CPC ........ *A61B 17/8076* (2013.01); *A61B 17/808* (2013.01); *A61B 17/8019* (2013.01);
(Continued)

(58) Field of Classification Search
CPC ............ A61B 17/8042; A61B 17/8047; A61B 17/8076; A61B 17/80; A61B 17/808; A61B 17/8019; A61B 17/8875; A61B 17/7049; A61F 2/28; A61F 2002/30482; A61F 2002/4622
(Continued)

(56) References Cited

U.S. PATENT DOCUMENTS 212,242 A    2/1879    Loper
2,616,328 A  * 11/1952 Kingsmore ............. F16B 29/00
                                                411/80.2
(Continued)

FOREIGN PATENT DOCUMENTS

CN    101123922 A    2/2008
CN    201930064 U    8/2011
(Continued)

OTHER PUBLICATIONS

"Australian Application Serial No. 2018230818, Subsequent Examiners Report dated Sep. 21, 2020", 4 pgs.
(Continued)

*Primary Examiner* — Jessica Weiss
(74) *Attorney, Agent, or Firm* — Schwegman Lundberg & Woessner, P.A.

(57) ABSTRACT

A pectus bar pectus bar assembly can include a pectus bar and a stabilizer. The pectus bar can include a first portion including a first periphery and a second portion opposite the first portion. The stabilizer can include a stabilizer body including a recess engageable with the second portion. The stabilizer can also include a locking cam rotatable within the body to secure the stabilizer to the first portion.

14 Claims, 40 Drawing Sheets

Related U.S. Application Data

(60) Provisional application No. 62/483,494, filed on Apr. 10, 2017, provisional application No. 62/457,532, filed on Feb. 10, 2017.

(51) Int. Cl.
*A61B 17/88* (2006.01)
*A61F 2/30* (2006.01)
*A61F 2/46* (2006.01)

(52) U.S. Cl.
CPC .......... *A61B 17/8875* (2013.01); *A61F 2/28* (2013.01); *A61F 2002/30482* (2013.01); *A61F 2002/4622* (2013.01)

(58) Field of Classification Search
USPC ...... 606/70–71, 280–299, 99, 905, 191, 198
See application file for complete search history.

(56) References Cited

U.S. PATENT DOCUMENTS

| | | | |
|---|---|---|---|
| 3,693,616 A * | 9/1972 | Roaf | A61B 17/7049 606/250 |
| 3,946,728 A | 3/1976 | Bettex | |
| 4,082,332 A | 4/1978 | Palmer | |
| 4,201,215 A | 5/1980 | Crossett et al. | |
| 4,202,327 A | 5/1980 | Glancy | |
| 4,327,715 A | 5/1982 | Corvisier | |
| 5,092,889 A | 3/1992 | Campbell, Jr. | |
| 5,601,554 A * | 2/1997 | Howland | A61B 17/7049 606/252 |
| 5,605,364 A | 2/1997 | Shelledy | |
| 5,755,808 A | 5/1998 | Decarlo et al. | |
| 6,005,018 A | 12/1999 | Cicierega et al. | |
| 6,007,538 A | 12/1999 | Levin | |
| 6,024,759 A * | 2/2000 | Nuss | A61B 17/68 606/237 |
| 6,139,550 A * | 10/2000 | Michelson | A61B 17/80 606/295 |
| 6,306,136 B1 | 10/2001 | Baccelli | |
| 6,355,038 B1 | 3/2002 | Pisharodi | |
| 6,656,179 B1 | 12/2003 | Schaefer et al. | |
| 6,689,134 B2 | 2/2004 | Ralph et al. | |
| 6,872,210 B2 | 3/2005 | Hearn | |
| 7,156,847 B2 | 1/2007 | Abramson | |
| 7,601,165 B2 | 10/2009 | Stone | |
| 8,597,327 B2 | 12/2013 | Stone et al. | |
| 8,715,285 B2 | 5/2014 | Lewis et al. | |
| 8,876,823 B2 | 11/2014 | Li | |
| 9,138,272 B2 | 9/2015 | Roman et al. | |
| 9,339,388 B2 * | 5/2016 | Dartevelle | A61B 17/8076 606/60 |
| 9,668,792 B2 | 6/2017 | Roman et al. | |
| 9,743,968 B2 * | 8/2017 | Licht | A61B 17/8076 606/60 |
| 9,775,657 B2 | 10/2017 | Bernstein et al. | |
| 9,833,269 B2 | 12/2017 | Park | |
| 9,872,708 B2 | 1/2018 | Park | |
| 10,058,364 B2 | 8/2018 | Garcia | |
| 10,617,455 B2 | 4/2020 | Maxson | |
| 10,722,279 B2 | 7/2020 | Balzano et al. | |
| 10,820,931 B2 | 11/2020 | Garcia et al. | |
| 11,432,858 B2 | 9/2022 | Balzano et al. | |
| 2002/0143336 A1 | 10/2002 | Hearn | |
| 2003/0153915 A1 * | 8/2003 | Nekozuka | A61B 17/7062 606/248 |
| 2003/0225409 A1 * | 12/2003 | Freid | A61B 17/7059 606/281 |
| 2004/0030338 A1 | 2/2004 | Paul | |
| 2004/0116931 A1 | 6/2004 | Carlson | |
| 2004/0117016 A1 * | 6/2004 | Abramson | A61B 17/8076 623/16.11 |
| 2004/0204713 A1 | 10/2004 | Abdou | |
| 2005/0049595 A1 * | 3/2005 | Suh | A61B 17/7059 606/71 |
| 2006/0058786 A1 * | 3/2006 | Kim | A61B 17/8076 606/60 |
| 2006/0089648 A1 | 4/2006 | Masini | |
| 2006/0259141 A1 | 11/2006 | Roman et al. | |
| 2006/0276794 A1 * | 12/2006 | Stern | A61B 17/86 606/287 |
| 2008/0082101 A1 | 4/2008 | Relsberg | |
| 2008/0097444 A1 | 4/2008 | Erickson et al. | |
| 2008/0262549 A1 | 10/2008 | Bennett et al. | |
| 2009/0062918 A1 | 3/2009 | Wang | |
| 2010/0256691 A1 | 10/2010 | Park | |
| 2011/0160776 A1 * | 6/2011 | Erickson | A61B 17/8052 606/286 |
| 2011/0251540 A1 | 10/2011 | Notrica | |
| 2012/0130371 A1 | 5/2012 | Li et al. | |
| 2012/0303121 A1 | 11/2012 | Douget et al. | |
| 2013/0165934 A1 * | 6/2013 | Ibrahim | A61B 17/7059 606/71 |
| 2013/0020431 A1 | 8/2013 | Roman et al. | |
| 2013/0204310 A1 * | 8/2013 | Roman | A61B 17/8076 606/86 R |
| 2014/0117016 A1 | 5/2014 | Hodge | |
| 2014/0135853 A1 | 5/2014 | Reisberg | |
| 2014/0163691 A1 | 6/2014 | Dartevelle | |
| 2014/0214103 A1 | 7/2014 | Roman et al. | |
| 2014/0309699 A1 | 10/2014 | Houff | |
| 2014/0378976 A1 | 12/2014 | Garcia | |
| 2015/0038969 A1 | 2/2015 | Garcia et al. | |
| 2015/0045794 A1 * | 2/2015 | Garcia | A61B 17/82 606/74 |
| 2015/0119887 A1 * | 4/2015 | May | A61B 17/1728 606/71 |
| 2015/0134009 A1 | 5/2015 | Licht et al. | |
| 2015/0238237 A1 | 8/2015 | Madjarov | |
| 2016/0074078 A1 | 3/2016 | Roman et al. | |
| 2016/0296262 A1 | 10/2016 | Garcia et al. | |
| 2016/0310180 A1 | 10/2016 | Prybis et al. | |
| 2016/0367301 A1 | 12/2016 | Madjarov | |
| 2017/0156759 A1 | 6/2017 | Park | |
| 2017/0215930 A1 * | 8/2017 | Lauf | A61B 17/7059 606/71 |
| 2017/0238981 A1 | 8/2017 | Madjarov et al. | |
| 2018/0228523 A1 | 8/2018 | Balzano et al. | |
| 2018/0228524 A1 | 8/2018 | Garcia et al. | |
| 2018/0256227 A1 | 9/2018 | Maxson | |
| 2018/0303527 A1 | 10/2018 | Su | |
| 2018/0310973 A1 | 11/2018 | Son et al. | |
| 2018/0368896 A1 | 12/2018 | Powell | |
| 2019/0046251 A1 | 2/2019 | Detweiler et al. | |
| 2019/0059964 A1 | 2/2019 | Notrica | |
| 2019/0069938 A1 | 3/2019 | Martinez-Ferro et al. | |
| 2019/0314072 A1 | 10/2019 | Uemura et al. | |
| 2020/0197058 A1 * | 6/2020 | Maxson | A61B 17/68 |
| 2020/0315676 A1 | 10/2020 | Balzano et al. | |

FOREIGN PATENT DOCUMENTS

| | | |
|---|---|---|
| CN | 203059880 U | 7/2013 |
| CN | 103767778 A | 5/2014 |
| CN | 104856748 A | 8/2015 |
| CN | 204683752 U | 10/2015 |
| CN | 105517501 | 4/2016 |
| CN | 110325135 A | 10/2019 |
| CN | 110366391 A | 10/2019 |
| EP | 0583520 A1 | 2/1994 |
| EP | 1721580 A1 | 11/2006 |
| JP | 2000501624 A | 2/2000 |
| JP | 2016168086 A | 9/2016 |
| JP | 2020508102 A | 3/2020 |
| JP | 2020509827 A | 4/2020 |
| WO | WO-2004028412 A1 | 4/2004 |
| WO | WO-2013003719 A1 | 1/2013 |
| WO | WO-2015003061 A1 | 1/2015 |
| WO | WO-2015056204 A1 | 4/2015 |
| WO | WO-2015142588 A2 | 9/2015 |
| WO | WO-2017023147 A1 | 2/2017 |

(56) References Cited

FOREIGN PATENT DOCUMENTS

| | | |
|---|---|---|
| WO | WO-2017157802 A1 | 9/2017 |
| WO | WO-2018148521 A1 | 8/2018 |
| WO | WO-2018148572 A1 | 8/2018 |
| WO | WO-2018164808 A1 | 9/2018 |

OTHER PUBLICATIONS

"Canadian Application Serial No. 3,053,113, Office Action dated Sep. 25, 2020", 4 pgs.
"Australian Application Serial No. 2018230818, Response filed Nov. 20, 2020 to Subsequent Examiners Report dated May 28, 2020", 11 pgs.
"Canadian Application Serial No. 3,054,790, Office Action dated Nov. 12, 2020", 4 pgs.
"Canadian Application Serial No. 3,053,113, Response to Office Action dated Sep. 25, 2020", 29 pgs.
U.S. Appl. No. 15/893,271, filed Feb. 9, 2018, Pectus Bar and Stabilizer Devices and Methods.
U.S. Appl. No. 15/892,926 U.S. Pat. No. 10,722,279, filed Feb. 9, 2018, Stabilizer Holder and Inserter Tool and Methods.
U.S. Appl. No. 16/908,188, filed Jun. 22, 2020, Stabilizer Holder and Inserter Tool and Methods.
U.S. Appl. No. 15/892,847 U.S. Pat. No. 10,617,455, filed Feb. 9, 2018, Pectus Bar Support Devices and Methods.
U.S. Appl. No. 16/804,325, filed Feb. 28, 2020, Pectus Bar Support Devices and Methods.
U.S. Appl. No. 11/402,319, filed Apr. 11, 2006, Pectus Bar Stabilizer.
U.S. Appl. No. 13/662,975 U.S. Pat. No. 8,715,285, filed Oct. 29, 2012, Pectus Bar Stabilizer.
U.S. Appl. No. 14/243,246 U.S. Pat. No. 9,138,272, filed Apr. 2, 2014, Pectus Bar Stabilizer.
U.S. Appl. No. 14/857,422 U.S. Pat. No. 9,668,792, filed Sep. 17, 2015, Pectus Bar Stabilizer.
"U.S. Appl. No. 19/804,325, Notice of Allowance dated Dec. 27, 2021", 11 pgs.
"U.S. Appl. No. 16/908,188, Non Final Office Action dated Feb. 1, 2022", 16 pgs.
"Canadian Application Serial No. 3,053,113, Office Action dated May 31, 2021", 5 pgs.
"Canadian Application Serial No. 3,053,113, Response filed Sep. 29, 2021 to Office Action dated May 31, 2021", 20 pgs.
"Canadian Application Serial No. 3,054,790, Response filed Mar. 12, 2021 to Office Action dated Nov. 12, 2020", 13 pgs.
"Chinese Application Serial No. 201880011148.1, Response filed Jan. 4, 2022 to Notification of Paying the Restoration Fee mailed Nov. 18, 2021", w/ Claims, 6 pgs.
"Chinese Application Serial No. 201880014508.3, Office Action dated Nov. 17, 2021", w/ English translation, 9 pgs.
"Japanese Application Serial No. 2019-543354, Notification of Reasons for Refusal dated Jan. 5, 2021", (W/ English Translation), 11 pgs.
"Japanese Application Serial No. 2019-543354, Notification of Reasons for Refusal dated Dec. 7, 2021", w/ English translation, 8 pgs.
"Japanese Application Serial No. 2019-543354, Response filed Jun. 30, 2021 to Notification of Reasons for Refusal dated Jan. 5, 2021", w/ English claims, 13 pgs.
"Japanese Application Serial No. 2019-548548, Notification of Reasons for Refusal dated Jan. 5, 2021", (W/ English Translation), 10 pgs.
"Japanese Application Serial No. 2019-548548, Response filed Apr. 5, 2021 to Notification of Reasons for Refusal dated Jan. 5, 2021", w/ English claims, 10 pgs.
"U.S. Appl. No. 11/402,319, Advisory Action dated Oct. 13, 2009", 4 pgs.
"U.S. Appl. No. 11/402,319, Appeal Brief filed Jan. 4, 2010", 24 pgs.
"U.S. Appl. No. 11/402,319, Decision on Appeal mailed Aug. 29, 2012", 9 pgs.
"U.S. Appl. No. 11/402,319, Examiner Interview Summary dated Apr. 6, 2009", 2 pgs.
"U.S. Appl. No. 11/402,319, Final Office Action dated Aug. 5, 2009", 11 pgs.
"U.S. Appl. No. 11/402,319, Non Final Office Action dated Feb. 23, 2009", 10 pgs.
"U.S. Appl. No. 11/402,319, Reply Brief filed Apr. 26, 2010", 6 pgs.
"U.S. Appl. No. 11/402,319, Reply Brief filed Jun. 2, 2010", 6 pgs.
"U.S. Appl. No. 11/402,319, Response filed Jan. 27, 2009 to Restriction Requirement dated Dec. 31, 2008", 3 pgs.
"U.S. Appl. No. 11/402,319, Response filed Apr. 8, 2009 to Non Final Office Action dated Feb. 23, 2009", 11 pgs.
"U.S. Appl. No. 11/402,319, Response filed Sep. 24, 2009 to Final Office Action dated Aug. 5, 2009", 7 pgs.
"U.S. Appl. No. 11/402,319, Restriction Requirement dated Dec. 31, 2008", 9 pgs.
"U.S. Appl. No. 13/662,975, Notice of Allowance dated Dec. 24, 2013", 9 pgs.
"U.S. Appl. No. 13/662,975, Preliminary Amendment filed Jul. 1, 2013", 11 pgs.
"U.S. Appl. No. 13/662,975, Response filed Sep. 30, 2013 to Restriction Requirement dated Aug. 28, 2013", 9 pgs.
"U.S. Appl. No. 13/662,975, Restriction Requirement dated Aug. 28, 2013", 9 pgs.
"U.S. Appl. No. 14/243,246, Notice of Allowance dated May 20, 2015", 9 pgs.
"U.S. Appl. No. 14/531,US4, Response filed Jan. 12, 2017 to Final Office Action dated Dec. 7, 2016", 9 pgs.
"U.S. Appl. No. 14/857,422, Final Office Action dated Dec. 7, 2016", 12 pgs.
"U.S. Appl. No. 14/857,422, Non Final Office Action dated Apr. 19, 2016", 5 pgs.
"U.S. Appl. No. 14/857,422, Notice of Allowance dated Jan. 25, 2017", 7 pgs.
"U.S. Appl. No. 14/857,422, Response filed Sep. 19, 2016 to Non Final Office Action dated Apr. 19, 2016", 8 pgs.
"U.S. Appl. No. 15/892,847, Notice of Allowance dated Nov. 29, 2019", 10 pgs.
"U.S. Appl. No. 15/892,926, Non Final Office Action dated Nov. 29, 2019", 15 pgs.
"U.S. Appl. No. 15/892,926, Notice of Allowance dated Mar. 23, 2020", 11 pgs.
"U.S. Appl. No. 15/892,926, Response filed Feb. 19, 2020 to Non Final Office Action dated Nov. 29, 2019", 11 pgs.
"U.S. Appl. No. 15/893,271, Non Final Office Action dated Dec. 27, 2019", 12 pgs.
"U.S. Appl. No. 15/893,271, Notice of Allowance dated Jun. 29, 2020", 11 pgs.
"U.S. Appl. No. 15/893,271, Response filed Mar. 18, 2020 to Non Final Office Action dated Dec. 27, 2019", 13 pgs.
"U.S. Appl. No. 16/804,325, Preliminary Amendment filed Mar. 27, 2020", 6 pgs.
"U.S. Appl. No. 16/908,188, Preliminary Amendment filed Jun. 25, 2020", 7 pages.
"Australian Application Serial No. 2018217805, First Examination Report dated Nov. 25, 2019", 4 pgs.
"Australian Application Serial No. 2018217805, Response filed Feb. 25, 2020 First Examination Report dated Nov. 25, 2019", 25 pgs.
"Australian Application Serial No. 2018230818, First Examination Report dated Feb. 19, 2020", 5 pgs.
"Australian Application Serial No. 2018230818, Response filed May 5, 2020 to First Examination Report dated Feb. 19, 2020", 23 pgs.
"Australian Application Serial No. 2018230818, Response filed Aug. 28, 2020 to Subsequent Examiners Report dated May 28, 2020", 17 pgs.
"Australian Application Serial No. 2018230818, Subsequent Examiners Report dated May 28, 2020", 5 pgs.

(56) References Cited

OTHER PUBLICATIONS

"European Application Serial No. 18707802.7, Response to Communication pursuant to Rules 161(1) and 162 EPC filed Mar. 30, 2020", 11 pgs.

"European Application Serial No. 06009368.9, Communication Pursuant to Article 94(3) EPC dated Mar. 1, 2017", 5 pgs.

"European Application Serial No. 06009368.9, Communication Pursuant to Article 94(3) EPC dated Oct. 8, 2015", 4 pgs.

"European Application Serial No. 06009368.9, Extended European Search Report dated Sep. 15, 2006", 11 pgs.

"European Application Serial No. 06009368.9, Office Action dated Jun. 14, 2007", 1 pg.

"European Application Serial No. 06009368.9, Response filed Apr. 18, 2016 to Communication Pursuant to Article 94(3) EPC dated Oct. 8, 2015", 15 pgs.

"European Application Serial No. 06009368.9, Response filed Sep. 11, 2017 to Communication Pursuant to Article 94(3) EPC dated Mar. 1, 2017", 24 pgs.

"European Application Serial No. 06009368.9, Response filed Dec. 24, 2007 to Office Action dated Jun. 14, 2007", 11 pgs.

"European Application Serial No. 18706624.6, Response to Communication pursuant to Rules 161(1) and 162 EPC filed May 5, 2020", 11 pgs.

"European Application Serial No. 18707204.6, Response to Communication pursuant to Rules 161(1) and 162 EPC filed Mar. 30, 2020", 17 pgs.

"International Application Serial No. PCT/US2018/017582, International Preliminary Report on Patentability dated Sep. 19, 2019", 9 pgs.

"International Application Serial No. PCT/US2018/017582, International Search Report dated May 16, 2018", 7 pgs.

"International Application Serial No. PCT/US2018/017582, Written Opinion dated May 16, 2018", 7 pgs.

"International Application Serial No. PCT/US2018/017591, International Preliminary Report on Patentability dated Aug. 22, 2019", 11 pgs.

"International Application Serial No. PCT/US2018/017591, International Search Report dated Apr. 25, 2018", 7 pgs.

"International Application Serial No. PCT/US2018/017591, Written Opinion dated Apr. 25, 2018", 9 pgs.

"International Application Serial No. PCT/US2018/017663, International Preliminary Report on Patentability dated Aug. 22, 2019", 18 pgs.

"International Application Serial No. PCT/US2018/017663, International Search Report dated Jun. 18, 2018", 10 pgs.

"International Application Serial No. PCT/US2018/017663, Invitation to Pay Add'l Fees and Partial Search Report dated Apr. 23, 2018", 21 pgs.

"International Application Serial No. PCT/US201 8/017663, Written Opinion dated Jun. 18, 2018", 16 pgs.

"U.S. Appl. No. 16/804,325, Notice of Allowance dated Apr. 27, 2022", 8 pgs.

"U.S. Appl. No. 16/908,188, Examiner Interview Summary dated May 2, 2022", 2 pgs.

"U.S. Appl. No. 16/908,188, Notice of Allowance dated May 13, 2022", 8 pgs.

"U.S. Appl. No. 16/908,188, Response filed May 2, 2022 to Non Final Office Action dated Feb. 1, 2022", 12 pgs.

"Canadian Application Serial No. 3,053,113, Non Final Office Action dated Apr. 1, 2022", 5 pgs.

"Chinese Application Serial No. 201880011148.1, Office Action dated Feb. 14, 2022", w/ English Translation, 18 pgs.

"Chinese Application Serial No. 201880014508.3, Response filed Feb. 23, 22 to Office Action dated Nov. 17, 2021", w/ English claims, 10 pgs.

"European Application Serial No. 18707204.6, Communication Pursuant to Article 94(3) EPC dated Mar. 16, 2022", 8 pgs.

"Japanese Application Serial No. 2019-543354, Response filed Mar. 7, 2022 to Notification of Reasons for Refusal dated Dec. 7, 2021", w/English Claims, 15 pgs.

"European Application Serial No. 18707204.6, Response filed Jul. 26, 2022 to Communication Pursuant to Article 94(3) EPC dated Mar. 16, 2022", 52 pgs.

"Chinese Application Serial No. 201880011148.1, Office Action dated Aug. 31, 2022", w English Translation, 17 pgs.

\* cited by examiner

PECTUS BAR AND STABILIZER DEVICES AND METHODS

CLAIM OF PRIORITY

This application is a continuation of U.S. patent application Ser. No. 15/893,271, filed Feb. 9, 2018, which claims the benefit of U.S. Provisional Patent Application Ser. No. 62/457,532, filed on Feb. 10, 2017 and U.S. Provisional Patent Application Ser. No. 62/483,494, filed on Apr. 10, 2017, the benefit of priority of each of which is claimed hereby, and each of which are incorporated by reference herein in its entirety.

BACKGROUND

Pectus excavatum and pectus carinatum are conditions affecting a human chest wall which can result from a congenital disorder. In some cases of pectus excavatum and pectus carinatum, physicians install hardware into a patient's chest wall to reshape the chest wall. Depending on the anatomy of the patient, current hardware solutions may be difficult to secure to a patient's ribs. Further, because some surgical methods attempt to minimize the number and size of surgical incisions, hardware installed on the chest wall may be difficult for a physician to reach and/or operate to secure the hardware to the patient and to other hardware.

Overview

In cases where pectus carinatum or pectus excavatum require surgical correction, a common corrective procedure includes securing a pectus bar to a patient's chest wall to reshape and stabilize the chest wall. This procedure can include the steps of: creating opposing incisions on each side of a patient's chest wall; inserting a curved pectus bar into one incision; passing the pectus bar under the sternum; flipping the pectus bar; securing the pectus bar to the chest wall; securing a stabilizer to the pectus bar; securing the assembly to the chest wall; and, closing the incisions.

In some of these surgical procedures, incisions are located on an outer (lateral) portion of the chest wall for aesthetic purposes making it difficult for physicians to attach stabilizers to the pectus bar, to position the stabilizer at a desired location, and to secure the stabilizers to the pectus bar. The inventors have recognized, among other things, that a stabilizer can include a geometry for positioning the stabilizer anywhere along the pectus bar and including a locking mechanism that simplifies the process of securing the stabilizer to the pectus bar. These methods can shorten the surgical procedure and help reduce damage to components during the procedure, saving time and cost.

To further illustrate the apparatuses and systems disclosed herein, the following non-limiting examples are provided:

Example 1 is a pectus bar assembly comprising: a pectus bar comprising: a first portion comprising a first periphery; and a second portion opposite the first portion; and a stabilizer comprising: a stabilizer body comprising a recess engageable with the second portion; and a locking cam rotatable within the body to secure the stabilizer to the first portion.

In Example 2, the subject matter of Example 1 optionally includes wherein the recess is open to a second side of the body and wherein the locking cam is engageable at a first side of the body.

In Example 3, the subject matter of any one or more of Examples 1-2 optionally include wherein the recess is open to a first side of the body and wherein the locking cam is engageable at a first side of the body.

In Example 4, the subject matter of any one or more of Examples 1-3 optionally include the body further comprising: a cam bore intersecting the recess, the locking cam rotatable within the cam bore.

In Example 5, the subject matter of Example 4 optionally includes wherein: the cam bore further comprises a first notch; and wherein the locking cam comprises a tab that engages the first notch to restrict rotation of the locking cam within the cam bore, maintaining the locking cam in a locked position.

In Example 6, the subject matter of Example 5 optionally includes the cam bore further comprising: a second notch, wherein the tab engages the second notch to restrict rotation of the locking cam within the cam bore, maintaining the locking cam in a partially engaged position.

In Example 7, the subject matter of Example 6 optionally includes the cam bore further comprising: a third notch, wherein the tab engages the second notch to restrict rotation of the locking cam within the cam bore, maintaining the locking cam in an open position.

In Example 8, the subject matter of any one or more of Examples 5-7 optionally include the locking cam further comprising: an arm disposed proximate a periphery of the locking cam, the arm including the tab; and a living hinge supporting the arm, the living hinge flexible to enable the arm to move between an extended and a compressed position, where the tab engages the notch to lock the locking cam in the extended position, and the tab disengages the notch allowing the locking cam to rotate within the bore in the compressed position.

In Example 9, the subject matter of Example 8 optionally includes the bore further comprising: a ramped edge engageable with the notch to cause the arm to move to the compressed position allowing the locking cam to unlock from the cam bore and the pectus bar.

In Example 10, the subject matter of any one or more of Examples 5-9 optionally include the bore further comprising: a bore stop configured to engage the locking cam to set a rotational limit of the locking cam within the cam bore.

In Example 11, the subject matter of any one or more of Examples 5-10 optionally include wherein the first notch is disposed within the body and the arm internally engages the notch.

In Example 12, the subject matter of any one or more of Examples 1-11 optionally include wherein: the stabilizer further comprises a stabilizer shelf extending from the recess proximate the opening and towards the locking cam, the stabilizer shelf engageable with the second portion; and the locking cam further comprises a cam shelf engageable with the pectus bar.

In Example 13, the subject matter of any one or more of Examples 1-12 optionally include wherein the stabilizer is engageable with the pectus bar at any point along a length of the pectus bar.

In Example 14, the subject matter of any one or more of Examples 1-13 optionally include a first cam bore intersecting the recess, the locking cam rotatable within the first cam bore; a second cam bore intersecting the recess opposite the first cam bore; and a second locking cam rotatable within the second cam bore to engage the pectus bar.

In Example 15, the subject matter of any one or more of Examples 1-14 optionally include the locking cam further comprising: an exterior portion engageable with a tool and angled to be flush with the body of the stabilizer when the locking cam is in a locked position.

In Example 16, the subject matter of any one or more of Examples 11-15 optionally include the locking cam further comprising: a bar stop engageable with the pectus bar to limit rotation of the locking cam relative to the pectus bar.

Example 17 is a pectus bar stabilizer comprising: a body securable to a human chest wall; and a locking cam rotatable within the body operable to secure the stabilizer to a pectus bar.

In Example 18, the subject matter of Example 17 optionally includes the body further comprising a recess engageable with the pectus bar.

In Example 19, the subject matter of Example 18 optionally includes the body further comprising: a cam bore intersecting the recess, the locking cam rotatable within the cam bore.

In Example 20, the subject matter of any one or more of Examples 17-19 optionally include wherein: the cam bore further comprises a first notch; and wherein the locking cam comprises a tab that engages the first notch to restrict rotation of the locking cam within the cam bore, maintaining the locking cam in a locked position.

In Example 21, the subject matter of any one or more of Examples 17-20 optionally include the locking cam further comprising: an arm disposed proximate a periphery of the locking cam, the arm including the tab; and a living hinge supporting the arm, the living hinge flexible to enable the arm to move between an extended and a compressed position, where the tab engages the notch to lock the locking cam in the extended position, and the tab disengages the notch allowing the locking cam to rotate within the bore in the compressed position.

Example 22 is a method of securing a stabilizer to a pectus bar, the method comprising: placing a stabilizer over a pectus bar; and rotating a locking cam of the stabilizer to engage the pectus bar and secure the stabilizer to the pectus bar.

In Example 23, the subject matter of Example 22 optionally includes placing a stabilizer under a pectus bar; and rotating a locking cam of the stabilizer to engage the pectus bar and secure the stabilizer to the pectus bar.

Example 24 is a pectus bar comprising: a first portion comprising a first chamfer defining a first periphery of the first portion; a second portion opposite the first portion, the second portion comprising a second chamfer defining a second periphery of the second portion; and a radiused perimeter separating the first chamfer and the second chamfer.

In Example 25, the subject matter of Example 24 optionally includes a suture bore extending through the pectus bar proximate a first end of the pectus bar.

In Example 26, the subject matter of any one or more of Examples 24-25 optionally include wherein the pectus bar is pre-curved to match one of the anatomy of a patient and an anatomy of an average patient.

In Example 27, the subject matter of any one or more of Examples 24-26 optionally include wherein the first chamfer and second chamfer are configured to engage a stabilizer locking mechanism.

In Example 28, the subject matter of any one or more of Examples 24-27 optionally include wherein the pectus bar is symmetrical about one or more of a longitudinal plane, a transverse plane, and a frontal plane.

Example 29 is a pectus bar assembly comprising: a pectus bar comprising an elongate body having a first side and a second side; a stabilizer engageable with the pectus bar, the stabilizer comprising: a first portion engageable with the first side; and a second portion engageable with the second side and translatably couplable to the first portion.

In Example 30, the subject matter of Example 29 optionally includes wherein: the first portion further comprises a first shelf extending toward the second portion and engageable with the pectus bar; and the second portion further comprises a second shelf extending toward the first portion and engageable with the pectus bar.

In Example 31, the subject matter of any one or more of Examples 29-30 optionally include wherein: the first portion further comprises a first bore; and the second portion further comprises a second bore.

Example 32 is a pectus bar assembly comprising: a pectus bar comprising an elongate body having a first side and a second side; and a stabilizer engageable with the pectus bar, the stabilizer comprising: a first portion engageable with the first side; a second portion engageable with the second side; and a locking mechanism connecting the first portion to the second portion, the locking portion actuatable to secure the stabilizer to the pectus bar.

In Example 33, the subject matter of Example 32 optionally includes the locking mechanism further comprising: a first hinge coupling the first portion to the locking mechanism; and a second hinge coupling the second portion to the locking mechanism.

In Example 34, the subject matter of any one or more of Examples 32-33 optionally include wherein: the locking mechanism further comprises: a first post and a second post; the first portion further comprises a first locking fork releasably securable to the first post to secure the first portion to the pectus bar; and the second portion further comprises a second locking fork releasably securable to the second post to secure the second portion to the pectus bar.

In Example 35, the subject matter of any one or more of Examples 32-34 optionally include wherein: the first portion further comprises a first shelf extending toward the second portion and engageable with the pectus bar: and the second portion further comprises a second shelf extending toward the first portion and engageable with the pectus bar.

Example 36 is a pectus bar assembly comprising: a pectus bar comprising an elongate body having a first side and a second side; and a stabilizer engageable with the pectus bar, the stabilizer comprising: a first portion; a second portion opposite the first portion, the second portion comprising a recess configured to receive the pectus bar; and a shelf translatable into the recess to engage the pectus bar and secure the stabilizer relative to the pectus bar.

In Example 37, the subject matter of Example 36 optionally includes a drive rotatable to translate the shelf relative to the stabilizer to engage and disengage the pectus bar.

Example 38 is a pectus bar assembly comprising: a pectus bar comprising an elongate body having a first side and a second side, the first side comprising a groove; and a stabilizer engageable with the pectus bar, the stabilizer comprising a recess configured to engage the groove of the pectus bar.

In Example 39, the subject matter of Example 38 optionally includes wherein the stabilizer further comprises: a first portion and a second portion coupled by a living hinge and forming the recess opposite the living hinge.

In Example 40, the subject matter of any one or more of Examples 38-39 optionally include a fastener couplable to the first portion and the second portion to open and close the recess.

In Example 41, the subject matter of any one or more of Examples 38-40 optionally include wherein the pectus bar further comprises a second groove on the second side, and a second stabilizer engageable with the second groove.

Example 42 is a pectus bar assembly comprising: a pectus bar comprising an elongate body having a first side and a second side; a stabilizer engageable with the pectus bar, the stabilizer comprising: a first portion comprising a bore; a second portion opposite the first portion, the second portion comprising a recess configured to receive the pectus bar; and a fastener passing through the bore to engage the second portion and secure the pectus bar within the recess.

Example 43 is a pectus bar assembly comprising: a pectus bar comprising an elongate body; and a stabilizer engageable with the pectus bar, the stabilizer comprising: a first piece; and a second piece symmetrical to the first piece and couplable to the first piece to engage the pectus bar.

Example 44 is a pectus bar assembly comprising: a pectus bar comprising an elongate body having a first side and a second side and a slot extending through the body; a stabilizer engageable with the pectus bar, the stabilizer comprising: a recess configured to receive the pectus bar; and a fastener passing through and engaging the slot and securable to the stabilizer recess to releasably couple the stabilizer to the pectus bar.

In Example 45, the subject matter of Example 44 optionally includes wherein the stabilizer further comprises: ramps surrounding the recess.

In Example 46, the subject matter of any one or more of Examples 44-45 optionally include wherein the slot comprises internal threading configured to couple to a fastener at any position within the slot.

Example 47 is a pectus bar assembly comprising: a pectus bar comprising an elongate body; and a stabilizer engageable with the pectus bar, the stabilizer comprising: a recess configured to receive the pectus bar; and a bore extending through the body and intersecting with the recess; and a fastener passing through the bore and engageable with the pectus bar.

Example 48 is a pectus bar assembly comprising: a pectus bar comprising an elongate body having a first side and a second side; and a stabilizer engageable with the pectus bar, the stabilizer comprising: a first portion engageable with the first side; a second portion coupled to the first portion and translatable between an open and a closed position, the second portion engaging the second side in the closed position; and a retaining member connecting the first portion to the second portion and configured to translate the second portion between the open and the closed positions.

Example 49 is a pectus bar assembly comprising: a pectus bar comprising an elongate body having a first side and a second side; and a stabilizer comprising: a first portion engageable with a first side of the pectus bar; a second portion rotatably coupled to the first portion, rotatable between an open and a closed position, and engageable with a second side of the pectus bar in the closed position.

In Example 50, the subject matter of Example 49 optionally includes wherein: the first portion comprises a notch; and the second portion comprises a tab, engageable with the notch to prevent rotation of the second portion relative to the first portion when the second portion is in the closed position.

In Example 51, the subject matter of Example 50 optionally includes wherein the second portion further comprises: a shelf rotatable with the second portion to engage the pectus bar when the second portion is in the locked position.

Example 52 is a pectus bar assembly comprising: a pectus bar comprising an elongate body having a first side and a second side; and a stabilizer engageable with the pectus bar, the stabilizer comprising: a first portion engageable with the first side; and a second portion coupled to the first portion and translatable between an open and a closed position, the second portion engaging the second side in the closed position.

In Example 53, the subject matter of Example 52 optionally includes wherein the first portion further comprises: a first shelf translatable engageable with the pectus bar.

In Example 54, the subject matter of Example 53 optionally includes wherein the second portion further comprises: a second shelf translatable with the second portion to engage the pectus bar when the second portion is in the locked position.

In Example 55, the subject matter of any one or more of Examples 52-54 optionally include wherein: the first portion further comprises a first protrusion extending substantially towards the second portion; and the second portion further comprises a second protrusion and a third protrusions each extending substantially towards the first portion, the second protrusion and third protrusion each engaging the first protrusion to restrict rotation of the second portion relative to the first portion.

In Example 56, the subject matter of Example 55 optionally includes wherein: the first portion further comprises a first bore extending through the first protrusion; the second portion further comprises a second bore extending through the second protrusion, the second bore alignable with the first bore when the second portion is in the closed position; and a fastener translatable within the first bore and extendable into the second bore to align the second bore with the first bore and to secure the second portion in the closed position.

In Example 57, the subject matter of Example 56 optionally includes wherein: the second bore further comprises an undercut configured to receive the fastener when the second portion is in the closed position.

In Example 58, the subject matter of Example 57 optionally includes wherein: the second bore further comprises chamfer at a connection between a minor diameter of the second bore and the undercut, the chamfer forcing the second portion to align with the first portion as the fastener translates into the minor diameter from the undercut.

In Example 59, the subject matter of Example 58 optionally includes wherein: the fastener is tapered at a termination, the taper engageable with the chamfer to force the second portion to align with the first portion as the fastener translates into the minor diameter from the undercut.

In Example 60, the subject matter of Example 59 optionally includes wherein: the fastener is threaded; and the first bore is threaded to receive the fastener.

In Example 61, the subject matter of Example 60 optionally includes wherein: the first portion further comprises a pin traversing the first bore to limit translation of the fastener relative to the first bore.

In Example 62, the apparatuses or method of any one or any combination of Examples 1-62 can optionally be configured such that all elements or options recited are available to use or select from.

These and other examples and features of the present apparatuses and systems will be set forth in part in the following Detailed Description. This Overview is intended to provide non-limiting examples of the present subject matter and it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices and systems for chest wall correction procedures. For example, the present application discloses an assembly for coupling a pectus bar and stabilizers to a chest wall of a patient to correct pectus excavatum or pectus carinatum.

Figure 1:
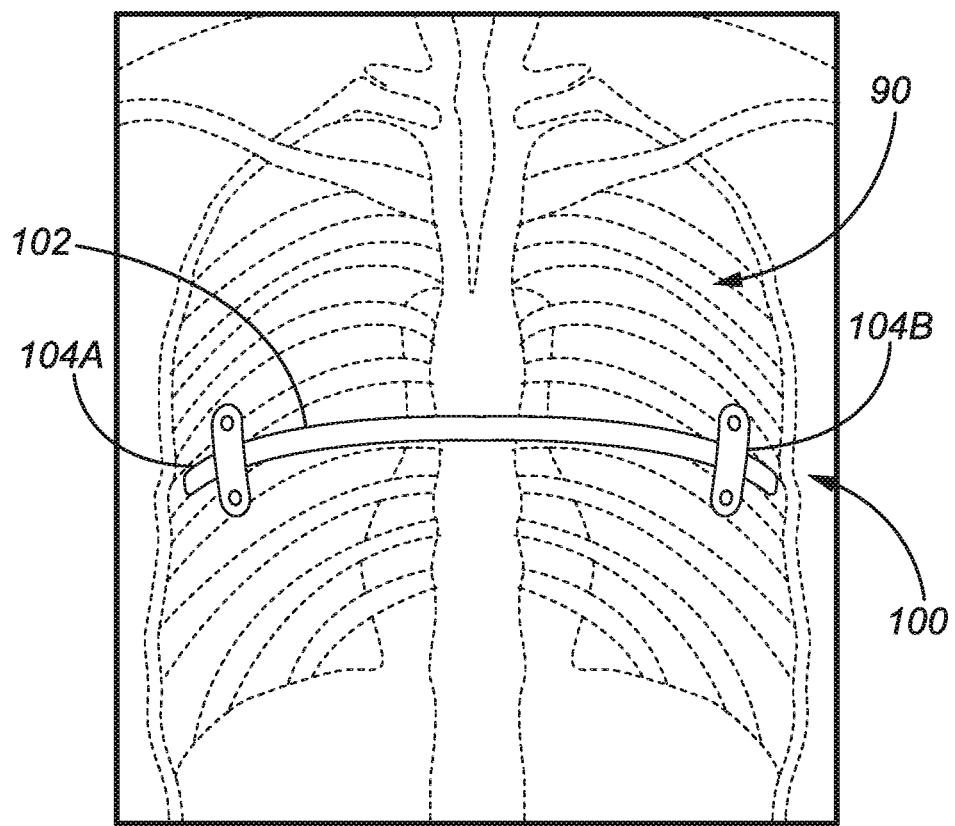
FIG. 1 illustrates an X-ray image of a pectus bar assembly installed in a chest wall of a patient, in accordance with at least one example of the present disclosure.

FIG. 1 illustrates an X-ray image of pectus bar assembly 100, which can include pectus bar 102 and stabilizers 104A and 104B. Pectus bar 102 can include bar bores (not shown in FIG. 1). Also shown in FIG. 1 is chest wall 90, which includes ribs and costal tissues, such as cartilage.

Pectus bar 102 can be a rigid or semi-rigid bar constructed of materials such as metals and plastics. Pectus bar 102 can have an elongate body forming a curve, such as a c-shape, in some examples. Bar bores can be disposed near the terminations of pectus bar 102 and can be configured to receive fasteners, such as flexible or wire sutures, in some examples, to secure pectus bar 102 to ribs and/or soft tissues of chest wall 90. In some examples, pectus bar 102 can include one bar bore, and in other examples, pectus bar 102 can include two, three, four, or more bar bores.

Stabilizers 104A and 104B can be a rigid or semi-rigid components constructed of materials such as metals and plastics. Stabilizers 104A and 104B and pectus bar 102 can be configured to receive coatings to improve the characteristics of the bar, such as strength and coefficient of friction, which can improve a process of passing the bar through chest wall and soft tissues. Other coatings can be applied to stabilizers 104A and 104B and pectus bar 102, in some examples, to reduce nickel sensitivity. In some examples, stabilizers 104A and 104B and pectus bar 102 can have a highly finished surface, such as a polished surface, to reduce friction of stabilizers 104A and 104B and pectus bar 102, and to minimize bonding of stabilizers 104A and 104B and pectus bar 102 to tissue. Reduced bonding can accommodate removability of stabilizers 104A and 104B and pectus bar 102 in a follow-up procedure to remove the stabilizers after the period required to correct the deformity.

Stabilizers 104A and 104B can be configured to engage and secure to pectus bar 102 anywhere along the length of pectus bar 102. Stabilizers 104A and 104B can also include bores (discussed later) that can be used to secure stabilizer 104 to ribs and/or soft tissues of chest wall 90. Stabilizers 104A and 104B can also include a locking mechanism (shown and discussed below) that can be used to secure stabilizers 104A and 104B to pectus bar 102.

In operation of some examples, a procedure to correct pectus excavatum or pectus carinatum can include creating opposing incisions on each side of a patient's chest wall and inserting pectus bar 102 into one incision. Pectus bar 102 can then be passed under the sternum of the patient and flipped into a final position. Thereafter, stabilizers 104A and 104B can be inserted into the incision or incisions and secured to pectus bar 102 and to chest wall 90 of the patient before final preparations are made and incisions are closed. In some procedures, only one stabilizer can be used.

During this process, a physician can position stabilizers 104A and 104B along the length of the bar, as desired. However, in some procedures, because of the lateral placement of incisions and because of a sometimes desired medial position of stabilizers 104A and 104B, placement of stabilizers 104A and 104B and securing of stabilizers 104A and 104B onto pectus bar 102 may be difficult. In such cases, an integral locking mechanism may simplify the process of securing stabilizers 104A and 104B to pectus bar 102 and can improve a procedure for making adjustments that may be required throughout the procedure.

Figure 2:
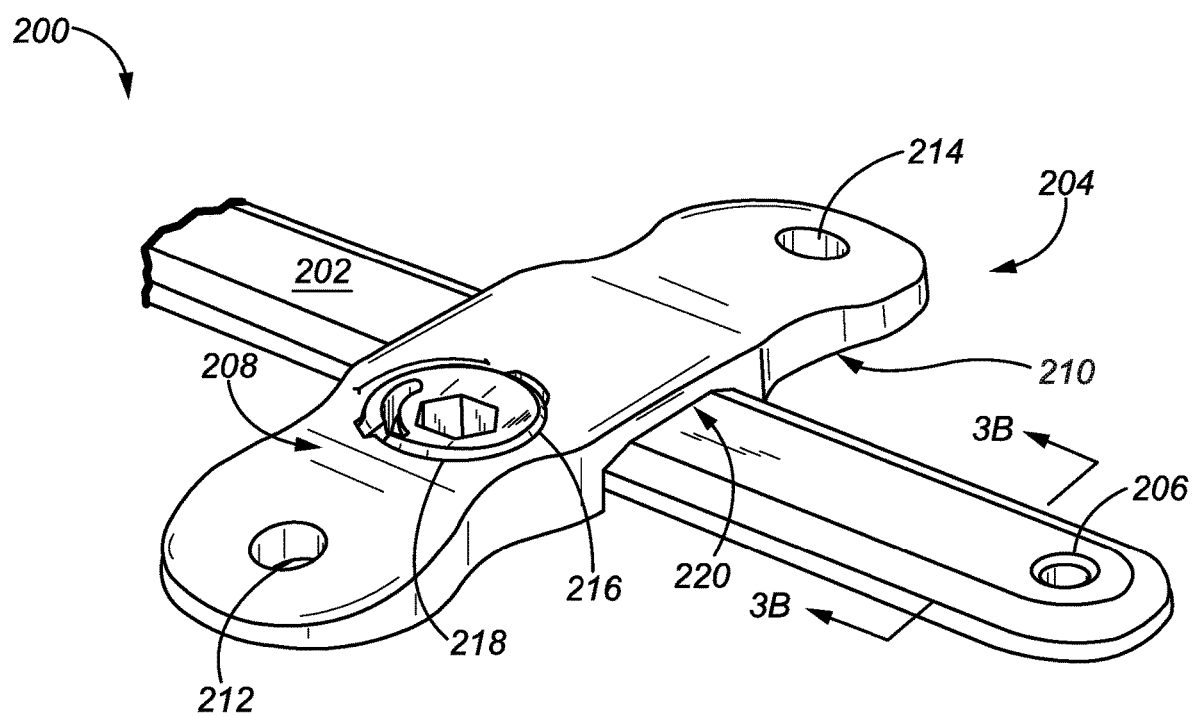
FIG. 2 illustrates a top isometric view of a pectus bar assembly, in accordance with at least one example of the present disclosure.

FIG. 2 illustrates a top isometric view of pectus bar assembly 200, which can include pectus bar 202 (only a portion of pectus bar 202 is shown in FIG. 2), and stabilizer 204. Pectus bar 202 can include bar bores 206 (only one shown in FIG. 2). Stabilizer 204 can include first portion 208, second portion 210, stabilizer bores 212 and 214, locking cam 216, cam bore 218, and recessed portion 220. Also shown in FIG. 2 are section arrows 3B and 3B.

Pectus bar assembly 200 can be connected and can operate consistently with pectus bar assembly 100. However, pectus bar assembly 200 illustrates further details.

Pectus bar 202 can be a rigid or semi-rigid bar constructed of materials such as metals and plastics, and can form a curve, such as a c-shape, as described above. Bar bores 206 can be disposed near the terminations of pectus bar 202 and can be configured to receive fasteners, such as flexible sutures and wire sutures, in some examples, to secure pectus bar 202 to a chest wall. Bar bores 206 can be smooth to reduce irritation of adjacent tissue and to reduce wear on fasteners, such as sutures, passing through bar bores 206. Stabilizer 204 can be a rigid or semi-rigid component comprised of biocompatible materials such as stainless steel alloys, titanium alloys, cobalt-chromium alloys, and the like. Stabilizer 204 can be configured to engage pectus bar 202 via top, bottom, and end positions of pectus bar 202, and can be configured to secure to pectus bar 202 anywhere along the length of pectus bar 202, as desired.

Stabilizer 204 can include stabilizer bores 212 and 214, each spaced away from recessed portion 220 and each extending through a body of stabilizer 204. Stabilizer bores 212 and 214 can be configured to receive fasteners, such as flexible sutures and wire sutures, in some examples, and can be smooth to reduce irritation of adjacent tissue and to reduce wear on fasteners, such as sutures, passing through stabilizer bores 212 and 214. First portion (or first side) 208 of stabilizer 204 can be opposite second portion (or second side) 210. First portion 208 and second portion 210 can form a body of stabilizer 204.

Cam bore 218 can extend from first portion 208 into stabilizer 204 and can terminate prior to extending through stabilizer 204. Cam bore 208 can intersect partially with recessed portion 220. Cam bore 218 can be sized to receive locking cam 216, which can be rotatable within cam bore 218 to engage and disengage pectus bar 202.

Recessed portion 220 can be a recess that is open at second portion 210 of stabilizer 204, or a bottom of stabilizer 204. Recessed portion 220 can be sized and shaped to receive pectus bar 202. In other words, stabilizer 204 is top-mounted to pectus bar 202. In some other examples, recessed portion 220 can be open to first portion 210, or bottom-mounted. As discussed below in FIG. 3, locking cam 216 can be rotatable to engage pectus bar 202 at recessed portion 220 to lock stabilizer 204 to pectus bar 202.

In operation of some examples, a procedure to correct pectus excavatum or pectus carinatum can include inserting pectus bar 202 into a chest wall of a patient, as described above, where bar bores 206 can be used to secure pectus bar 202 to the chest wall with sutures, and the like. During this process, a physician can position stabilizer 204 along the length of pectus bar 202, as desired, by engaging recess 220 with pectus bar 202 when cam lock 216 is in an open position. Once stabilizer 204 is positioned in a desired location on pectus bar 202, cam lock 216 can be rotated to engage pectus bar 202 and secure cam lock 216, and therefore stabilizer 204, to pectus bar 202. Thereafter, stabilizer bores 212 and 214 can be used to secure stabilizer 204 to the chest wall with sutures and the like.

Pectus bar assembly 200 thus enables a physician to relatively quickly place and secure stabilizer 204 on pectus bar 202 and secure stabilizer 202. Stabilizer 204 can therefore increase procedural efficiency, which can save time and cost. Also, because pectus bar assembly 200 can enable medial placement of stabilizer 204 on pectus bar 202, pectus bar assembly 200 can provide improved stabilization of the pectus bar by reducing moments and forces applied to stabilizer 204 by pectus bar 202.

In some examples of prior art, some stabilizer and pectus bar assemblies require side mounting of the stabilizer to the bar, making medial placement of a stabilizer more difficult. The present disclosure addresses this issue by using recessed portion 220 and locking cam 216, which allow for stabilizer 204 to be placed onto pectus bar 202 from a top side, from an under side, or from an end. This flexibility can increase procedural efficiency of placement of stabilizer 204 onto pectus bar 202.

Figure 3A:
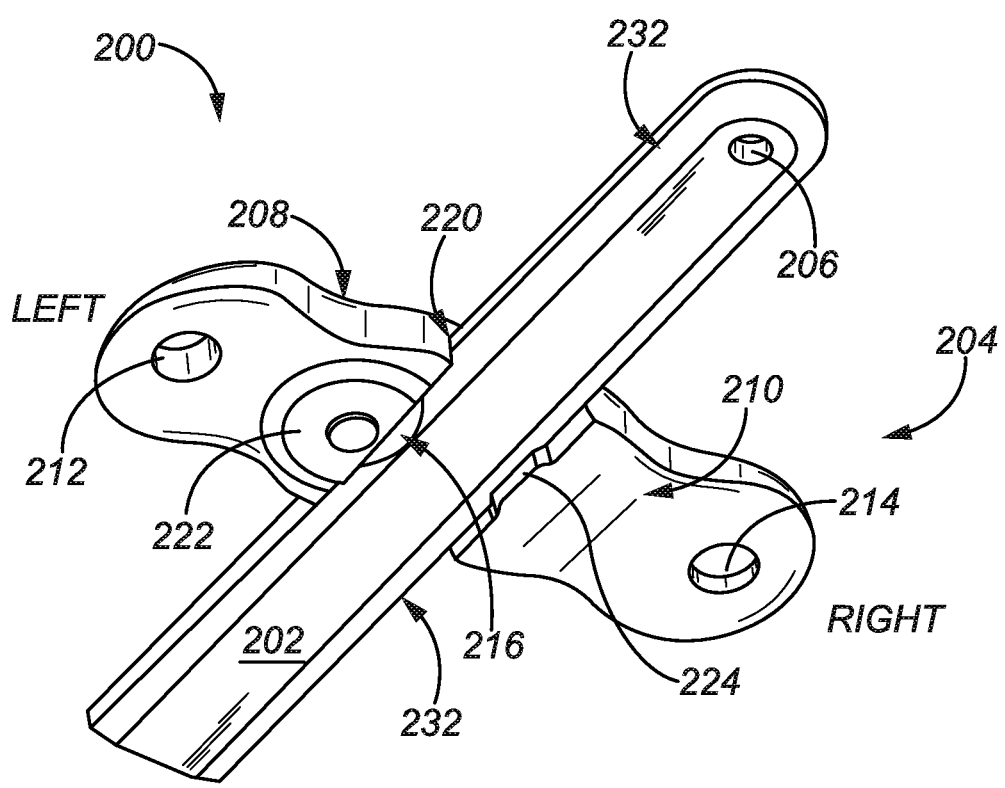
FIG. 3A illustrates a bottom isometric view of a pectus bar assembly, in accordance with at least one example of the present disclosure.
Figure 3B:
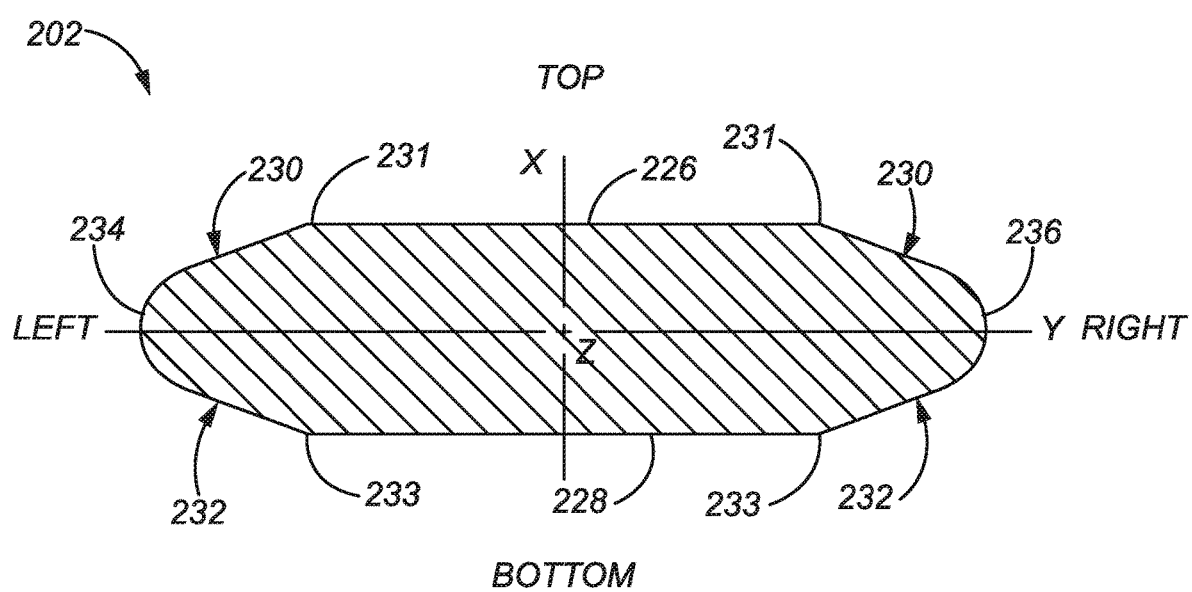
FIG. 3B illustrates a cross-sectional view of a pectus bar, in accordance with at least one example of the present disclosure.

FIG. 3A illustrates a bottom isometric view of pectus bar assembly 200. FIG. 3B illustrates a cross-sectional view of pectus bar 202 across section 3B-3B of FIG. 2. FIGS. 3A and 3B are discussed below concurrently.

Pectus bar assembly 200 can include pectus bar 202 (only a portion of pectus bar 202 is shown in FIG. 3A), and stabilizer 204. Pectus bar 202 can include bar bores 206 (only one shown in FIG. 3A). As shown in FIG. 3A, stabilizer 204 can include first portion 208, second portion 210, stabilizer bores 212 and 214, locking cam 216, recessed portion 220, cam bore protuberance 222, and shelf 224.

As shown in FIG. 3B, pectus bar 202 can include top side 226, bottom side 228, top chamfer 230, bottom chamfer 232, left edge 234, and right edge 236. Also shown in FIG. 3B are orientation indicators Top, Bottom, Left, and Right, X-axis, Y-axis, and Z-axis (into the page). In some examples, left edge 234 and adjacent chamfers can be considered a first portion of the pectus bar, and right edge 236 and adjacent chamfers can be considered a second portion of the pectus bar.

Pectus bar 202 can be a rigid or semi-rigid bar having an elongate body and being constructed of biocompatible materials such as metals and plastics, for example, stainless steel alloys, titanium alloys, cobalt-chromium alloys, and the like. As shown in FIG. 3B, pectus bar 202 can have a generally flat profile with two opposing sides, top side 226 and bottom side 228 that can be substantially flat. Top side 226 can include chamfer 230 that extends around a perimeter of top side 226. Bottom side 228 can include chamfer 232 that extends around a perimeter of bottom side 228. Chamfers 230 and 232 can meet to form a perimeter edge, shown in FIG. 3B as left edge 234 and right edge 236. However, left edge 234 and right edge 236 may be continuous around a perimeter of pectus bar 202, in some examples. Accordingly, pectus bar 202 can be symmetrical about the X-axis, Y-axis, and Z-axis, prior to being bent. Though pectus bar 202 is shown as symmetrical, pectus bar 202 can be asymmetrical about the X-axis, Y-axis, and Z-axis in other examples.

After being bent, pectus bar 202 can form a curve, such as a c-shape, in some examples. In some examples, pectus bar 202 can be pre-bent to match a chest wall anatomy specific to a patient. In some examples, pectus bar 202 can be bent during a procedure to match a patient-specific anatomy. In some other examples, pectus bar 202 can include a generic pre-bend based on a best fit for an average patient or patient type.

Left edge 234 and right edge 236 can be radiused or eased, as shown in FIG. 3B. This can increase the maneuverability of pectus bar 202 through a chest wall of a patient as pectus bar 202 is woven through the chest wall. Edge 231 at the connection between top chamfer 230 and top side 236 and edge 233 between bottom chamfer 242 and bottom side 228 can have a small radius, which can prevent sharp edges, improving physician handling and patient comfort by reducing palpability, in some examples. Top chamfer 230 and bottom chamfer 232 also reduce the probability of pectus bar 202 catching on soft tissues of the patient as pectus bar is inserted into position and flipped within the chest wall. Further, the large radiuses of left edge 234 and right edge 236 can reduce localized pressure within a chest wall and can reduce sharp edges to reduce cutting or damage of tissue adjacent to pectus bar 202 when installed.

As shown in FIG. 3A, stabilizer 204 can include shelf 224 that extends from a bottom portion of recess 220 towards locking cam 216. Similarly, locking cam 216 can protrude from cam bore 218 (FIG. 2) and from cam protuberance 222 to extend towards shelf 224. Each of locking cam 216 and shelf 224 can engage a chamfer of pectus bar 202, such as bottom chamfer 232, as shown in FIG. 3A. When pectus bar 202 resides in recess 220 and both locking cam 216 and shelf 224 engage chamfer 232, pectus bar 202 cannot be removed from stabilizer 204.

Alternatively, when locking cam 216 is not engaging bottom chamfer 232 of pectus bar 202, stabilizer 204 can move relative to pectus bar 202, but can only be translated along pectus bar 202 unless a left portion of stabilizer 204 is tilted upward from pectus bar 202. When tilted, shelf 224 can be disengaged from pectus bar 202 by moving stabilizer 204 to the right. In reverse (or when installing stabilizer 204 onto pectus bar 202), when locking cam 216 is in an open position, stabilizer 204 can be tilted and placed over pectus bar 202. That is, pectus bar 202 must be hooked onto shelf 224 to be positioned into recess 220 of stabilizer 204.

In some examples, shelf 224 can have a width shorter than a width of stabilizer 204, as shown in FIG. 3A. The reduced width of shelf 224 can allow securing to curved portions of pectus bar 202 and can allow for sliding or gliding of stabilizer 204 along curved portions of pectus bar 202.

Once stabilizer 204 is positioned on pectus bar 202, locking cam 216 can be rotated to engage bottom chamfer 232, securing locking cam 216 and shelf 224 to chamfer 232 and thereby locking stabilizer 204 to pectus bar 202. In this way, stabilizer 204 can be quickly and easily locked to and unlocked from pectus bar 202, which can increase surgical efficiency.

Figure 4:
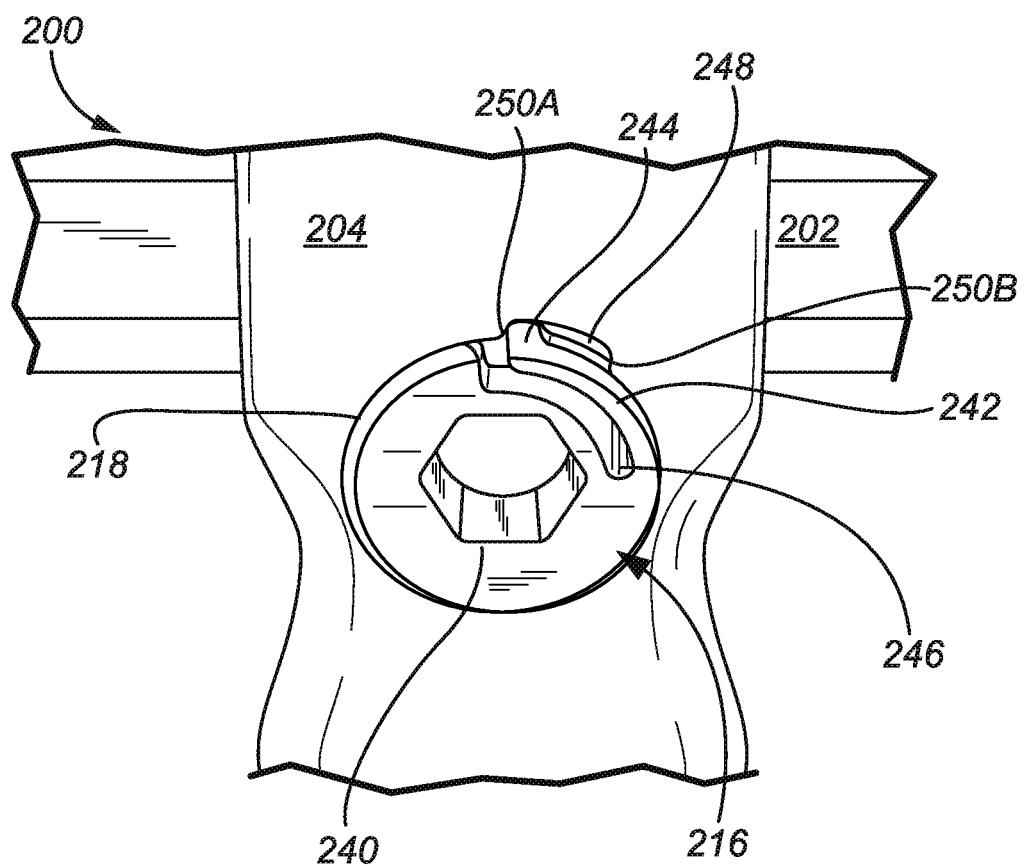
FIG. 4 illustrates an isometric view of a portion of a pectus bar assembly, in accordance with at least one example of the present disclosure.
Figure 5:
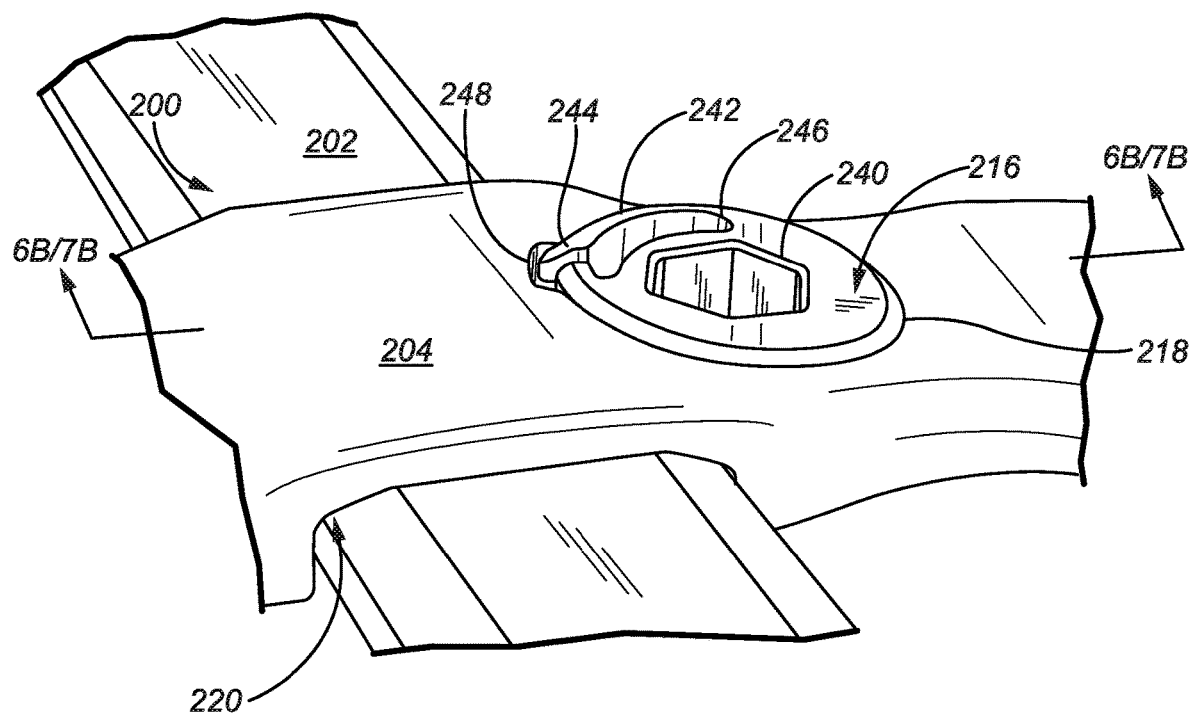
FIG. 5 illustrates an isometric view of a portion of a pectus bar assembly, in accordance with at least one example of the present disclosure.

FIG. 4 illustrates an isometric view of a portion of pectus bar assembly 200. FIG. 5 illustrates an isometric view of a portion of pectus bar assembly 200. FIGS. 4 and 5 are discussed below concurrently.

Pectus bar assembly 200 can include pectus bar 202 (only a portion of pectus bar 202 is shown in FIGS. 4 and 5), and stabilizer 204. Stabilizer 204 can include first portion 208, locking cam 216, and recessed portion 220 (shown in FIG. 5). Locking cam can include tool interface 240, arm 242, tab 244, and living hinge 224. Cam bore 218 can include notch 248, which can include ramps 250A and 250B. Also shown in FIG. 5 are section arrows 6B/7B.

The components of pectus bar assembly 200 can be consistent with those shown in FIGS. 2-3, however, FIGS. 4 and 5 show additional details of locking cam 216 and cam bore 218. For example, locking cam 216 can include tool interface 240, which can be a hex interface in some examples, and can be a star, slotted (standard), cross-slotted, and the like, in other examples. Tool interface 240 can be configured to receive a driver for transferring torque from the driver to locking cam 216, in some examples.

Locking cam 216 can also include arm 242 that extends from living hinge 224 at a periphery of locking cam 216. Tab 244 can be disposed proximate a termination of arm 242, where tab 244 can extend radially beyond the diameter of locking cam 216. Tab 244 can have a substantially trapezoidal protuberance. That is, the radial extensions are not parallel and the outer surface of tab 244 is circumferentially smaller than a distance between points where radial extensions connect to arm 242.

Arm 242 can be spaced away from the remainder (or body) of locking cam 216, such that living hinge 224 can allow arm 242 to flex or move radially relative to the body of locking cam 216.

Slot 248 of cam bore can be diametrically sized to receive tab 244, but can have a circumferential length that is larger than a circumferential length of tab 244, in some examples.

Slot 248 can also include ramps 250A and 250B, which can be complementary to the sides or radial extensions of tab 244.

In operation of one example, locking cam 216 can be rotatable within locking bore 218, for example by a hex tool engaging tool interface 240. When tab 244 engages cam bore 218, arm 242 can flex radially inward via living hinge 224, allowing locking cam 216 to rotate freely within cam bore 218. When tab 244 reaches slot 248, arm 242 can extend via living hinge 224 so that tab 244 engages slot 248. When tab 244 is engaged within slot 248, rotation of locking cam 216 within cam bore 218 is limited by contact between tab 244 and ramps 250A and 250B. Tab 244 may spring or snap outward when tab 244 reaches slot 248, which can provide tactile and audible feedback to a physician that locking cam 216 is in a locked position.

Because of the angled complimentary shapes of tab 244 and ramps 250A and 250B, a torque may be applied to locking cam 216 when tab 244 is in slot 248 (when locking cam 216 is in a locked position) that causes either of ramps 250A and 250B to force tab 244 and therefore arm 242 radially inward, allowing locking cam to rotate within cam bore 218. In this way, tab 244 and slot 248 provide a reversible locking mechanism that can prevent accidental unlocking while stabilizer 204 is secured to pectus bar 202, but can allow stabilizer 204 to be quickly and easily unlocked from pectus bar 202 when desired. The reversibility of locking cam 216 can be useful for repositioning a stabilizer during a surgery to correct pectus excavatum or pectus carinatum, and can be useful when removing a pectus bar assembly at a follow-up procedure or revision.

Figure 6A:
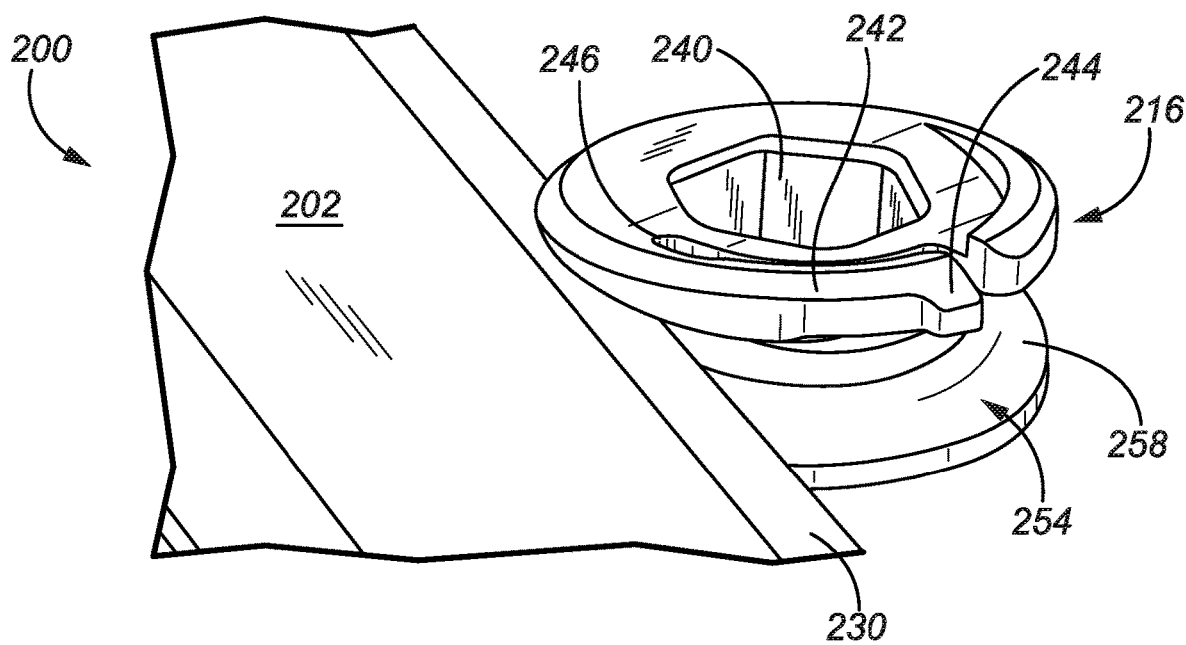
FIG. 6A illustrates an isometric view of a pectus bar assembly, in accordance with at least one example of the present disclosure.
Figure 6B:
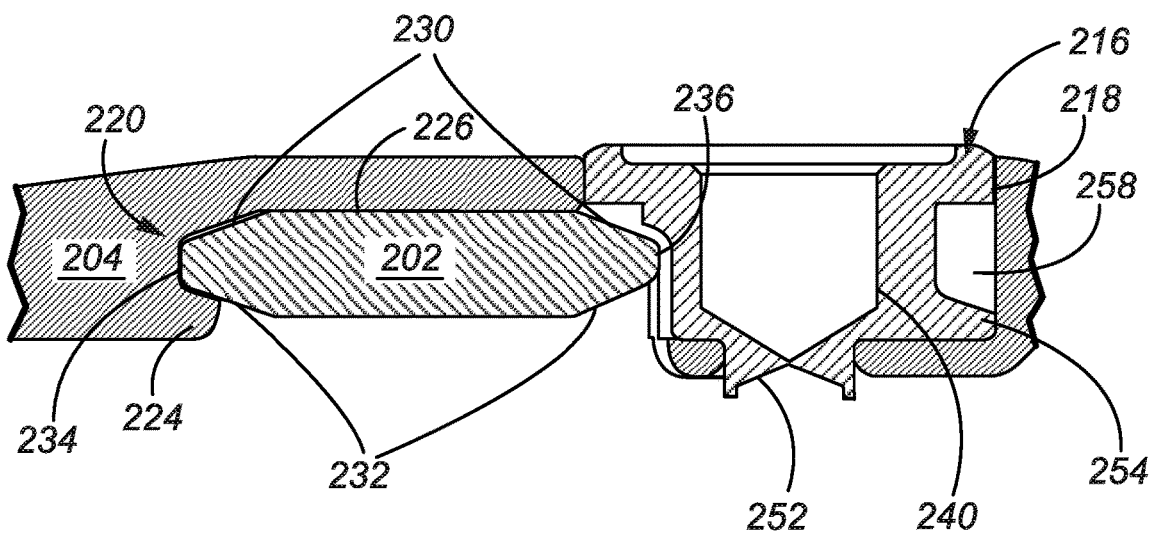
FIG. 6B illustrates an isometric view of a pectus bar assembly, in accordance with at least one example of the present disclosure.
Figure 7A:
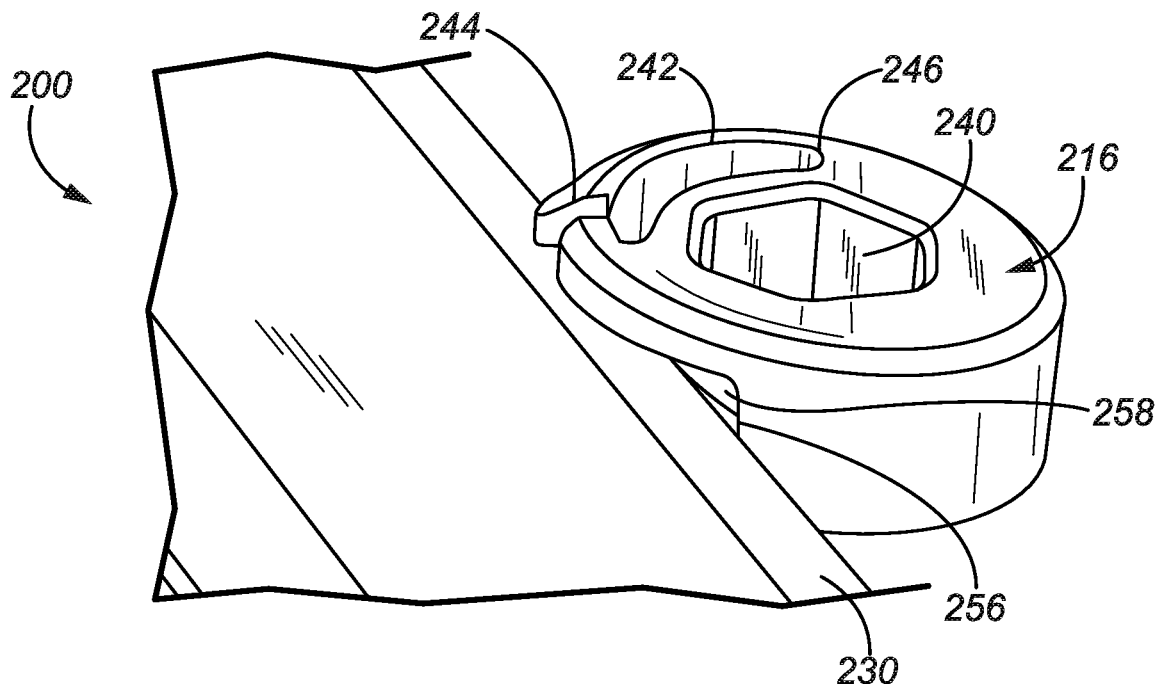
FIG. 7A illustrates an isometric view of a pectus bar assembly, in accordance with at least one example of the present disclosure.
Figure 7B:
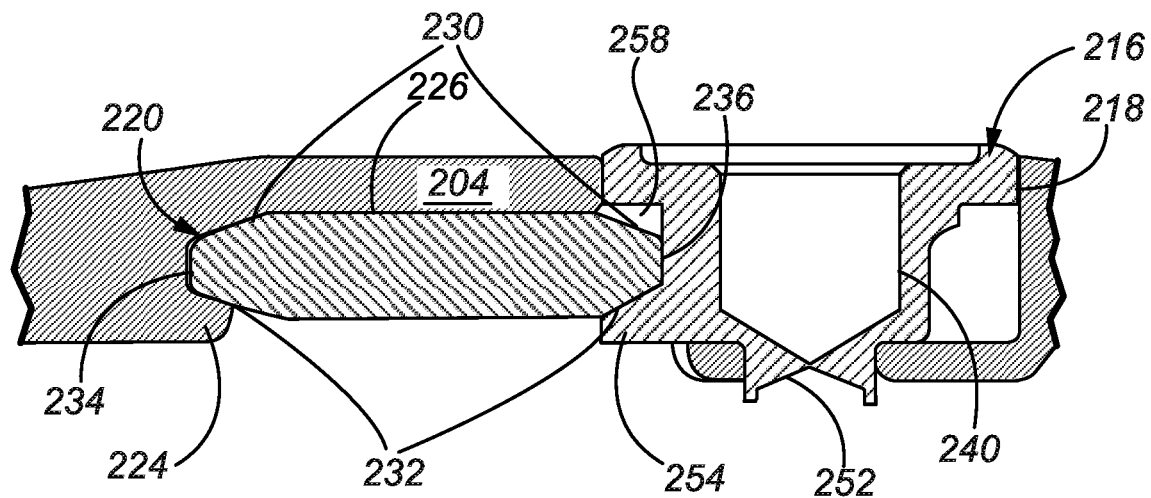
FIG. 7B illustrates a cross-section view of a pectus bar assembly, in accordance with at least one example of the present disclosure.

FIG. 6A illustrates an isometric view of pectus bar assembly 200 with stabilizer 204 removed and with locking cam 216 in an unlocked position. FIG. 6B illustrates a cross-section view of pectus bar assembly 200 along section 6B-6B of FIG. 5 with locking cam 216 in an unlocked position. FIG. 7A illustrates an isometric view of pectus bar assembly 200 with stabilizer 204 removed and with locking cam 216 in a locked position. FIG. 7B illustrates a cross-section view of pectus bar assembly 200 along section 7B-7B of FIG. 5 with locking cam 216 in a locked position. FIGS. 6A, 6B, 7A, and 7B are discussed below concurrently.

Pectus bar assembly 200 can include pectus bar 202 (only a portion of pectus bar 202 is shown in FIGS. 6A and 7A), and stabilizer 204 (not shown in FIGS. 6A and 7A). Pectus bar 202 can include top side 226, top chamfer 230, bottom chamfer 232, left edge 234, and right edge 236. Stabilizer 204 can include locking cam 216 and recessed portion 220 (shown in FIG. 5). Locking cam 216 can include tool interface 240, arm 242, tab 244, living hinge 224, bottom bore 252, cam shelf 254, and bar stop 256 (shown in FIG. 7A).

Pectus bar assembly 200, as shown in FIGS. 6A, 6B, 7A, and 7B, can be connected and can operate consistently with the description of FIGS. 1-5 above. However, FIGS. 6A, 6B, 7A, and 7B show further details of pectus bar assembly 200. For example, FIGS. 6B and 7B show how recess 220 and shelf 224 of stabilizer 204 can engage pectus bar 202. As shown in FIGS. 6B and 7B, once pectus bar 202 engages shelf 224 and recess 220 of stabilizer 204, stabilizer 204 contacts top side 226, upper chamfer 230, left edge 234, and lower chamfer 232. By contacting many surfaces of pectus bar 202, stabilizer 204 can form a secure engagement with pectus bar 202.

Also, as shown in FIGS. 7A and 7B is how locking cam 216 can engage pectus bar 202. More specifically, shelf 254 of locking cam 216 can extend radially from a body of cam 216, formed by recess 258 of locking cam 216. Recess 258 can be an asymmetric undercut of locking cam 216, where shelf 254 extends from a lower portion of recess 258. In an unlocked position (as shown in FIG. 6B), shelf 254 can reside within cam bore 218. In a locked position (as shown in FIG. 7B), shelf 254 can engage lower chamfer 232 of pectus bar 202. Because shelf 254 is angled upwards and complementary to chamfer 232, shelf 254 can force pectus bar 202 upwards as locking cam 216 is rotated, so that shelf 254 contacts pectus bar 202. Additionally, the body of locking cam 216 can engage right edge 236 of pectus bar 202 forcing pectus bar left and against stabilizer 204. In this way, locking cam 216 can restrain movement of pectus bar 202 when locking cam 216 is in a locked position.

Shown in FIG. 7A is bar stop 256, which can be a tangential wall of the body of locking cam 216 that partially forms recess 258 and shelf 254 of locking cam 216. Bar stop 256 can contact pectus bar 202 (as shown in FIG. 7A) when locking cam 216 is rotated to a fully locked position. Contact between bar stop 256 of locking cam 216 and pectus bar 202 can prevent over-rotation of locking cam 216 within bore 218 and can therefore prevent accidental or undesired unlocking of locking cam 216 from pectus bar 202. Also, contact between bar stop 256 and pectus bar 202 can provide tactile feedback to a physician indicating that locking cam 216 is in a fully locked position.

Bore 252 of locking cam 216 can be a bore extending from a bottom portion of locking cam 216 inward toward tool interface 240 and stopping prior to reaching the bore of tool interface 240. During manufacturing, bore 252 can be deformed (such as flared) to retain locking cam 216 within stabilizer 204.

Figure 8A:
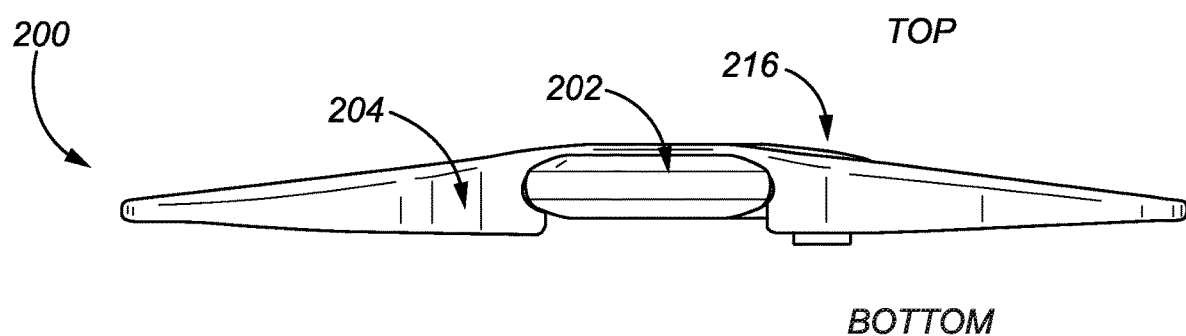
FIG. 8A illustrates a side isometric view of a pectus bar assembly, in accordance with at least one example of the present disclosure.
Figure 8B:
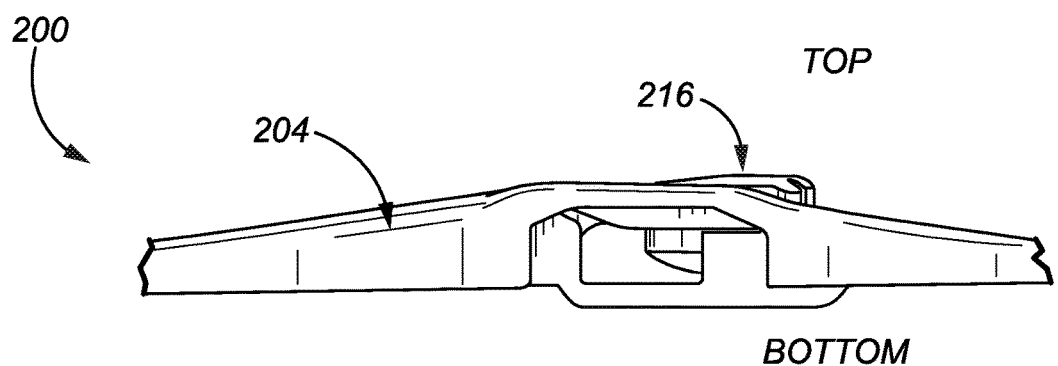
FIG. 8B illustrates a side isometric view of a pectus bar assembly, in accordance with at least one example of the present disclosure.

FIG. 8A illustrates a side isometric view of pectus bar assembly 200 in a locked position. FIG. 8B illustrates a side isometric view of pectus bar assembly 200 in an unlocked position. Pectus bar assembly can be consistent with that of FIGS. 1-7B. FIGS. 8A and 8B further illustrate how locking cam 216 can have an angled profile so that locking cam 216 is substantially flush with a top surface of stabilizer 204 when locking cam 216 is in a locked position, as shown in FIG. 8A. Consequently, when locking cam 216 is in an unlocked position, as shown in FIG. 8B, locking cam 216 may not be flush with a top surface of stabilizer 204.

Figure 9:
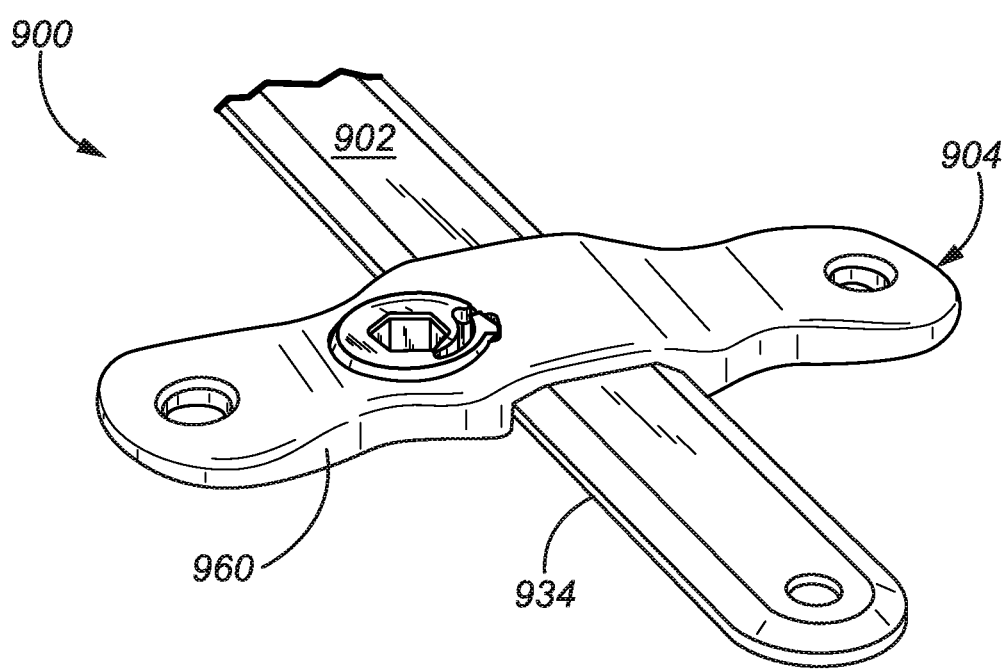
FIG. 9 illustrates an isometric view of a pectus bar assembly, in accordance with at least one example of the present disclosure.

FIG. 9 illustrates an isometric view of pectus bar assembly 900, which can include pectus bar 902 (only a portion of pectus bar 292 is shown in FIG. 9) and stabilizer 904. Pectus bar 902 can include left edge 934 and stabilizer 904 can include contouring 960.

Pectus bar assembly 900 can be connected and can operate similarly to pectus bar assemblies 100 and 200 discussed above. However, pectus bar assembly 900 can differ in that left edge 934 (and a right edge not visible in FIG. 9) can include a small radius and/or a small thickness. This can improve securing of stabilizer 904 to pectus bar 902, in some examples.

Also shown in FIG. 9 is contouring 960 of stabilizer 904. Contouring 960 of edges of stabilizer 904 can reduce friction between stabilizer 904 and soft tissues and ribs during insertion of stabilizer 904 into a chest wall. Contouring 960 can also reduce palpability of stabilizer 904 and can increase patient comfort.

Figure 10:
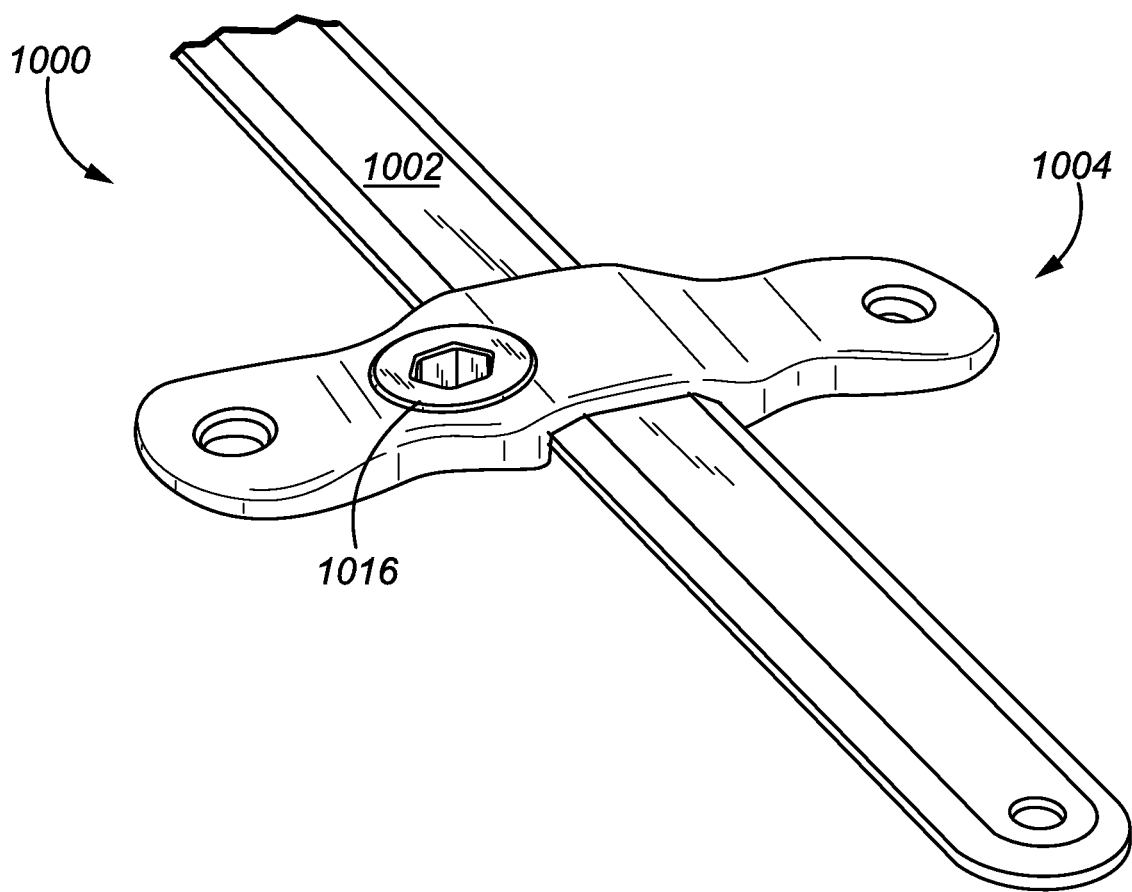
FIG. 10 illustrates an isometric view of a pectus bar assembly, in accordance with at least one example of the present disclosure.

FIG. 10 illustrates an isometric view of pectus bar assembly 1000, which can include pectus bar 1002 (only a portion of pectus bar 1002 is shown in FIG. 10) and stabilizer 1004. Stabilizer 1004 can include contouring locking cam 1016.

Pectus bar assembly 1000 can be connected and can operate similarly to pectus bar assemblies 100, 200, and 900 discussed above. However, pectus bar assembly 1000 can differ in that locking components of locking cam 1016, such as a tab, arm, and hinge, can be disposed within stabilizer 1004, so that the locking components are not exposed. This can reduce friction between locking cam 1016 and soft tissues and ribs during insertion of stabilizer 1004 into a chest wall, can reduce palpability of stabilizer 1004, and can increase patient comfort. Also, by reducing the number of cavities exposed to soft tissues, internalize locking components of locking cam 1016 can reduce ingrowth, making removal of stabilizer 1004 and pectus bar 1002 easier and faster.

Figure 11A:
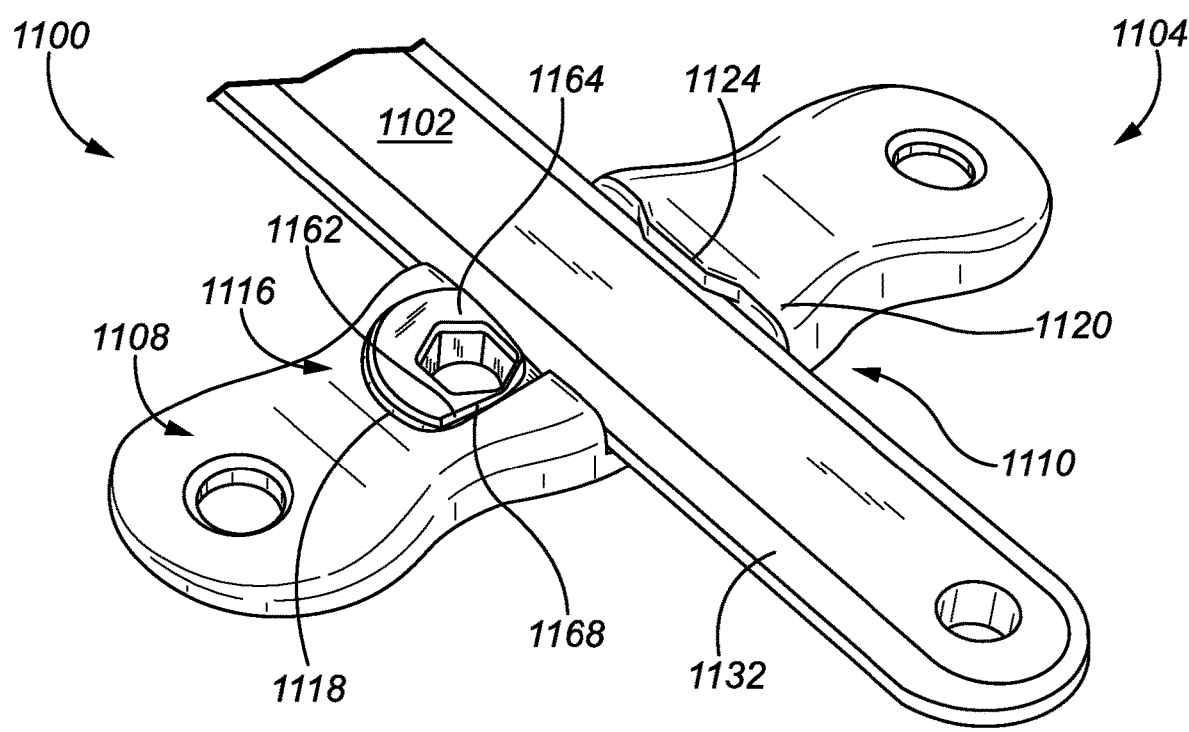
FIG. 11A illustrates an isometric view of a pectus bar assembly in a first condition, in accordance with at least one example of the present disclosure.
Figure 11B:
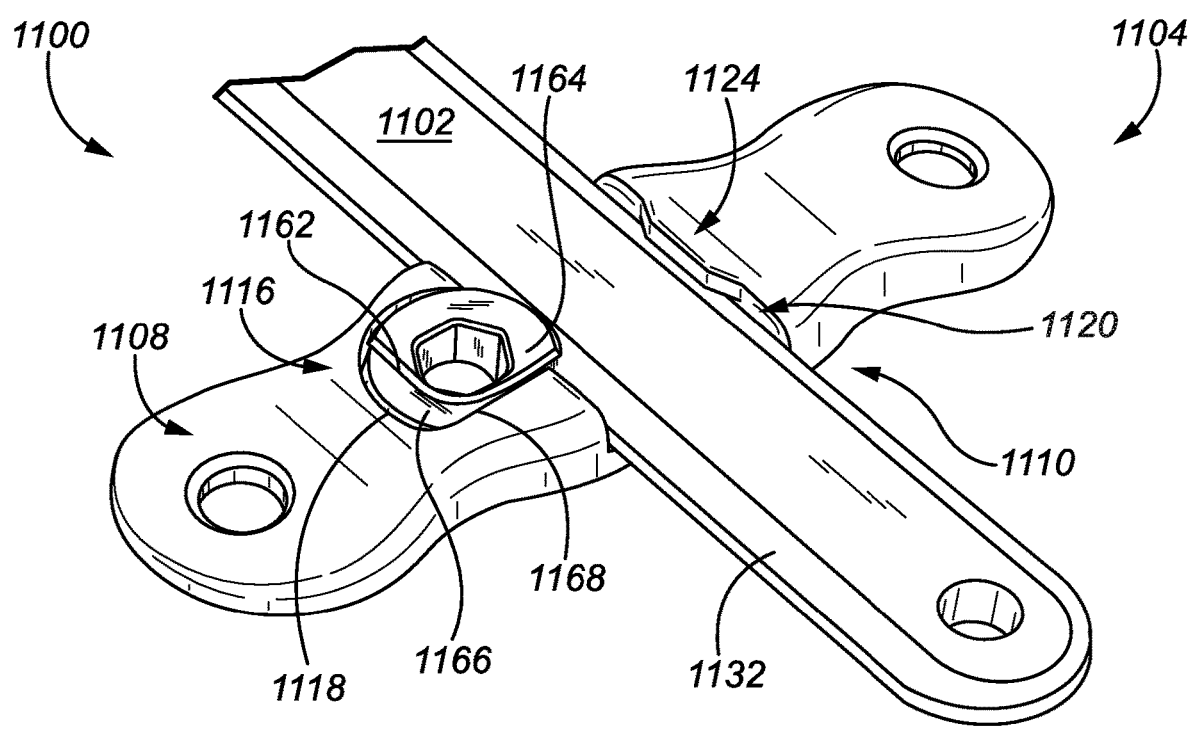
FIG. 11B illustrates an isometric view of a pectus bar assembly in a second condition, in accordance with at least one example of the present disclosure.

FIG. 11A illustrates an isometric view of pectus bar assembly 1100 with locking cam 1116 in an unlocked position. FIG. 11B illustrates an isometric view of pectus bar assembly 100 with locking cam 1116 in an unlocked position. FIGS. 11A and 11B are discussed below concurrently.

Pectus bar assembly 1100 can include pectus bar 1102 (only a portion of pectus bar 1102 is shown in FIGS. 1A and 11B) and stabilizer 1104. Stabilizer 1104 can include first portion 1108, second portion 1110, locking cam 1116, cam bore 1118, recessed portion 1120, and shelf 1124. Locking cam 1116 can include unlock stop 1162, lock stop 1164, and nesting portion 1166 (FIG. 11B). Cam bore 1118 can include stabilizer stop 1168.

Pectus bar assembly 1100 can be connected and can operate similarly to pectus bar assemblies 100, 200, 900, and 1000. However, pectus bar assembly 1100 differs in that recessed portion 1120 opens from first portion 1108 of stabilizer 1104, or opens to a top of stabilizer 1104. In other words, stabilizer 1104 is bottom-mounted to pectus bar 1102. Accordingly, shelf 1124 extends from first portion 1108 towards locking cam 1116.

Pectus bar assembly 1100 also differs in that locking cam 1116 includes unlock stop 1162 and lock stop 1164, and cam bore 1118 includes stabilizer stop 1168. Unlock stop 1162 and lock stop 1164 can be substantially straight portions or walls of locking cam 1116. Similarly, stabilizer stop 1168 can be a substantially straight portion of cam bore 1118. Stabilizer stop 1168 can be configured to contact unlock stop 1162 to prevent over-rotation of locking cam 1116 in the unlocked position and stabilizer stop can be configured to contact lock stop 1164 to prevent over-rotation of locking cam 1116 in the locked position. Contact between either unlock stop 1162 or lock stop 1164 and stabilizer stop 1168 can also provide tactile and/or audible feedback to a physician indicative of a rotational position of locking cam 1116 relative to cam bore 1118.

Locking cam 1116 also includes nesting portion 1166, which can be a recessed or undercut portion of locking cam 1116 that does not extend to a top surface of locking cam 1116. Nesting portion 1166 can nest within stabilizer 1104 under stabilizer stop 1168 when locking cam 1116 is in an unlocked position, as shown in FIG. 11A. Nesting portion 1166 can be exposed when locking cam 1116 is in a locked position, as shown in FIG. 11B.

Similar to a top-mounted stabilizer, in operation of some examples, when locking cam 1116 is in an unlocked position (as shown in FIG. 11A), bottom-mounted stabilizer 1104 can engage pectus bar 1102 at an angle to hook shelf 1124 onto top chamfer 1132 so that pectus bar 1102 can be inserted into recessed portion 1120 of stabilizer 1104. Locking cam 1116 can then be rotated clock-wise (unlock stop 1162 rotating away from stabilizer stop 1168) to engage top chamfer 1132 and secure locking cam 1116 and therefore stabilizer 1104 to pectus bar 1102. Clock-wise rotation of locking cam 1116 is limited by contact between lock stop 1164 of locking cam 1116 and stabilizer stop 1168, as shown in FIG. 11B.

To unlock pectus bar 1102 from stabilizer 1104, locking cam 1116 can be rotated counter-clock-wise to disengage pectus bar 1102. Counter-clock-wise rotation of locking cam 1116 is limited by contact between unlock stop 1166 of locking cam 1116 and stabilizer stop 1168, as shown in FIG. 11A. Once locking cam 1116 is unlocked from pectus bar 1102, pectus bar 1102 can be tilted to unhook pectus bar 1102 from shelf 1124 and can be removed from recessed portion 1120. Alternatively, while locking cam 1116 is unlocked and while pectus bar 1102 is inserted into recessed portion 1120, stabilizer 1104 can be moved or repositioned along a length of pectus bar 1102.

Figure 12A:
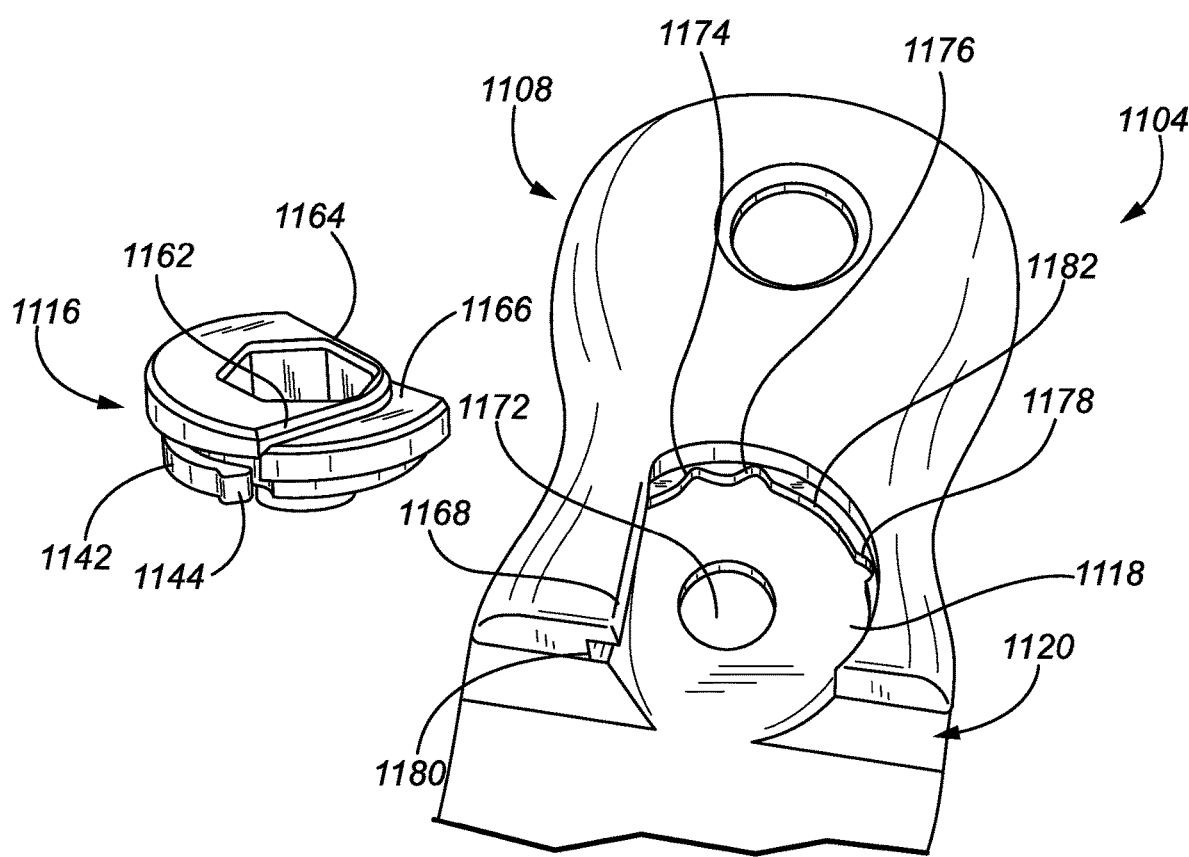
FIG. 12A illustrates an exploded partial view of a stabilizer, in accordance with at least one example of the present disclosure.

FIG. 12A illustrates an exploded partial view of a stabilizer 1104. Stabilizer 1104 can include first portion 1108, locking cam 1116, and recessed portion 1120. Locking cam 1116 can include arm 1142, tab 1144, unlock stop 1162, lock stop 1164, and recessed portion 1166. Cam bore 1118 can include stabilizer stop 1168, bearing bore 1172, unlocked notch 1174, partially locked notch 1176, locked notch 1178, undercut 1180, and locking bore 1182.

Pectus bar assembly 1100 can be connected and can operate consistently with the description of FIGS. 11A and 11B above, with further detail shown in FIG. 12. For example, FIG. 12A shows locking components of locking cam 1116, such as arm 142 and tab 1144. Arm 1142 can be secured to locking cam 1116 via a living hinge, as described above. FIG. 12A also shows how recessed portion 1166 of locking cam 1116 can have a profile configured to rotate within cam bore 1118 and can have a reduced height from a remainder of locking cam 1116, allowing recessed portion 1166 to nest within undercut 1180 of cam bore 1118 when locking cam 1116 is in a locked position.

Locking bore 1182 of cam bore 1118 can be a bore of a reduced diameter disposed within stabilizer 1104 and within cam bore 1118, such that cam bore 1118 is similar to a larger counter bore relative to locking bore 1182. FIG. 12 also shows notches within locking bore 1182, the notches configured to engage tab 1144 of locking cam 1116. Each of unlocked notch 1174, partially locked notch 1176, and locked notch 1178 can extend radially from locking bore 1182 and can terminate at the diameter of cam bore 1118. Each of unlocked notch 1174, partially locked notch 1176, and locked notch 1178 can be of a size and shape configured to retain tab 1144.

In operation of some examples, locking cam 1116 can be rotated within cam bore 1118. When rotated, tab 1144 and arm 1142 are forced to flex radially inward by a wall of locking bore 1182 until tab 1144 comes into alignment with a notch. When aligned with a notch, tab 1144 can extend into the notch, restricting rotation of locking cam 1166 relative to cam bore 1118. When tab 1144 engages unlocked notch 1174, locking cam 1116 is restricted from moving out of an unlocked position relative to pectus bar 1102. When tab 1144 engages partially locked notch 1176, locking cam 1116 is restricted from moving out of a partially locked position relative to pectus bar 1102. That is, locking cam 1116 can be engaging pectus bar 1102, but is not locking stabilizer 1104 to pectus bar 1102, so that stabilizer 1104 can be moved along a length of pectus bar 1102 but stabilizer 1104 cannot be removed from pectus bar 1102. When tab 1144 engages locked notch 1178, locking cam 1116 is restricted from moving out of a locked position relative to pectus bar 1102.

FIG. 12A also shows bearing bore 1172 that can be sized to retain a portion of locking cam 1116 and can be profiled to operate as a bearing surface with locking cam 1116 to ensure smooth rotation of locking cam 1116 within cam bore 1118.

Figure 12B:
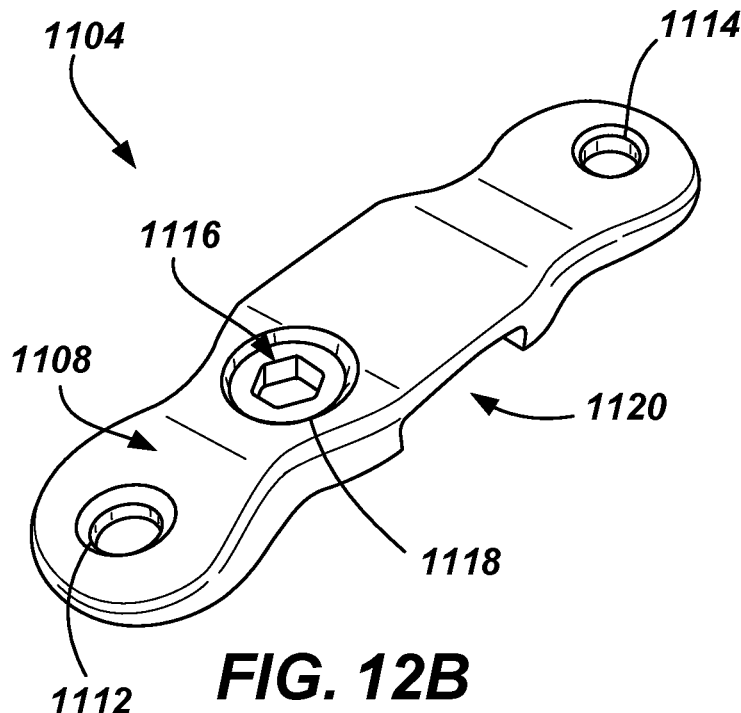
FIG. 12B illustrates an isometric view of a stabilizer from a top perspective, in accordance with at least one example of the present disclosure.
Figure 12C:
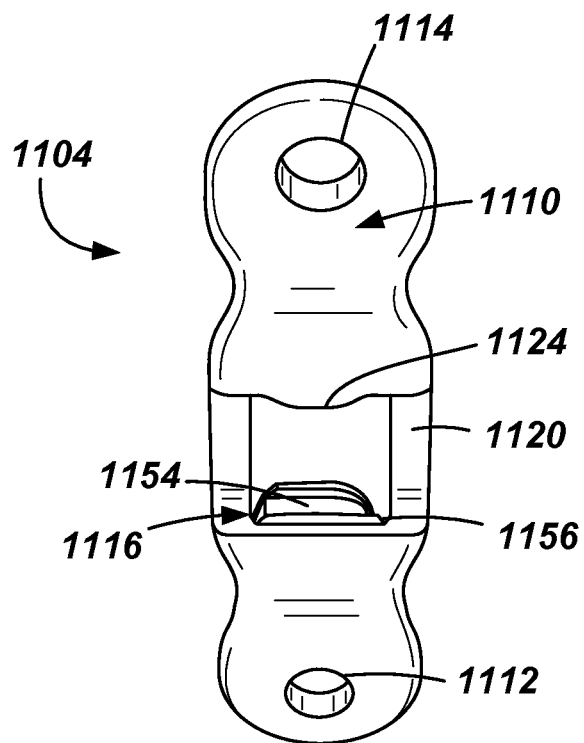
FIG. 12C illustrates an isometric view of a stabilizer from a bottom perspective, in accordance with at least one example of the present disclosure.

FIG. 12B illustrates an isometric view of stabilizer 1104 from a top perspective, in accordance with at least one example of the present disclosure. FIG. 12C illustrates an isometric view of stabilizer 1104 from a bottom perspective, in accordance with at least one example of the present disclosure. FIGS. 12B and 12C are discussed below concurrently.

Stabilizer 1104 can include first portion 1108, second portion 1110, stabilizer bores 1112 and 1114, locking cam 1116, cam bore 1118, recessed portion 3820, and shelf 1124. Locking cam 1116 can include cam shelf 1154. Recessed portion 1120 can include pocket 1156.

Stabilizer 1104 can be similar to the stabilizers discussed above, especially stabilizer 1104 of FIG. 12A, where the locking components of locking cam 1116, such as a tab, arm, and hinge, can be disposed within stabilizer 1104 so that the locking components are not exposed. This can reduce friction between locking cam 1116 and soft tissues and ribs during insertion of stabilizer 1104 into a chest wall, can reduce palpability of stabilizer 1104, and can increase patient comfort. Also, by reducing the number of cavities exposed to soft tissues, internalize locking components of locking cam 1116 can reduce ingrowth, making removal of stabilizer 3804 easier and faster. Stabilizer 1104 of FIGS. 12B and 12C can differ from stabilizer 1104 of FIG. 12A in that cam 1116 of FIGS. 12B and 12C may include a top profile that does not include the tab, arm, and hinge, but is substantially round, similar to cam 1016 of FIG. 10. Further, the angled faces of cam 1116 of FIGS. 12B and 12C can be similar to faces or stops 1162 and 1164 of cam 1116 of FIG. 11B, but can be disposed within stabilizer 1104.

FIG. 12C also shows that recessed portion 1120 can include pocket 1156, which can be an opening in the underside of stabilizer 1104 from which cam shelf 1154 can extend when locking cam 1116 is rotated to the locked position (to engage a pectus bar).

Pocket 1156 can also be sized to receive locking cam 1116 therethrough during assembly. That is, locking cam 1116 can be inserted from pocket 1156 and can be positioned into cam bore 1118 through pocket 1156, which can simplify assembly while allowing for the locking components of locking cam 1116 to be disposed internal to stabilizer 1104.

Figure 13A:
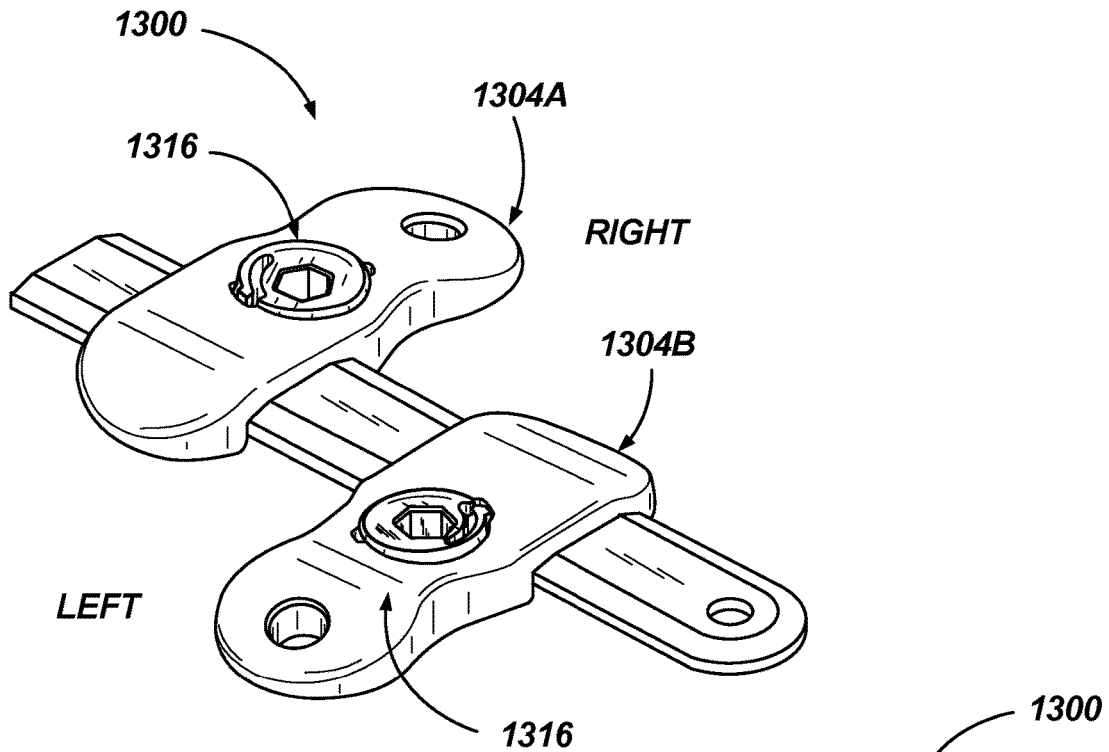
FIG. 13A illustrates a top isometric view of a pectus bar assembly, in accordance with at least one example of the present disclosure.
Figure 13B:
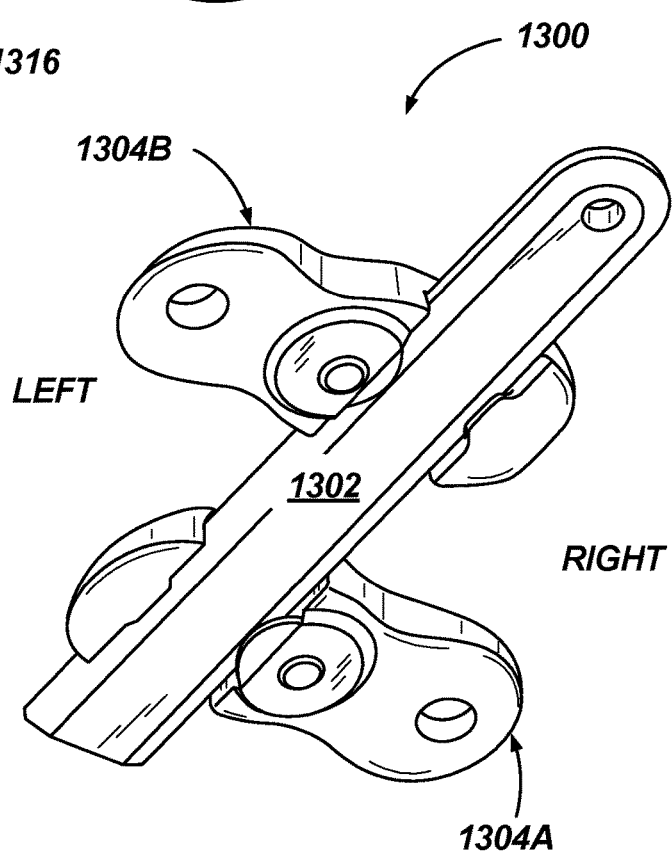
FIG. 13B illustrates a bottom isometric view of a pectus bar assembly, in accordance with at least one example of the present disclosure.

FIG. 13A illustrates a top isometric view of a pectus bar assembly 1300. FIG. 13B illustrates a bottom isometric view of pectus bar assembly 1300. FIGS. 13A and 13B are discussed below concurrently.

Pectus bar assembly 1300 can include pectus bar 1302 and stabilizers 1304A and 1304B. Also shown in FIGS. 13A and 13B are orientation indicators Left and Right.

Pectus bar assembly 1300 can be connected and can operate similar to pectus bar assemblies discussed above. However, pectus bar assembly 1300 differs in that it includes stabilizers 1304A and 1304B, each of which only include a single bore positioned on a same side of each stabilizer as the locking cam. Stabilizers 1304A and 1304B can be identical so that in pectus bar assembly 1300, stabilizers 1304A and 1304B can be placed on pectus bar 1302 in either orientation (bore on left side of pectus bar 1302 or bore on right side of pectus bar 1302). In FIGS. 13A and 13B stabilizers 1304A and 1304B are shown as extending oppositely (one left and one right) from pectus bar 1302. Because stabilizers 1304A and 1304B can extend to only one side of pectus bar 1302, stabilizers 1304A and 1304B can provide the benefit of reducing palpability for a patient.

Because stabilizers 1304A and 1304B can be identical, stabilizers 1304A and 1304B can also be mounted on the same side (either both extending left or both extending right of pectus bar 1302). Also, because stabilizers 1304A and 1304B include only one bore, securing stabilizers 1304A and 1304B to ribs and costal tissue of a chest wall may be faster.

Figure 14A:
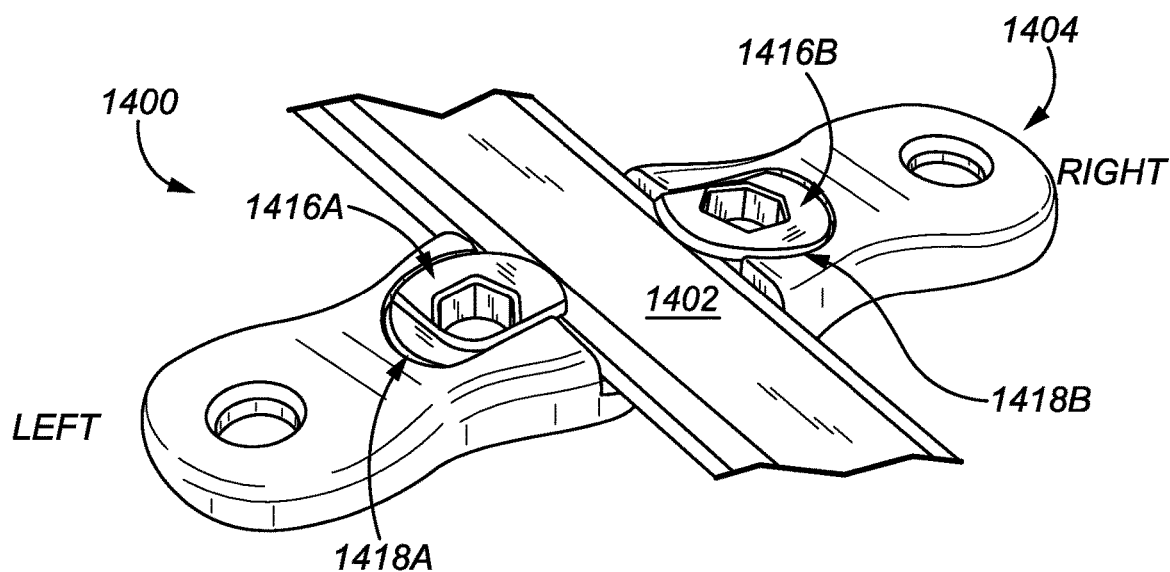
FIG. 14A illustrates an isometric view of a pectus bar assembly in a first condition, in accordance with at least one example of the present disclosure.
Figure 14B:
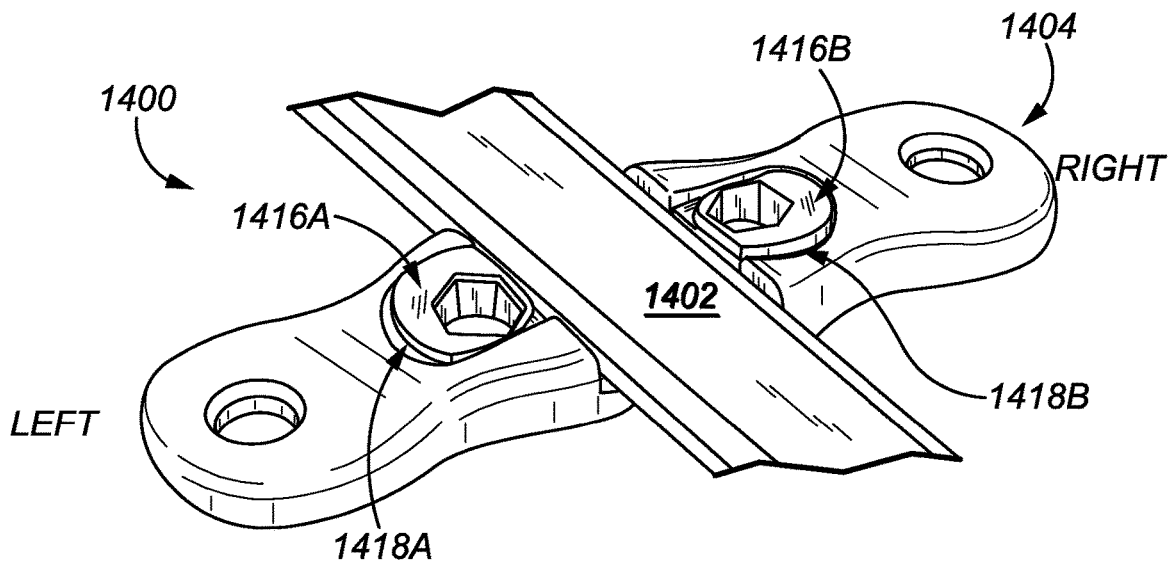
FIG. 14B illustrates an isometric view of a pectus bar assembly in a second condition, in accordance with at least one example of the present disclosure.

FIG. 14A illustrates an isometric view of pectus bar assembly 1400 with locking cams in a locked position. FIG. 14A illustrates an isometric view of pectus bar assembly 1400 with locking cams in an unlocked position. FIGS. 14A and 14B are discussed below concurrently.

Pectus bar assembly 1400 can include pectus bar 1402 and stabilizer 1404. Stabilizer 1404 can include locking cams 1416A and 1416B and cam bores 1418A and 1418B. Also shown in FIGS. 14A and 14B are orientation indicators Left and Right.

Pectus bar assembly 1400 can be connected and can operate similar to pectus bar assemblies discussed above. However, pectus bar assembly 1400 differs in that stabilizer 1400 includes locking cams 1416A and 1416B. Locking cams 1416A and 1416B can be disposed in cam bores 1418A and 1418B, respectively. Locking cams 1416A and 1416B can be rotatable within cam bores 1418A and 1418B and can lock and unlock to cam bores 1418A and 1418B, respectively, as described above, and can lock to pectus bar 1402.

In operation of some examples, pectus bar 1402 can be aligned with a recessed portion of stabilizer and inserted into the recessed portion in a bottom-mount fashion when locking cams 1416A and 1416B are in an unlocked position. Once pectus bar 1402 is inserted into the recessed portion, locking cams 1416A and 1416B can be rotated to locked positions to engage pectus bar 1402 and secure pectus bar 1402 to stabilizer 1404. As discussed above, this process can be reversible.

Including locking cams 1416A and 1416B provides the benefit of being able to directly insert pectus bar 1402 into the recessed portion of stabilizer 1404 without tilting stabilizer 1404 or pectus bar 1402. That is, stabilizer 1404 does not need to be hooked onto pectus bar 1402. However, if hooking is desired, in some examples, one of locking cams 1416A and 1416B can be rotated to a locked position so that stabilizer 1404 can be hooked onto pectus bar 1402. Thereafter, the other of locking cams 1416A and 1416B can be rotated to a locked position.

Figure 15A:
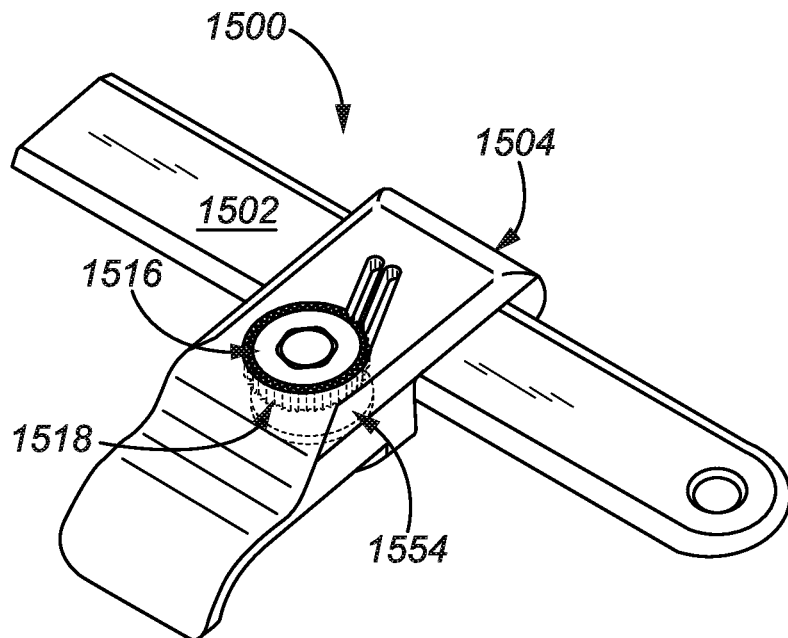
FIG. 15A illustrates an isometric view of a pectus bar assembly, in accordance with at least one example of the present disclosure.
Figure 15B:
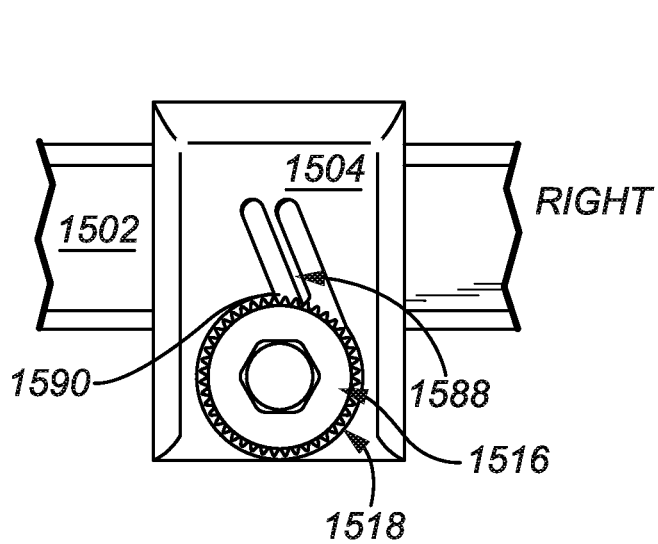
FIG. 15B illustrates a top view of a portion of a pectus bar assembly, in accordance with at least one example of the present disclosure.
Figure 15C:
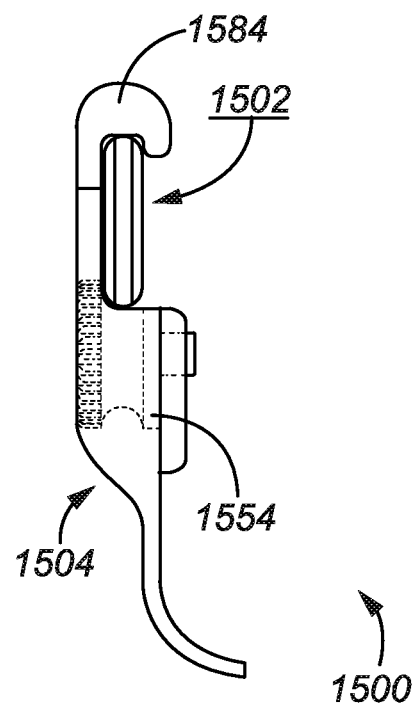
FIG. 15C illustrates a side view of a pectus bar assembly, in accordance with at least one example of the present disclosure.
Figure 16A:
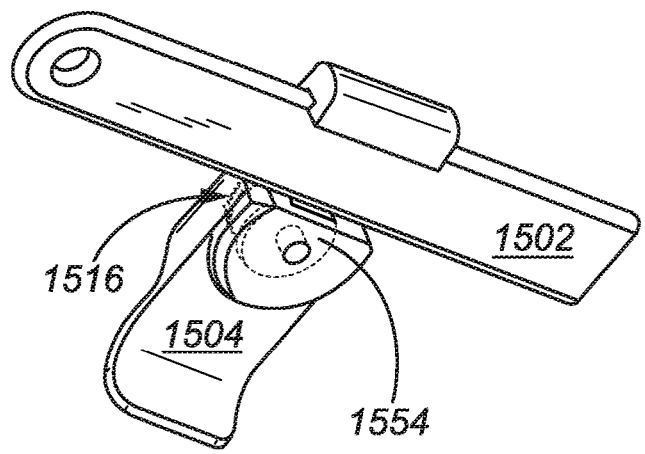
FIG. 16A illustrates a bottom isometric view of a pectus bar assembly in a first condition, in accordance with at least one example of the present disclosure.
Figure 16B:
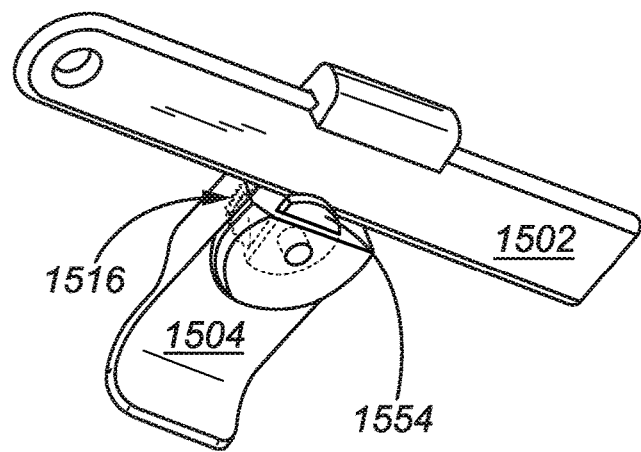
FIG. 16B illustrates a bottom isometric view of a pectus bar assembly in a second condition, in accordance with at least one example of the present disclosure.

FIG. 15A illustrates an isometric view of pectus bar assembly 1500. FIG. 15B illustrates a top view of a portion of pectus bar assembly 1500. FIG. 15C illustrates a side view of pectus bar assembly 1500. FIG. 16A illustrates a bottom isometric view of pectus bar unlocked assembly 1500. FIG. 16B illustrates a bottom isometric view of pectus bar locked assembly 1500. FIGS. 15A-15C and 16A and 16B are discussed below concurrently.

Pectus bar assembly 1500 can include pectus bar 1502, and stabilizer 1504. Stabilizer 1504 can include locking cam 1516, cam bore 1518, recessed portion 1520, top hook 1584 (FIG. 15C), and pawl 1588. Locking cam 1516 can include teeth 1590.

Pectus bar assembly can be connected and can operate similarly to the pectus bar assemblies described above. However, stabilizer 1504 can differ from stabilizers described above. For example, stabilizer 1504 can include top hook 1584. Top hook 1584 can be configured to hook a portion of pectus bar 1502. Also, stabilizer 1504 can include pawl 1588 and locking cam 1516 can include teeth 1590, where teeth 1590 engageable with pawl 1588.

In operation of some examples, locking cam 1516 can be rotated so that cam shelf 1554 engages and secures to pectus bar 1502. As locking cam 1516 rotates, teeth 1590 rotate and engage pawl 1588. Pawl 1588 can flex via a living hinge, allowing teeth 1590 to pass in a ratcheting fashion as locking cam 1516 rotates in a clock-wise direction. Pawl 1588 can resist rotation of locking cam 1516 as pawl 1588 engages teeth 1590, preventing locking cam 1516 from rotating in a counter-clock-wise direction. In this way, pawl 1588 and teeth 1518 can prevent accidental unlocking of shelf 1554 from pectus bar 1502. In some examples, a tool can be used to disengage pawl 1588 from teeth 1590, allowing locking cam 1516 to rotate in either direction freely. In some examples, a tool or driver can apply a torque in a counter-clockwise direction to permanently deform pawl 1588 to unlock locking cam 1516 from pectus bar 1502 so that stabilizer 1504 can be removed.

Figure 17A:
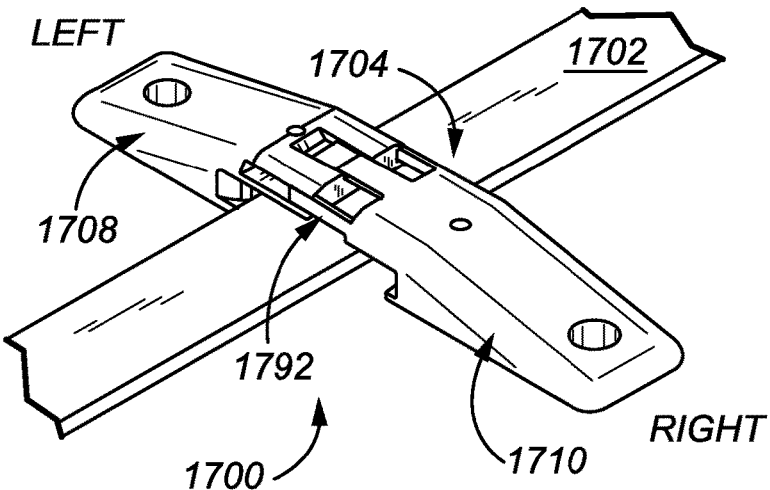
FIG. 17A illustrates a top isometric view of a pectus bar assembly in a first condition, in accordance with at least one example of the present disclosure.
Figure 17B:
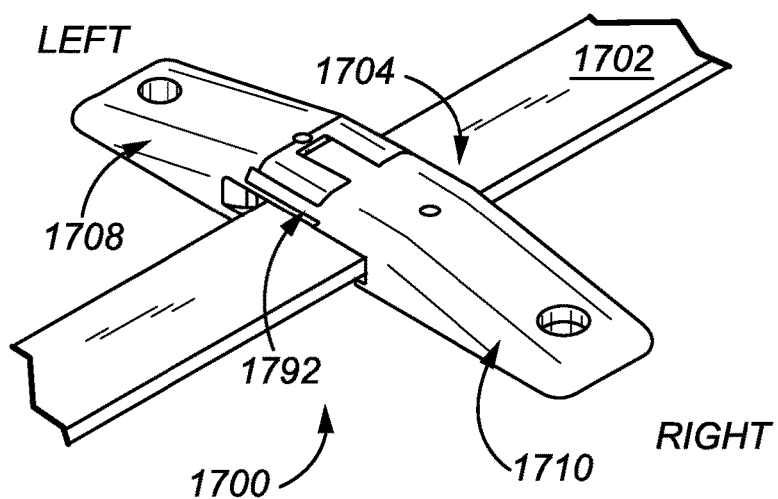
FIG. 17B illustrates a top isometric view of a pectus bar assembly in a second condition, in accordance with at least one example of the present disclosure.

FIG. 17A illustrates a top isometric view of pectus bar assembly 1700 in an unlocked position. FIG. 17B illustrates a top isometric view of pectus bar assembly 1700 in an unlocked position. FIGS. 17A and 17B are discussed below concurrently.

Pectus bar assembly 1700 can include pectus bar 1702, and stabilizer 1704. Stabilizer 1704 can include first portion 1708, second portion 1710, and locking portion 1792. Also shown in FIGS. 17A and 17B are orientation indicators Left and Right.

Pectus bar assembly 1700 can be similar to the pectus bar assemblies described above, except that stabilizer 1704 can include first portion 1708 (left portion) and second portion 1710 (right portion). Each of first portion 1708 and second portion 1710 can include a hook or shelf to engage and secure pectus bar 1702 to stabilizer 1704. First portion 1708 and second portion 1710 can also form locking portion 1792 which can lockingly engage as first portion 1708 and second portion 1710 translate towards each other. As locking portion 1792 engages, first portion 1708 and second portion 1710 are secured to each other and together with their hooks, retain and secure pectus bar 1702. By translatingly locking to pectus bar 1702, stabilizer 1704 offers the benefit of locking to a pectus bar without tilting or turning about pectus bar 1702.

Figure 18:
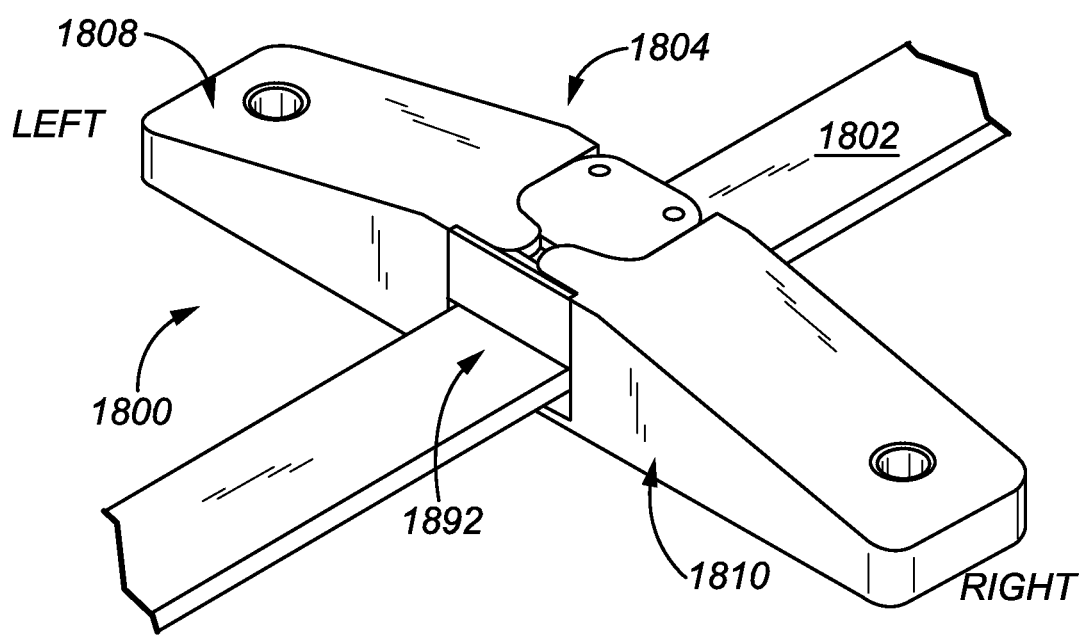
FIG. 18 illustrates a top isometric view of a pectus bar assembly, in accordance with at least one example of the present disclosure.
Figure 19A:
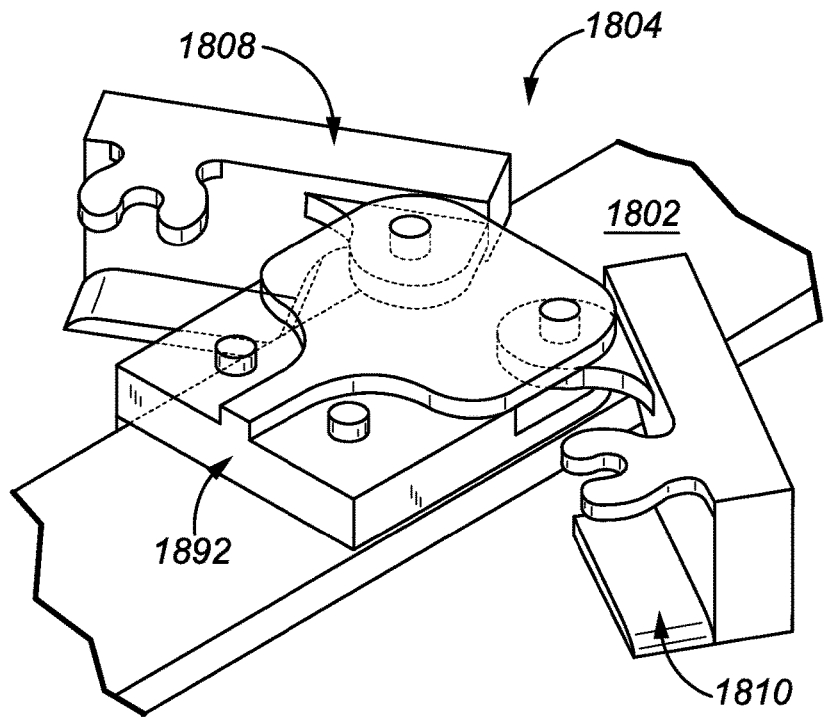
FIG. 19A illustrates a top isometric view of a portion of a pectus bar assembly in a first condition, in accordance with at least one example of the present disclosure.
Figure 19B:
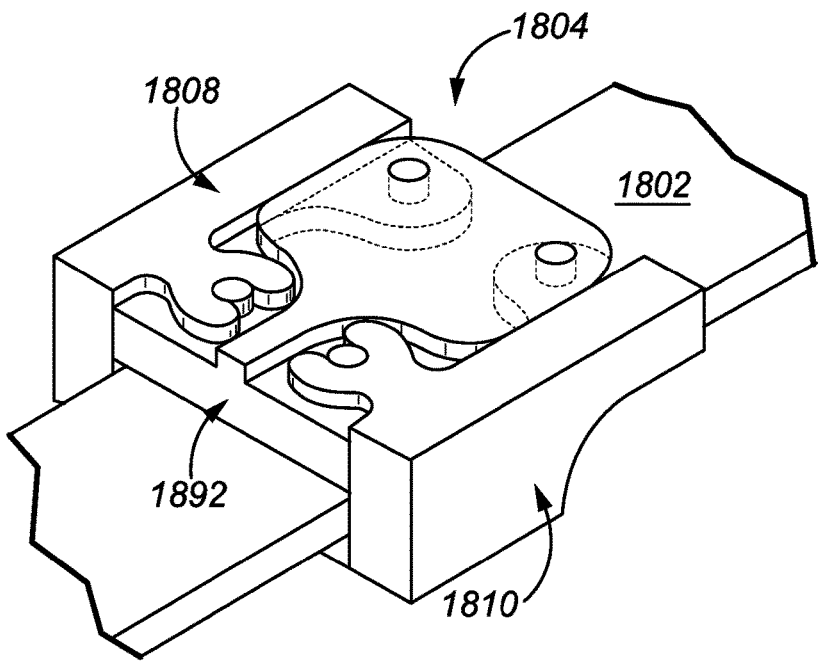
FIG. 19B illustrates a top isometric view of a portion of a pectus bar assembly in a second condition, in accordance with at least one example of the present disclosure.

FIG. 18 illustrates a top isometric view of pectus bar assembly 1800. FIG. 19A illustrates a top isometric view of a portion of pectus bar assembly 1800 in an unlocked position. FIG. 19B illustrates a top isometric view of a portion of pectus bar assembly 1800 in a locked position. FIGS. 18, 19A, and 19B are discussed below concurrently.

Pectus bar assembly 1800 can include pectus bar 1802 and stabilizer 1804. Stabilizer 1804 can include first portion 1808, second portion 1810, and locking portion 1892. Also shown in FIG. 18 are orientation indicators Left and Right.

Pectus bar assembly 1800 can be similar to the pectus bar assemblies discussed above. However, pectus bar assembly 1800 can differ where stabilizer 1804 can be engageable with pectus bar 1802, where first portion 1808 can be engageable with a first side of pectus bar 1802 and second portion 1810 can be engageable with second side of pectus bar 1802. Locking portion (or mechanism) 1892 can connect first portion 1808 to second portion 1810, where locking portion 1892 is actuatable to secure the stabilizer to the pectus bar.

Locking portion can further include a first hinge coupling first portion 1808 to locking mechanism 1892 and a second hinge coupling second portion 1810 to the locking mechanism. Locking mechanism 1892 can further include a first post and a second post. First portion 1808 can also include a first locking fork releasably securable to the first post to secure first portion 1808 to pectus bar 1802. Second portion 1810 can further include a second locking fork releasably securable to the second post to secure second portion 1810 to pectus bar 1802.

First portion 1808 can further include a first shelf extending toward second portion 1810 and engageable with pectus bar 1802. Second portion 1810 can further include a second shelf extending toward first portion 1810 and can be engageable with pectus bar 1802.

Figure 20A:
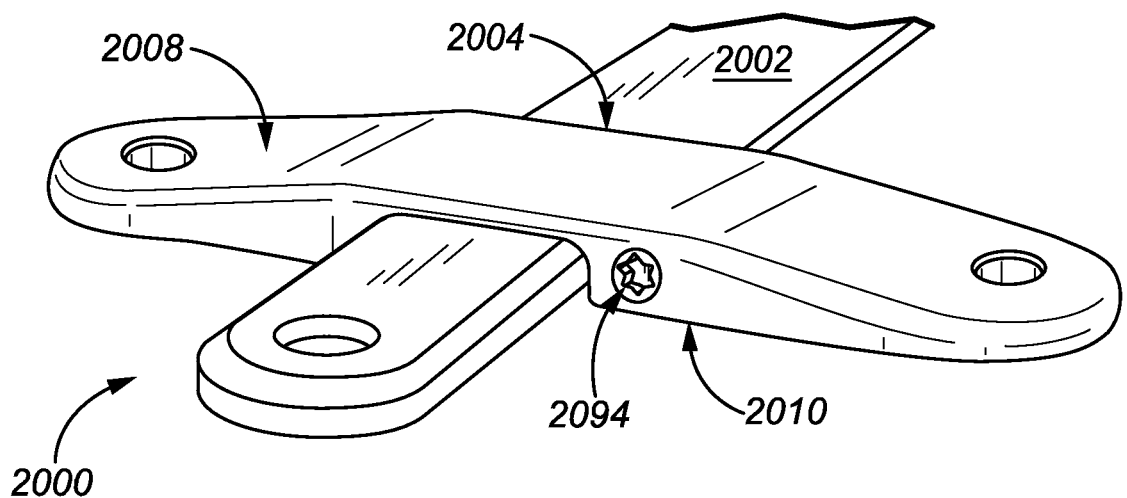
FIG. 20A illustrates an isometric view of a pectus bar assembly, in accordance with at least one example of the present disclosure.
Figure 20B:
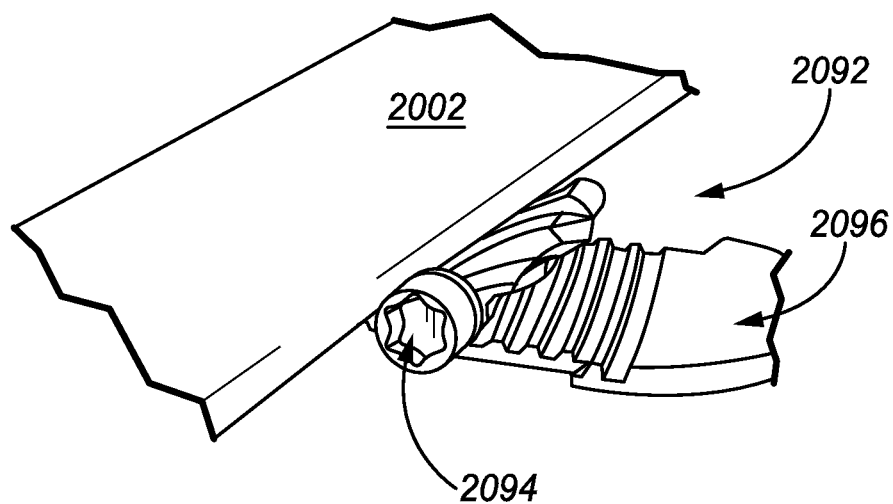
FIG. 20B illustrates a partially-exploded isometric view of a pectus bar assembly, in accordance with at least one example of the present disclosure.

FIG. 20A illustrates an isometric view of pectus bar assembly 2000. FIG. 20B illustrates a partially-exploded isometric view of pectus bar assembly 2000. FIGS. 20A and 20B are discussed below concurrently.

Pectus bar assembly 2000 can include pectus bar 2002 and stabilizer 2004. Stabilizer 2004 can include first portion 2008, second portion 2010, and locking portion 2092, which can include driver 2094 and shelf 2096.

Pectus bar assembly 2000 can be similar to the pectus bar assemblies discussed above. However, stabilizer 2004 can differ in that second portion (bottom portion) 2010 can be opposite first portion (top portion) 2008, where second portion 2010 can include a recessed portion configured to receive pectus bar 2002. Second portion 2010 can also include shelf 2096 which can be translatable into the recess to engage pectus bar 2002 and secure stabilizer 2004 relative to pectus bar 2002. Driver 2094 can be rotatable to translate shelf 2096 relative to pectus bar 2002 and stabilizer 2004 to engage and disengage pectus bar 2002. Stabilizer 2004 can offer the benefit of having a locking mechanism that is accessible and operable from the side.

Figure 21:
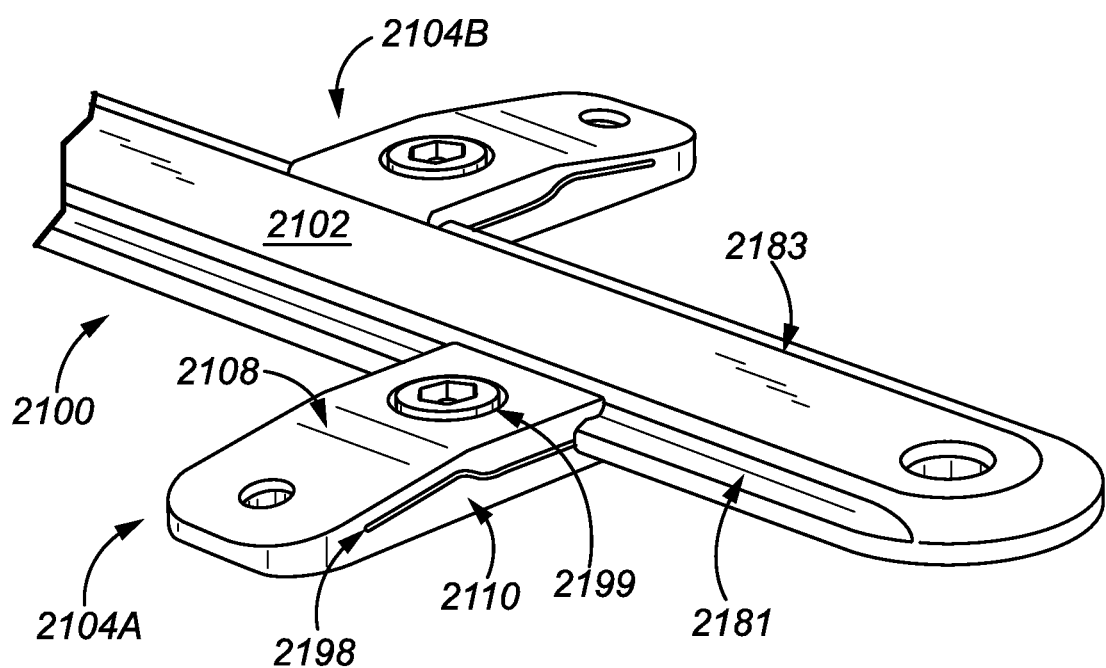
FIG. 21 illustrates an isometric view of a pectus bar assembly, in accordance with at least one example of the present disclosure.

FIG. 21 illustrates an isometric view of pectus bar assembly 2100, which can include pectus bar 2102 and stabilizers 2104A and 2104B. Each of stabilizer 2104A and 2104B can include first portion 2108, second portion 2110, living hinge 2198, and fastener 2199. Pectus bar 2102 can include first groove 2181 and second groove 2183.

Stabilizer 2104A can be engageable with pectus bar 2102 and can include a recess configured to engage first groove 2181 of the pectus bar. First portion 2108 and second portion 2110 can be coupled by living hinge 2198 and can form the recess opposite living hinge 2198. Fastener 2199 can be couplable to first portion 2108 and second portion 2110 to open and close the recess, where opening the recess releases stabilizer 2104A from pectus bar 2102 and closing the recess secures stabilizer 2104A to pectus bar 2102.

Though only stabilizer 2104 is discussed above, each aspect of stabilizer 2104A is applicable to stabilizer 2104B. Stabilizer 2104B can be engageable with second groove 2183 opposite groove 2181. In some examples, though not shown, stabilizers 2104A and 2104B can include a protrusion that extends towards pectus bar 2102 to engage a circumferential groove of pectus bar and prevent rotation of stabilizer relative to pectus bar.

Figure 22:
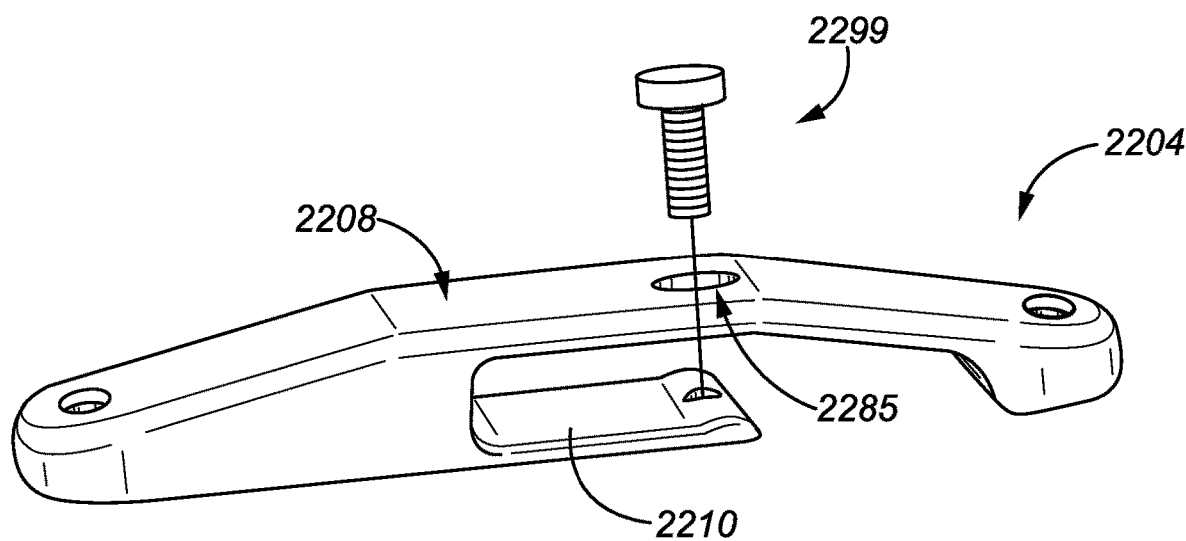
FIG. 22 illustrates an isometric view of a stabilizer, in accordance with at least one example of the present disclosure.

FIG. 22 illustrates an isometric view of stabilizer 2204, which can include first portion 2208, second portion 2210, bore 2285, and fastener 2299. Stabilizer 2204 can be engageable with a pectus bar, such as pectus bar 2102 of FIG. 21. First portion 2108 can include bore 2285, which can be smooth or threaded. Second portion 2110 can be opposite first portion 2108. Second portion 2110 can include a recess configured to receive the pectus bar. Fastener 2299 can pass through bore 2285 to engage the second portion and secure the pectus bar within the recess.

Figure 23:
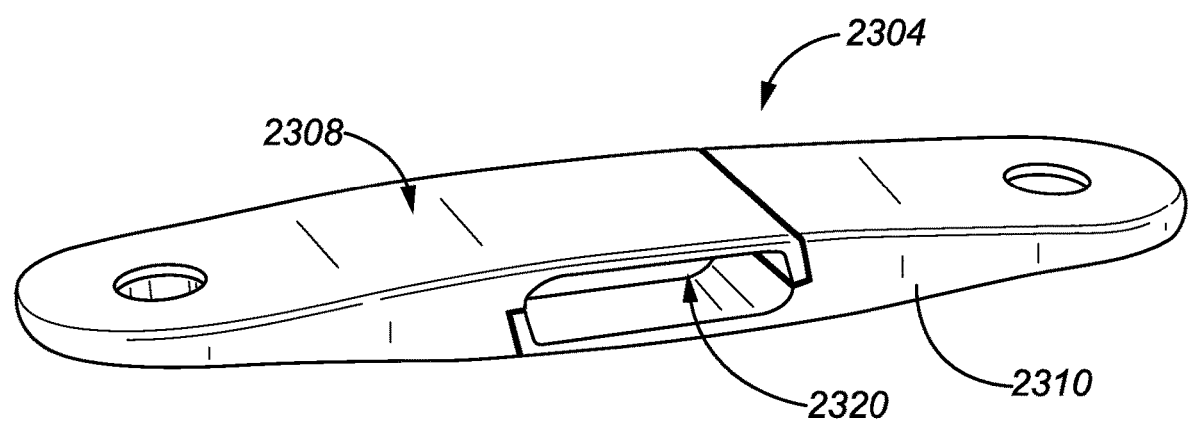
FIG. 23 illustrates an isometric view of a stabilizer, in accordance with at least one example of the present disclosure.

FIG. 23 illustrates an isometric view of stabilizer 2304, which can include first portion 2308, second portion 2310, and recess 2320. Second portion 2310 can be symmetrical to first portion 2308. First portion 2308 can be couplable to second portion 2310 to engage a pectus bar at recess 2320, securing the pectus bar to stabilizer 2304.

Figure 24:
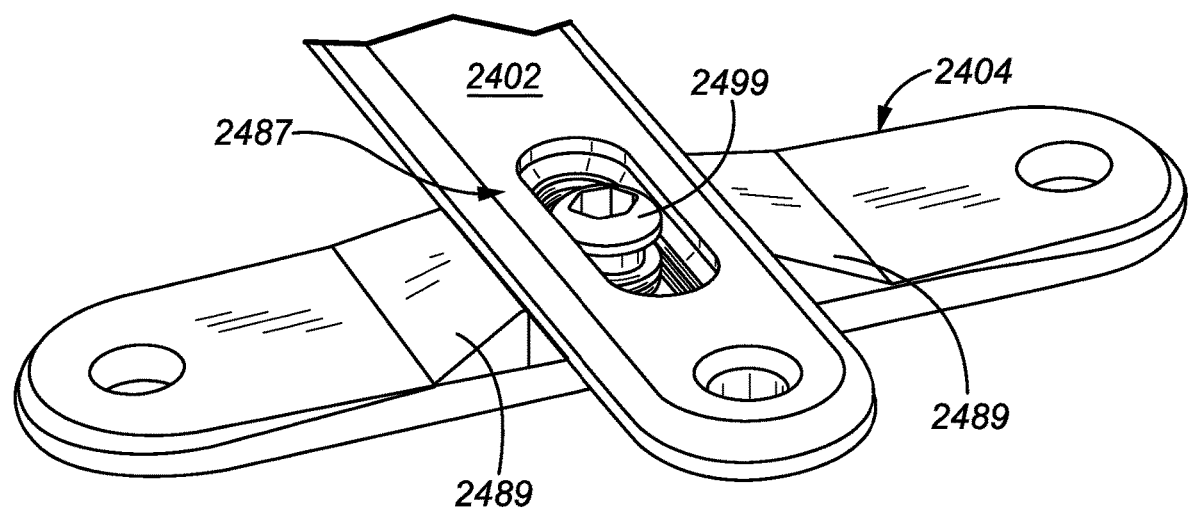
FIG. 24 illustrates an isometric view of a pectus bar assembly, in accordance with at least one example of the present disclosure.

FIG. 24 illustrates an isometric view of pectus bar assembly 2400, which can include pectus bar 2402, stabilizer 2404, and fastener 2499. Pectus bar 2402 can include slot 2487. Stabilizer 2404 can include ramps 2489.

In some examples, slot 2487 can be threaded, and can extend through a body of pectus bar 2402. Stabilizer 2404 can include a recess formed by ramps 2489, where the recess can be configured to receive pectus bar 2402. Fastener 2499 can pass through and threadably engage slot 2487 and the recess of stabilizer 2404 to secure pectus bar 2402 to stabilizer 2404. Because slot 2487 is elongate, stabilizer 2404 can be secured to pectus bar 2402 in many positions along pectus bar 2402 as limited by a length of slot 2487.

Figure 25:
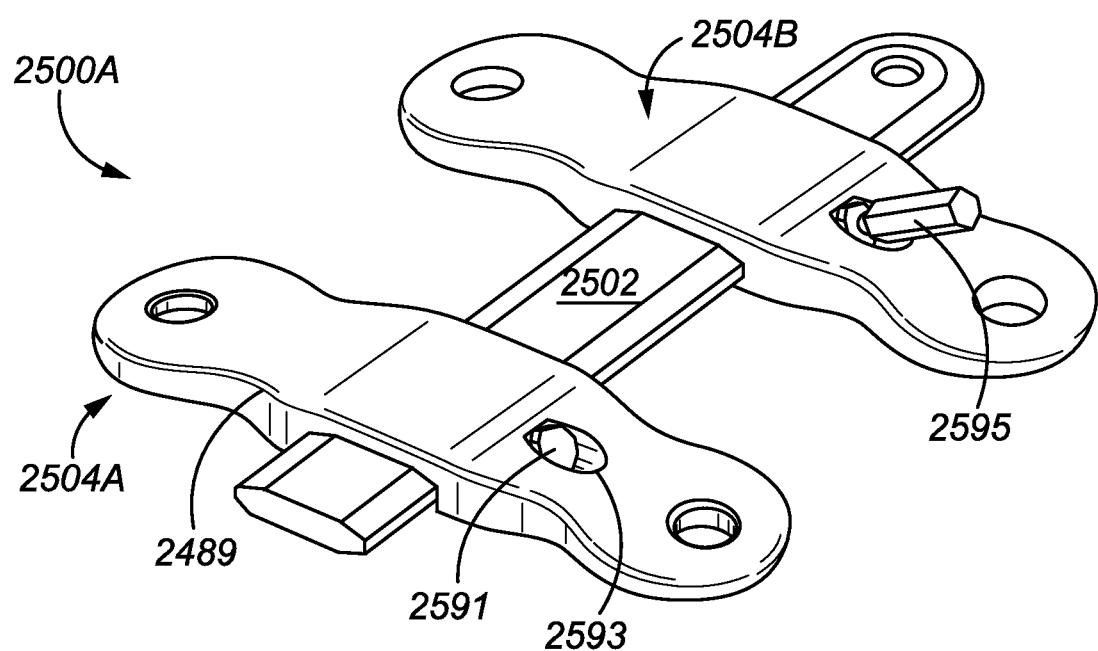
FIG. 25 illustrates an isometric view of a pectus bar assembly, in accordance with at least one example of the present disclosure.

FIG. 25 illustrates an isometric view of a pectus bar assembly 2500, which can include pectus bar 2502 and stabilizer 2504. Stabilizer 2504 can include a recess configured to receive the pectus bar and bore 2593 extending through a body of stabilizer 2504, where bore 2593 extends through stabilizer 2504 at an angle and intersects with a recess of stabilizer 2504. Pectus bar assembly can also include fastener 2591 threadably passable through bore 2593 and engageable with a bottom chamfer of pectus bar 2502 to draw pectus bar 2502 into a recessed portion of stabilizer 2504, securing stabilizer 2504 to pectus bar 2502. Driver 2595 can be configured to turn fastener 2591 to engage and disengage pectus bar 2502.

Figure 26:
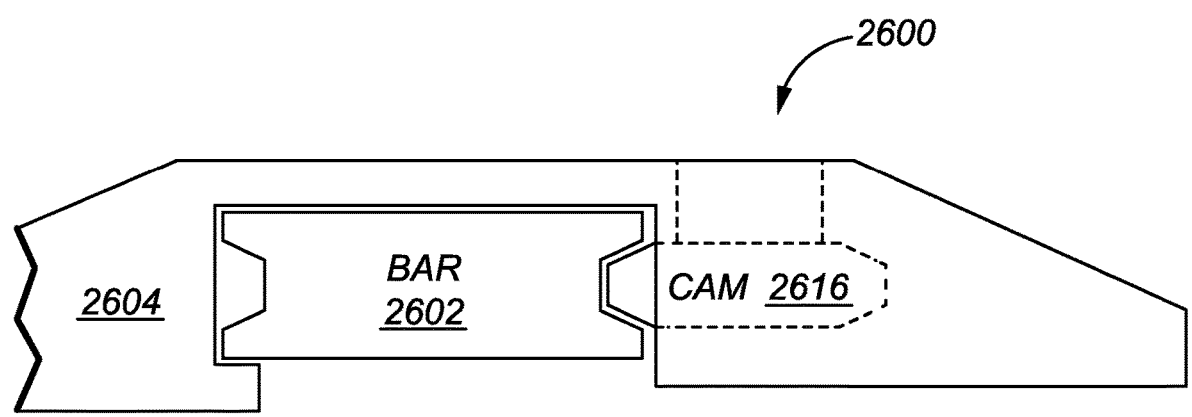
FIG. 26 illustrates aside schematic cross-sectional view of a pectus bar assembly, in accordance with at least one example of the present disclosure.

FIG. 26 illustrates a side schematic cross-sectional view of a pectus bar assembly 2600, which can include pectus bar 2602 and stabilizer 2604. Stabilizer 2604 can include cam 2616. Pectus bar assembly 2600 can be similar to the pectus bar assemblies described above, except that pectus bar 2602 can include a negative geometry configured to receive a protrusion extendable from cam 2616 to releasably lock stabilizer 2604 to pectus bar 2602.

Figure 27:
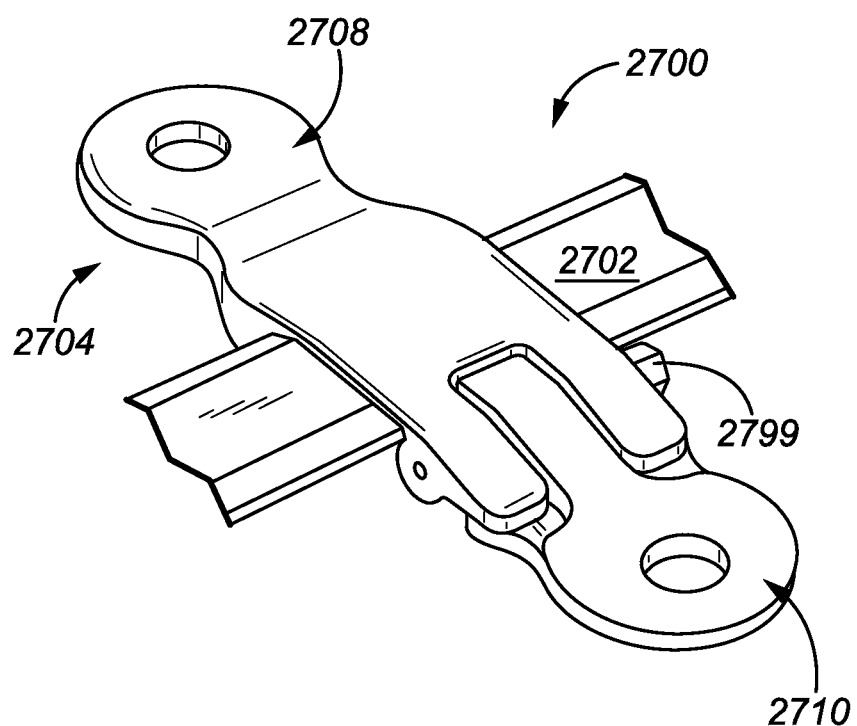
FIG. 27 illustrates an isometric view of a pectus bar assembly, in accordance with at least one example of the present disclosure.

FIG. 27 illustrates an isometric view of pectus bar assembly 2700, which can include pectus bar 2702 and stabilizer 2704. Stabilizer 2704 can include first portion 2708, second portion 2710, and retaining member 2799.

First portion 2708 can be engageable with a first side of pectus bar 2702. Second portion 2710 can be translatably coupled to first portion 2708, such that first portion 2708 and second portion 2710 secure stabilizer 2704 to pectus bar 2710 when second portion 2710 is in the closed position. Retaining member 2799 can be adjustable to translate second portion 2710 between the open and closed position to unlock and lock second portion 2710, respectively.

Figure 28:
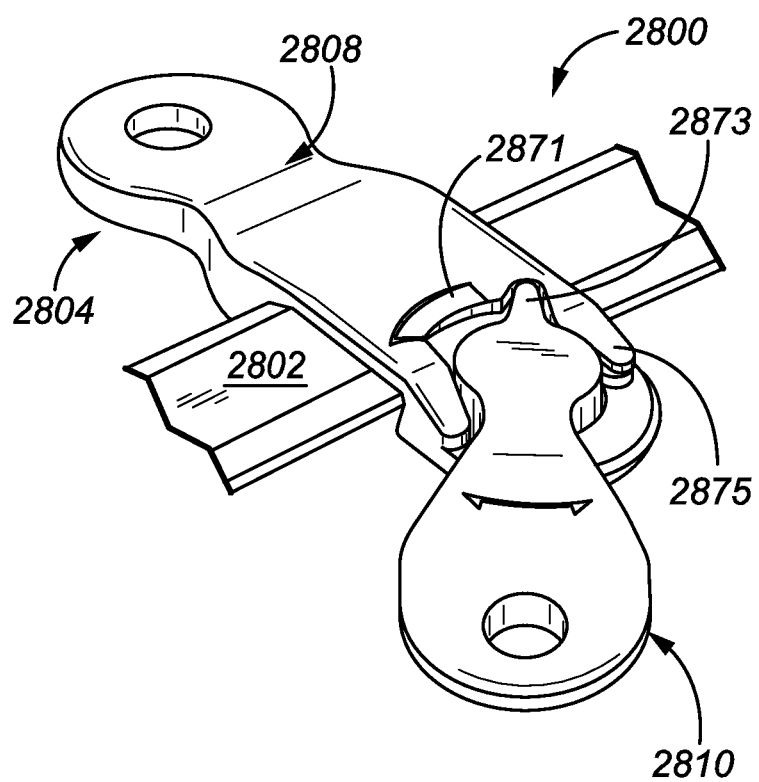
FIG. 28 illustrates an isometric view of a pectus bar assembly, in accordance with at least one example of the present disclosure.

FIG. 28 illustrates an isometric view of pectus bar assembly 2800, which can include pectus bar 2802 and stabilizer 2804. Stabilizer 2804 can include first portion 2808 and second portion 2810. First portion 2808 can include ramp 2871 and stop 2875. Second portion 2810 can include tab 2873.

First portion 2808 can be engageable with a first side of pectus bar 2802. Second portion 2810 can be rotatably coupled to first portion 2808, where first portion 2808 is rotatable between an open and a closed position and engageable with a second side of pectus bar 2802 in the closed position.

Tab 2873 can engageable with a notch formed between ramp 2871 and stop 2875 of first portion 2808, which can restrict rotation of second portion 2810 relative to first portion 2808 when second portion 2810 is in the closed position, locking stabilizer 2804 to pectus bar 2802. Second portion 2810 can include a shelf rotatable with second portion 2810 to engage pectus bar 2802 when second portion 2810 is in the locked position.

Pectus bar assembly 2800 offers the benefit of tool-less locking of stabilizer 2804 to pectus bar 2802, which can increase surgical efficiency and can eliminate the need for a special installation tool, saving time and cost.

Figure 29:
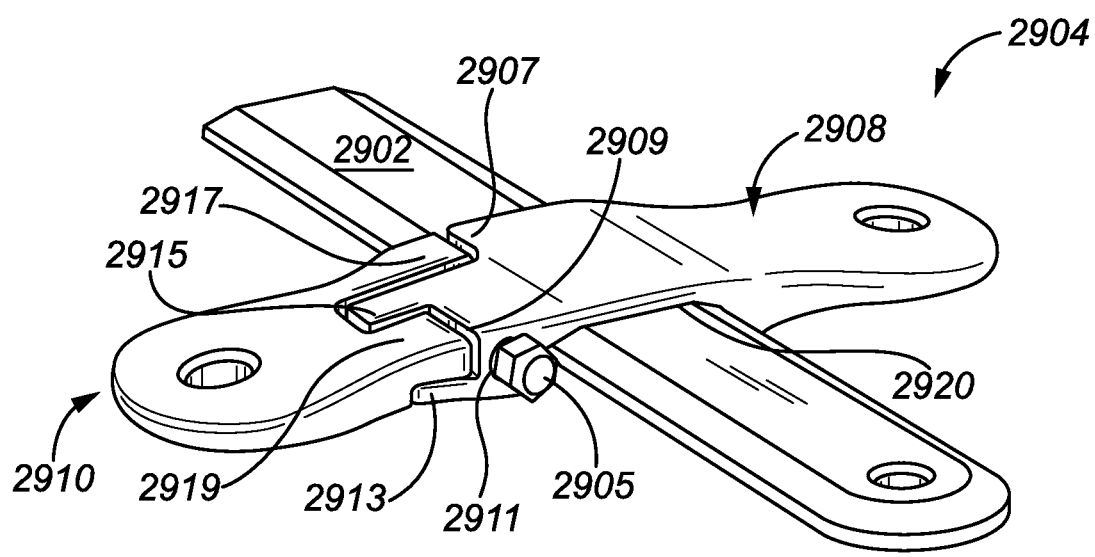
FIG. 29 illustrates an isometric view of a pectus bar assembly, in accordance with at least one example of the present disclosure.

FIG. 29 illustrates an isometric view of pectus bar assembly 2900, which can include pectus bar 2902 (only a portion of pectus bar 2902 is shown in FIG. 29), stabilizer 2904, and driver 2905. Stabilizer 2904 can include first portion 2908 and second portion 2910. First portion 2908 can include mating recess 2907, mating recess 2909, first driver bore 2911, mating extension 2913, first extension 2915, and recessed portion 2920. Second portion 2910 can include second extension 2917 and third extension 2919.

Stabilizer 2904 can include recessed portion 2920 can be configured to receive pectus bar 2902, similar to stabilizers discussed above, such that first portion 2908 can hook pectus bar 2902 to retain pectus bar 2902 within recessed portion 2920 of stabilizer 2904. Stabilizer 2904 differs in that second portion 2910 is translatable from an open position towards first portion 2908 to engage pectus bar 2902 and secure pectus bar 2902 to stabilizer 2904 in a closed position, where driver 2905 forces second portion 2910 to translate between the open and the closed positions.

More specifically, mating recess 2907 of first portion 2908 can receive second extension 2917 of second portion 2910. Also, mating recess 2909 of first portion 2908 can receive third extension 2919 of first portion 2910, which overlaps mating extension 2913 of first portion 2908. And, first extension 2915 of first portion 2908 can extend into a recess created between second extension 2917 and third extension 2919. In a closed position, the extensions and recesses of first portion 2908 and second portion 2910 can resist relative rotation of first portion 2908 and second portion 2910, and driver 2905 prevents translation of first portion 2908 relative to second portion 2910.

In operation of some examples, when stabilizer 2904 is in an open position, stabilizer 2904 can positioned to hook first portion 2908 onto pectus bar 2902 so that pectus bar 2902 resides in recessed portion 2920 of stabilizer 2904. Driver 2905 can then be rotated clock-wise to drive driver 2905 into stabilizer 2904 and force second portion 2910 to translate towards first portion 2908 into a closed position, where second portion 2910 contacts pectus bar 2902 and together with first portion 2908 retains pectus bar 2902 in recessed portion 2920 of stabilizer 2904. If desired, driver 2905 can be rotated counter-clockwise to translate first portion 2908 into an open position, disengaging first portion 2908 from pectus bar 2902 so that second portion 2910 can be unhooked from pectus bar 2902 and therefore removed from pectus bar 2902. Because driver 2905 is engageable from the side, stabilizer 2904 offers the benefit of being securable to pectus bar 2902 in cavities where top access to stabilizer 2904 is not available.

Before first portion 2908 is unhooked, stabilizer 2904 can be positioned along a length of pectus bar 2902 when second portion 2908 is in the open position and when first portion 2910 is hooked onto pectus bar 2902. This adjustability of stabilizer 2904 can increase procedural efficiency, saving time and cost.

Figure 30A:
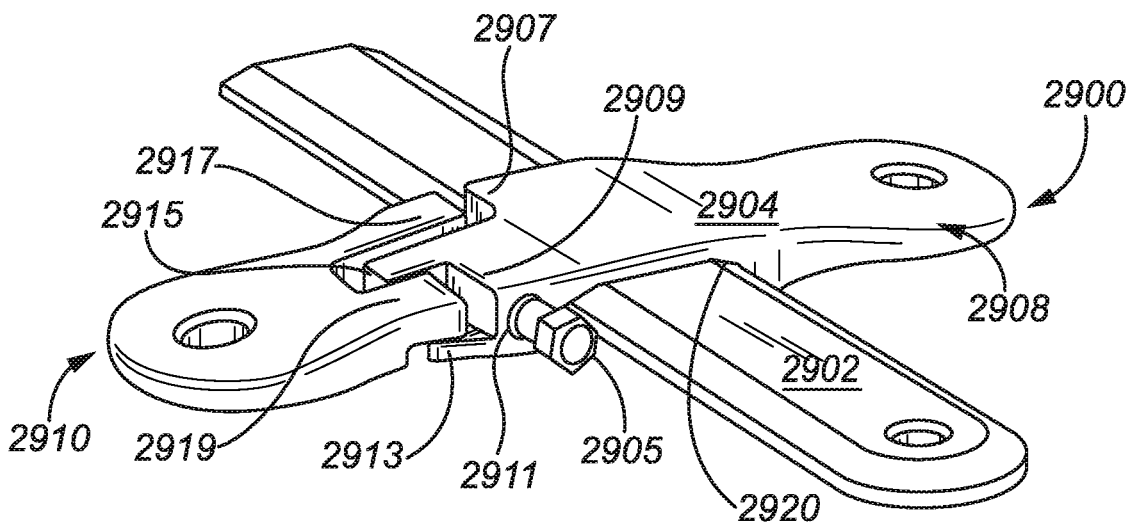
FIG. 30A illustrates atop isometric view of a pectus bar assembly in a first condition, in accordance with at least one example of the present disclosure.
Figure 30B:
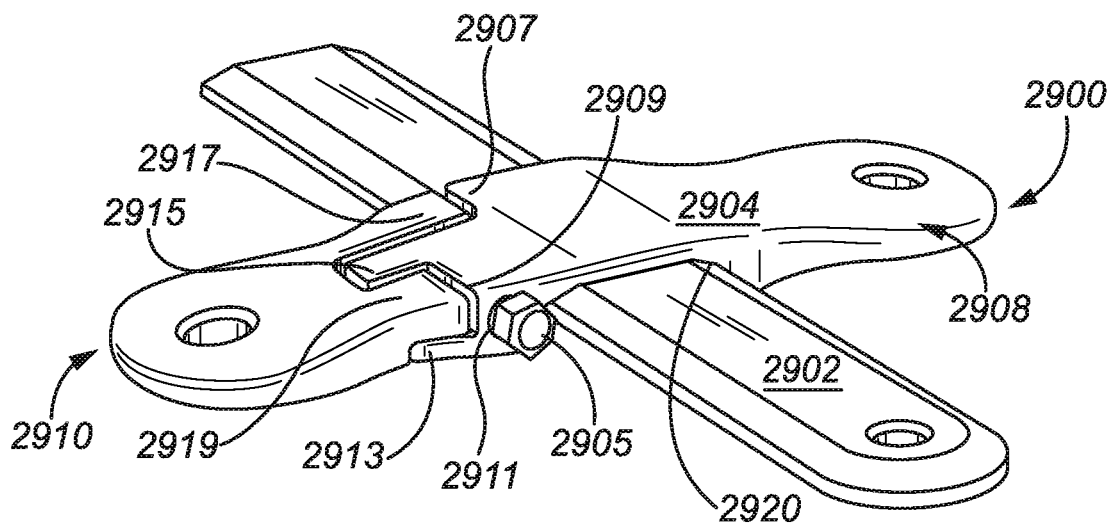
FIG. 30B illustrates atop isometric view of a pectus bar assembly in a second condition, in accordance with at least one example of the present disclosure.

FIG. 30A illustrates a top isometric view of pectus bar assembly 2900 in an unlocked position. FIG. 30B illustrates a top isometric view of pectus bar assembly 2900 in a locked position. FIGS. 30A and 30B are discussed below concurrently.

Pectus bar assembly 2900 can include pectus bar 2902, stabilizer 2904, and driver 2905. Stabilizer 2904 can include first portion 2908 and second portion 2910. First portion 2908 can include mating recess 2907, mating recess 2909, first driver bore 2911, mating extension 2913, first extension 2915, and recessed portion 2920. Second portion 2910 can include second extension 2917 and third extension 2919.

FIG. 30A shows how second portion 2910 translates away from first portion 2908 into an open position. When second portion 2910 is in the open position, as shown in FIG. 30A: mating recess 2907 is separated from second extension 2917; mating recess 2909 is separated from third extension 2919; mating extension 2913 is separated from second portion 2910; and, first extension 2915 is partially separated from second portion 2910. Also, in the open position, driver 2905 extends from driver bore 2911.

When second portion 2910 is in the closed position, as shown in FIG. 30B: mating recess 2907 contacts second extension 2917; mating recess 2909 contacts third extension 2919; mating extension 2913 contacts second portion 2910 and, each surface of first extension 2915 contacts second portion 2910. Also, in the closed position, driver 2905 fully threads into driver bore 2911.

Figure 31A:
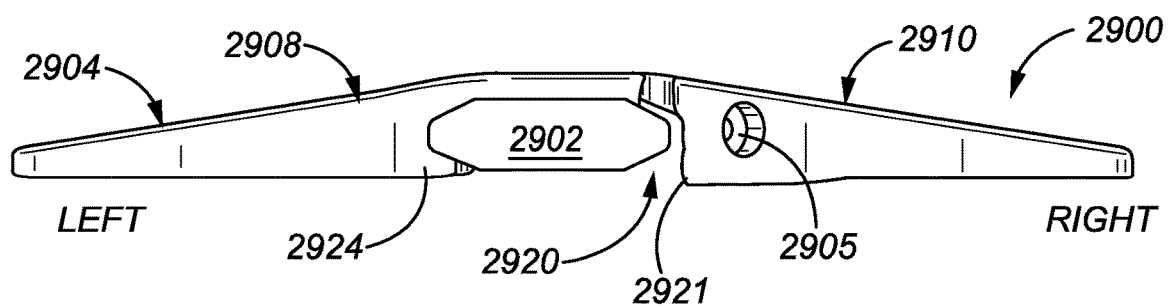
FIG. 31A illustrates aside isometric view of a pectus bar assembly in a first condition, in accordance with at least one example of the present disclosure.
Figure 31B:
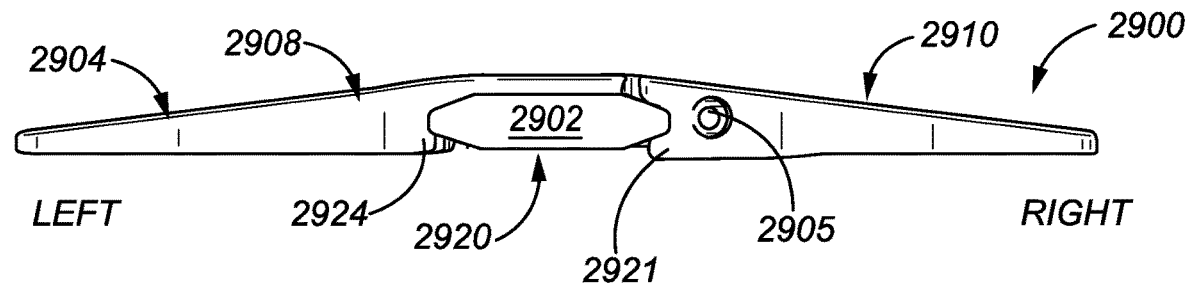
FIG. 31B illustrates aside isometric view of a pectus bar assembly in a second condition, in accordance with at least one example of the present disclosure.

FIG. 31A illustrates aside isometric view of pectus bar assembly 2900 in an unlocked position. FIG. 31B illustrates a side isometric view of pectus bar assembly 2900 in a locked position. FIGS. 31A and 31B are discussed below concurrently.

Pectus bar assembly 2900 can include pectus bar 2902, stabilizer 2904, and driver 2905. Stabilizer 2904 can include first portion 2908 and second portion 2910. First portion 2908 can include recessed portion 2920 and shelf 2924. Second portion 2910 can include translating shelf 2921.

As shown in FIG. 31A, when second portion 2910 of stabilizer 2904 is in an open position, shelf 2924 can contact and support a bottom chamfer of left side of pectus bar 2902 and a left edge, left upper chamfer, and a top of pectus bar 2902 can contact recessed portion 2920. However, a right upper chamfer, a right edge, and a right lower chamfer are not contacted by stabilizer 2904.

As shown in FIG. 31B, when second portion 2910 of stabilizer 2904 is in a closed position, the right lower chamfer is contacted by stabilizer 2904, where contact by translating shelf 2921 and right lower chamfer forces pectus bar 2902 to the left and up. Also, in the closed position, the right upper chamfer and the right edge of pectus bar 2902 are contacted by second portion 2910, preventing pectus bar 2902 from moving in any direction relative to stabilizer 2904.

Figure 32A:
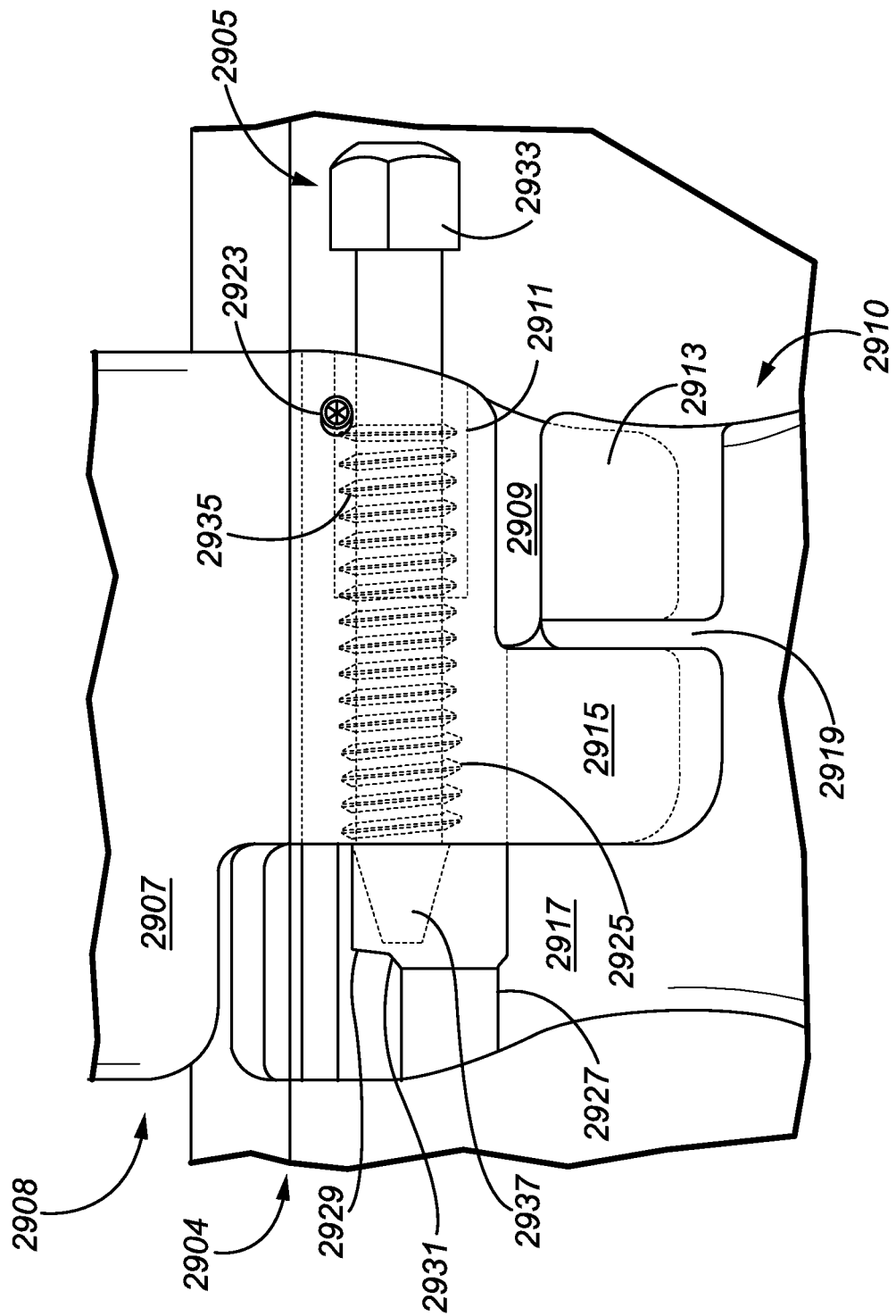
FIG. 32A illustrates atop cross-sectional view of a portion of a stabilizer in a first condition, in accordance with at least one example of the present disclosure.
Figure 32B:
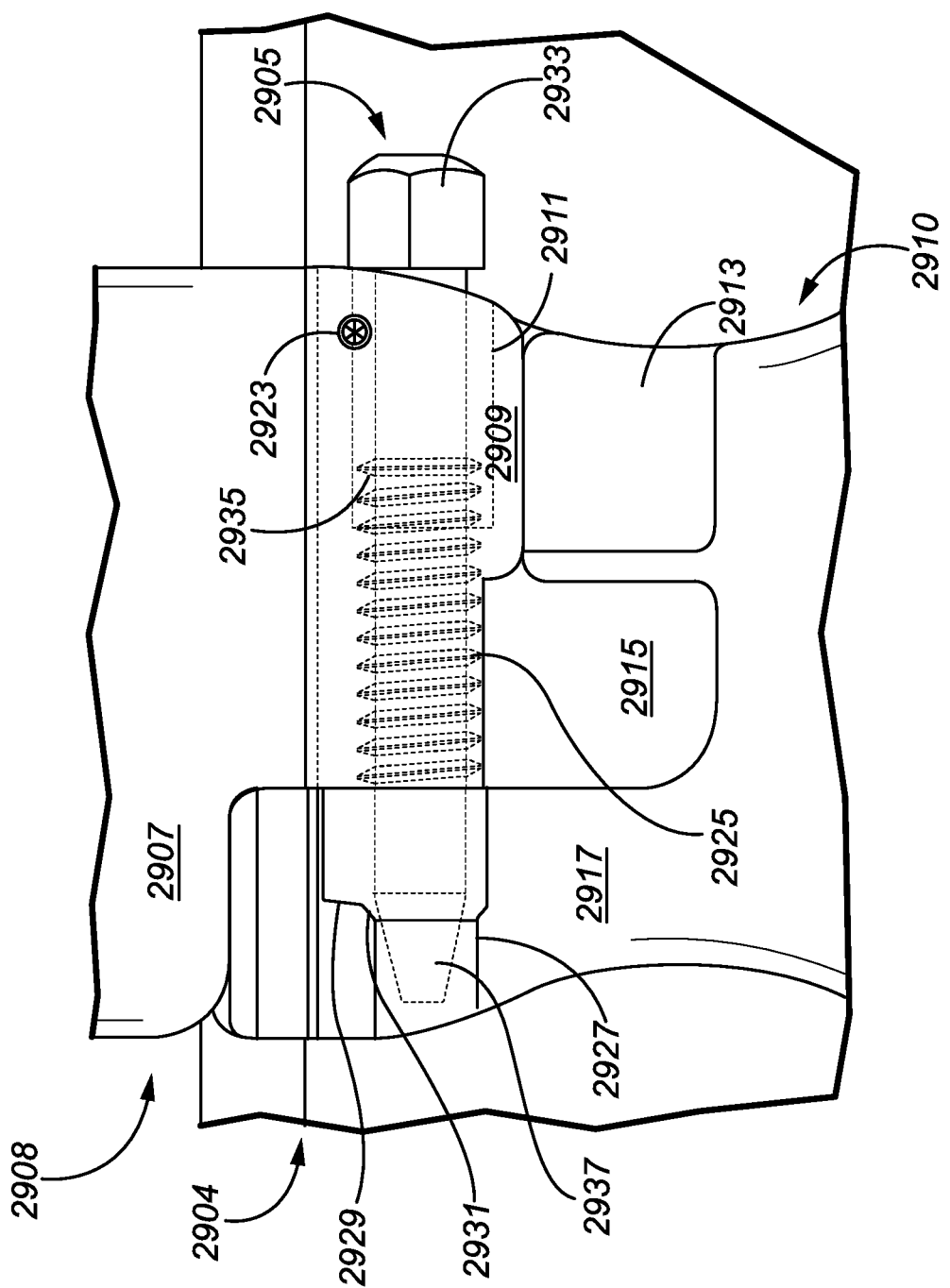
FIG. 32B illustrates atop cross-sectional view of a portion of a stabilizer in a second condition, in accordance with at least one example of the present disclosure.

FIG. 32A illustrates a top cross-sectional view of a portion of stabilizer 2904 in an unlocked position. FIG. 32B illustrates a top cross-sectional view of a portion of stabilizer 2904 in a locked position. FIGS. 32A and 32B are discussed below concurrently.

Stabilizer 2904 can include first portion 2908 and second portion 2910. First portion 2908 can include mating recess 2907, mating recess 2909, driver bore 2911, mating extension 2913, first extension 2915, retaining pin 2923, and threaded bore 2925. Second portion 2910 can include second extension 2917, third extension 2919, and driver bore 2927. Driver bore 2927 can include counter bore 2929 and chamfer 2931. Driver 2905 can include head 2933, threaded portion 2935, and tapered portion 2937.

Stabilizer 2904 of FIGS. 32A and 32B can be connected consistently with FIGS. 29-31B. However, FIGS. 32A and 32B show further details of stabilizer 2904, such as how driver is threadable into first portion 2908 and second portion 2910 to translate second portion 2910 into a closed position.

Driver 2905 includes head 2933 disposed at one end and tapered portion 2937 disposed at an opposite end, where threaded portion 2935 is disposed in between. Driver 2905 can pass through driver bore 2911 of first portion 2908, which can be a non-threaded bore having a diameter larger than threaded portion 2935 to allow for unrestricted movement of driver 2905 through driver bore 2911. First portion 2908 can also include threaded bore 2925, which can be coaxial with driver bore 2911, and can be threaded complementary to driver 2905. Pin 2923 can pass substantially transversely through driver bore 2911 near a wall of driver bore 2911. Pin 2923 can be installed after driver 2905 is inserted into driver bore 2911 and threaded bore 2925 to contact threaded portion 2935 of driver 2905, where contact between pin 2923 and threaded portion 2935 limits translation of driver 2905 out of driver bore 2911.

Second portion 2908 can include driver bore 2927 which can be coaxial with driver bore 2911 when second portion 2908 is in the closed position and offset from driver bore 2911 when second portion 2908 is in the open position. Driver bore 2927 can include counter bore 2929, which can be offset from driver bore 2927 towards first portion 2908. Chamfer 2931 can be formed on a surface between driver bore 2927 and counter bore 2929.

In operation of some examples, when second portion 2910 is in an open position, driver 2905 can be in an extended position from driver bore 2911, as shown in FIG. 32A. In this position tapered portion 2937 can reside in counter bore 2929 and threaded portion 2935 can contact pin 2923. When it is desired to move second portion 2910 to the closed position, driver 2905 can be rotated and threaded into threaded portion 2925. As tapered portion 2937 extends through counter bore 2929, tapered portion 2937 can contact chamfer 2931, which can apply a force on second portion 2910 causing second portion 2910 to translate towards first portion 2908. Because tapered portion 2910 is a tapered profile, movement of second portion 2910 towards first portion 2908 can be incremental as driver 2905 is rotated and translated towards driver bore 2927, until head 2933 of driver 2905 engages a side of stabilizer 2904, at which point first mating recess 2907 will contact second extension 2917, as described in further detail above. This process can be reversed by rotating driver 2905 in the opposite direction.

Figure 33:
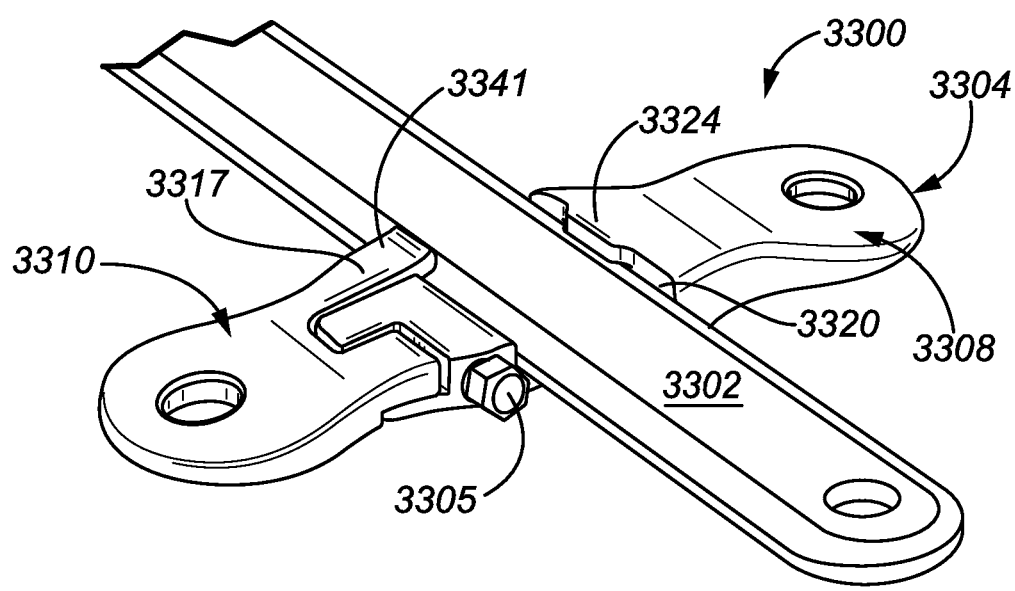
FIG. 33 illustrates an isometric view of a pectus bar assembly, in accordance with at least one example of the present disclosure.

FIG. 33 illustrates an isometric view of pectus bar assembly 3300, which can include pectus bar 3302, stabilizer 3304, and driver 3305. Stabilizer 3304 can include first portion 3308 and second portion 3310. First portion 3308 can include first shelf 3324. Second portion 3310 can include first extension 3317, which can include second shelf 3341.

Pectus bar assembly 3300 can be similar to pectus bar assembly 2900, except that pectus bar assembly 3300 is a bottom-mount, or recess 3320 is exposed on a top side of stabilizer 3304. Because of this, second extension 3317 includes second shelf 3341, which can engage and retain pectus bar 3302 when second portion 3310 is in a closed position.

Figure 34A:
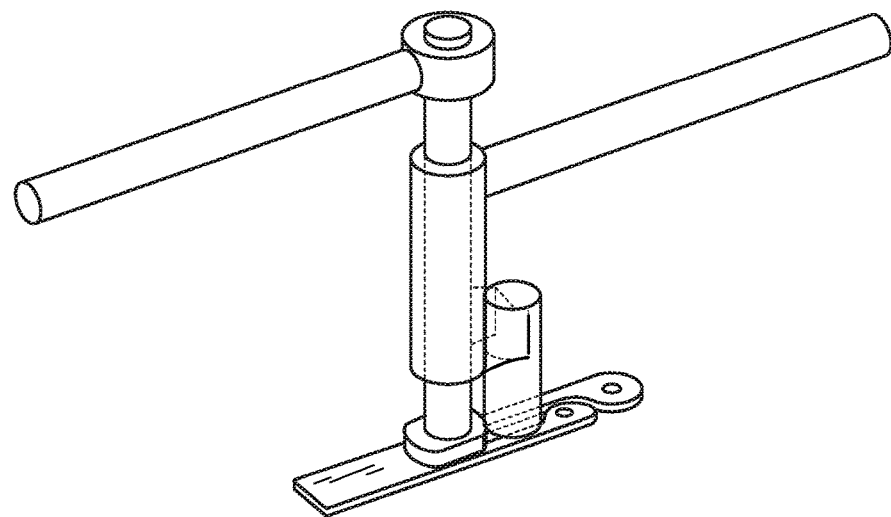
FIG. 34A illustrates a top isometric view of a stabilizer bar and tool, in accordance with at least one example of the present disclosure.
Figure 34B:
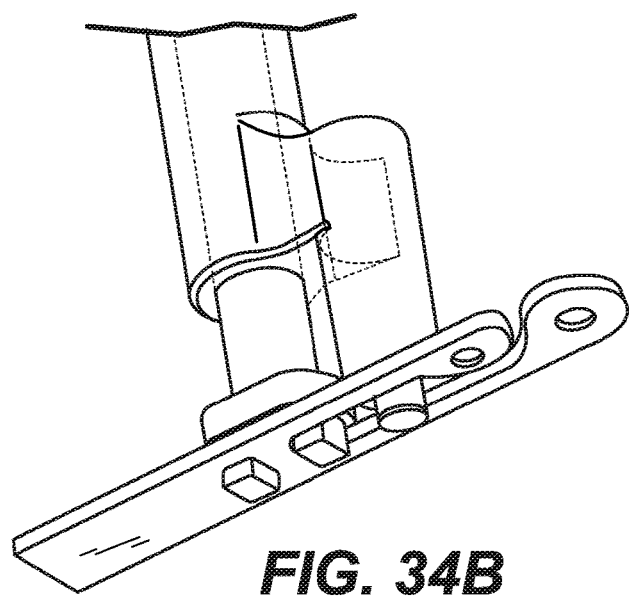
FIG. 34B illustrates a bottom isometric view of a stabilizer bar and tool, in accordance with at least one example of the present disclosure.
Figure 35:
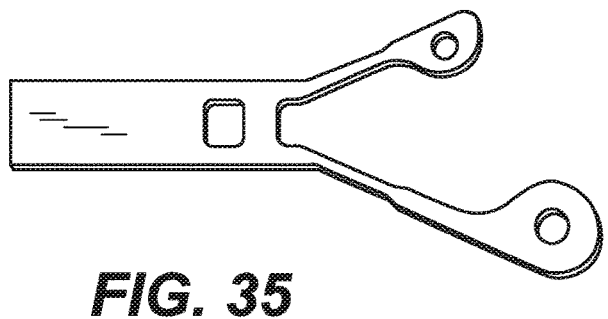
FIG. 35 illustrates a portion of a stabilizer bar, in accordance with at least one example of the present disclosure.

FIG. 34A illustrates a top isometric view of a pectus stabilizer bar and tool. FIG. 34B illustrates a bottom isometric view of a stabilizer bar and tool. FIG. 35 illustrates a portion of a stabilizer bar. FIGS. 34A, 34B, and 35 are discussed below concurrently.

A pectus bar can include multiple arms including bores for attaching the pectus bar to multiple ribs. The arms can be separable to different positions, as desired. In some examples, the pectus bar can include a bore and a channel configured to receive a torque tool. The torque tool can include one or more handles for delivering a torque to the stabilizer bar.

In operation of some examples, a physician can apply a torque to the tool, which can transfer the torque to one of the arms as the tool rotates about the bore, separating the arms from each other, as desired. When one arm is moved, the tool can be used again to force the other arm further away from the first arm. Once the arms have been separated as desired (as shown in FIG. 35), the arms can be secured to ribs of a human chest wall, for examples, using sutures. The bores of the stabilizer bar, when the arms are spread, can have a similar relative locations to where stabilizer holes would be or similar to the location. These stabilizer bars can eliminate a need for a second stabilizer at either end of a pectus bar, which can save time during a corrective procedure and can save hardware cost.

Figure 36A:
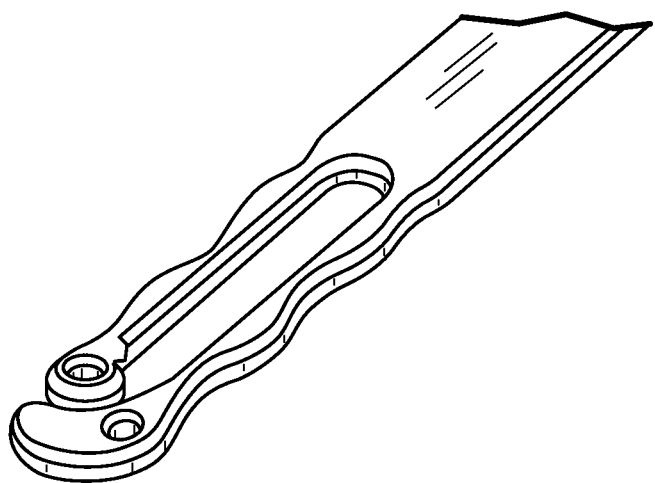
FIG. 36A illustrates a portion of a stabilizer bar, in accordance with at least one example of the present disclosure.
Figure 36B:
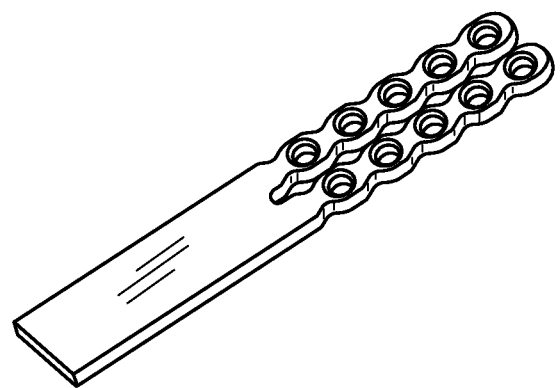
FIG. 36B illustrates a portion of a stabilizer bar, in accordance with at least one example of the present disclosure.

FIG. 36A illustrates a portion of a stabilizer bar. The stabilizer bar of 36A can be similar to that of FIGS. 34A and 34B, but can include arms having non-linear, undulated, or wavy peripheries. FIG. 36B illustrates a portion of another example of a pectus stabilizer bar, where each arm of the pectus stabilizer bar can include a plurality of bores, which can offer relatively more options for securing the pectus stabilizer bar to a chest wall.

Figure 37:
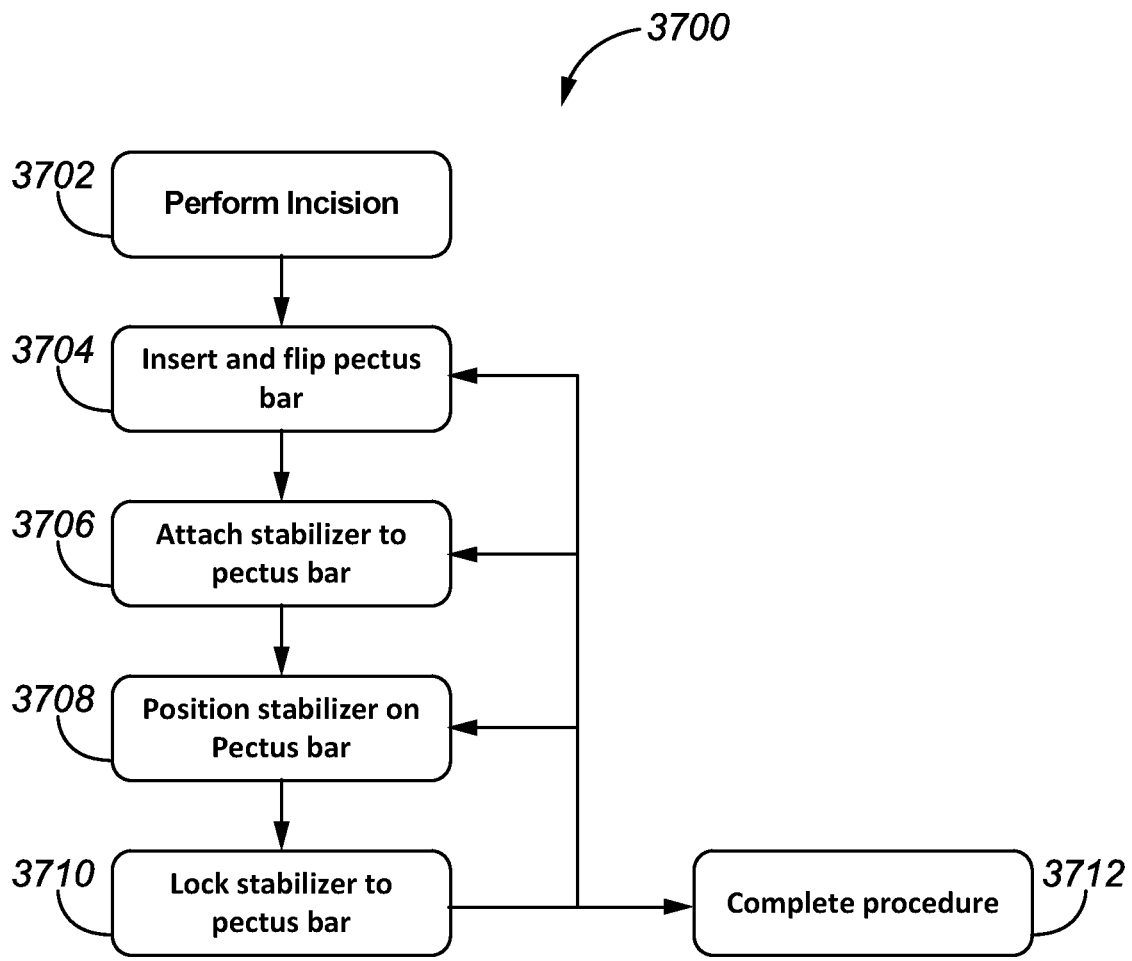
FIG. 37 illustrates a schematic of a method, in accordance with at least one example of the present disclosure.

FIG. 37 illustrates a flow chart of using the devices and systems described above, in accordance with at least one example of this disclosure. The steps or operations of the method of FIG. 37 are illustrated in a particular order for convenience and clarity. Many of the discussed operations can be performed in a different sequence or in parallel, and some operations may be excluded, without materially impacting other operations. The method of FIG. 37, as discussed, includes operations that may be performed by multiple different actors, devices, and/or systems. It is understood that subsets of the operations discussed in the method of FIG. 37 that are attributable to a single actor, device, or system could be considered a separate standalone process or method.

In operation of one example, a physician can create one or more incisions on a chest wall of a patient at step 3702. Other preparations can be made at step 3702, such as detachment of soft tissues and resection or removal of ribs, in some examples. At step 3704, a pectus bar, such as pectus bar 202, can be inserted into the chest wall and woven through ribs and cartilage of the patient. Once fully inserted, the pectus bar can be flipped into an orientation that supports a proper chest wall shape or configuration. At any point after step 3704 and prior to step 3712, the pectus bar can be directly secured to the patient's ribs using sutures and/or fasteners, as necessary, passing through or around a bore of the pectus bar.

At step 3706, the stabilizer can be attached to the pectus bar and then positioned relative to the pectus bar at step 3708. A stabilizer tool, driver, or appendage can then be used to lock a locking mechanism of the stabilizer to secure the stabilizer to the pectus bar at step 3710. Following step 3710, if necessary, the stabilizer can be unlocked and the stabilizer can be repositioned on the pectus bar. Accordingly, steps 3706 through 3710 can be repeated as necessary to lock the stabilizer to the pectus bar in the desired location. Additionally, steps 3706 through 3710 can be repeated to install a second, third, and the like, stabilizer on the pectus bar. In some examples, steps 3704 can repeated where a second, third, and the like, pectus bar can be installed, where each stabilizer can receive one or more stabilizers.

Once the stabilizer is locked to the pectus bar at a desired location, the procedure can be completed at step 3712, which can include connecting soft tissues, such as muscles, ligaments, cartilage, tendons, and bones, and can include closing the incision or incisions.

Additional Notes

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. A pectus bar stabilizer securable to a. pectus bar, the stabilizer comprising:
   a body comprising:
     a first portion engageable with a first lateral side of the pectus bar; and
     a second portion connected to the first portion; and
   a locking cam rotatable within the second portion to engage and apply a force to a second lateral side of the pectus bar to secure the stabilizer to the pectus bar;
   wherein the first portion includes a shelf engageable with the first lateral side:
   wherein the second portion includes a cam bore and wherein the locking cam is located within and rotatable within the cam bore; and
   wherein the cam bore extends through a recess and the locking cam is rotatable to a locked position to extend into the recess to engage the second lateral side of the pectus bar.

2. The pectus bar stabilizer of claim 1, wherein the cam bore defines a first notch and wherein the locking cam includes a projection engageable with the first notch to limit rotation of the locking cam within the cam bore and maintain the locking cam in the locked position, thereby securing the stabilizer to the pectus bar.

3. The pectus bar stabilizer of claim 2, wherein the cam bore includes a second notch, and wherein the projection is engageable with the second notch to limit rotation of the locking cam within the cam bore maintaining the locking cam in a partially engaged position.

4. The pectus bar stabilizer of claim 3. wherein the cam bore includes a third notch, wherein the projection is engageable with the third notch to limit rotation of the locking cam within the cam bore, maintaining the locking cam in an open position.

5. The pectus bar stabilizer of claim 2, wherein the cam bore includes a bore stop configured to engage the locking cam to set a rotational limit of the locking cam within the cam bore.

6. A pectus bar stabilizer comprising:
   a body comprising:
     a first portion engageable with a pectus bar; and
     a second portion connected to the first portion and, together with the first portion, defining a recess;
     a stabilizer shelf extending into the recess and towards the locking cam, the stabilizer shelf engageable with the second portion; and
   a locking cam rotatable within the second portion, a lower portion of the locking cam configured to extend through the recess to engage the pectus bar and apply a force to the pectus bar to secure the stabilizer to the pectus bar, the locking cam including a cam shelf engageable with the pectus bar.

7. The pectus bar stabilizer of claim 6, wherein the stabilizer is securable to the pectus bar at any point along a length of the pectus bar.

8. The pectus bar stabilizer of claim 6, wherein the locking cam includes a tool interface engageable with a tool and angled to be flush with a top surface of the second portion of the stabilizer body when the locking cam is in a locked position.

9. The pectus bar stabilizer of claim 6, the locking cam further comprising:
   a bar stop engageable with the pectus bar to limit rotation of the locking cam relative to the pectus bar.

10. A pectus bar stabilizer securable to a pectus bar, the stabilizer comprising:
- a body defining a recess, the body comprising:
    - a first portion including a shelf engageable with the pectus bar; and
    - a second portion connected to the first portion, the second portion defining a cam bore; and
- a locking cam located at least partially within and rotatable within the cam bore of the second portion to extend into the recess to apply a force to a lateral side of the pectus bar to secure the stabilizer to the pectus bar, the locking cam including a cam shelf engageable with the pectus bar.

11. The pectus bar stabilizer of claim 10, wherein the cam bore extends through the cam recess and the cam is rotatable to a locked position to extend into the cam recess to engage the pectus bar.

12. The pectus bar stabilizer of claim 11, wherein the cam bore defines:
- a first notch, the locking cam including a projection engageable with the first notch to limit rotation of the locking cam within the cam bore and maintain the locking cam in the locked position, thereby securing the stabilizer to the pectus bar;
- a second notch, the projection engageable with the second notch to restrict rotation of the locking cam within the cam bore maintaining the locking cam in a partially engaged position; and
- a third notch, the projection engageable with the third notch to restrict rotation of the locking cam within the cam bore, maintaining the locking cam in an open position.

13. The pectus bar stabilizer of claim 11, the bore further comprising:
- a bore stop configured to engage the locking cam to define a rotational limit of the locking cam within the cam bore.

14. The pectus bar stabilizer of claim 13, the locking cam further comprising:
- a bar stop engageable with the pectus bar to limit rotation of the locking cam relative to the pectus bar.

* * * * *